(12) United States Patent
Ikota et al.

(10) Patent No.: US 6,365,425 B1
(45) Date of Patent: Apr. 2, 2002

(54) METHOD OF MANUFACTURING SEMICONDUCTOR DEVICE

(75) Inventors: Masami Ikota, Higashiyamato; Aritoshi Sugimoto, Tokyo; Hisato Nakamura, Kodama, all of (JP)

(73) Assignees: Hitachi, Ltd.; Hitachi Electronics Engineering Co., Ltd., both of Tokyo (JP)

( * ) Notice: Subject to any disclaimer, the term of this patent is extended or adjusted under 35 U.S.C. 154(b) by 0 days.

(21) Appl. No.: 09/604,251

(22) Filed: Jun. 27, 2000

(30) Foreign Application Priority Data

Jun. 28, 1999 (JP) ............................. 11-182295

(51) Int. Cl.[7] ..................... H01L 21/66; H01L 21/00; G01R 31/26
(52) U.S. Cl. ................... 438/16; 438/7; 438/8; 438/15; 438/17; 438/18
(58) Field of Search ............... 438/16, 7, 15, 438/18, 8, 17, 706

(56) References Cited

U.S. PATENT DOCUMENTS

| | | | | |
|---|---|---|---|---|
| 5,384,463 A | * | 1/1995 | Honjo et al. | 250/398 |
| 5,436,464 A | * | 7/1995 | Hayano et al. | 250/225 |
| 5,528,360 A | * | 6/1996 | Kohno | 356/237 |
| 5,877,035 A | * | 3/1999 | Fujino et al. | 438/16 |

* cited by examiner

Primary Examiner—Matthew Smith
Assistant Examiner—Igwe U. Anya
(74) Attorney, Agent, or Firm—Antonelli, Terry, Stout & Kraus, LLP

(57) ABSTRACT

A method of manufacturing a semiconductor device includes fetching inspection chip information including information of a dust-particle/fault on an inspection chip by irradiating the inspection chip of a semiconductor wafer with an optical beam and by detecting the scattering/diffracting beam of the optical beam, fetching reference chip information as information of a reference chip without a dust-particle/fault, comparing the inspection chip information and the reference chip information to determine a dust-particle/fault, and determining whether the dust-particle/fault is located on a pattern or outside of the pattern by matching between the dust-particle/fault information and design pattern data as data of a prepared pattern. The dust-particle/fault is determined to be a fatal dust-particle/fault when the dust-particle fault is located on the pattern or to be a non-fatal dust-particle fault when the dust-particle/fault is located outside of the pattern.

9 Claims, 36 Drawing Sheets

PATTERN EXPANDING PROCESS →

| 0 | 0 | 0 | 0 | 0 | 0 | 0 | 0 |
|---|---|---|---|---|---|---|---|
| 0 | 1 | 1 | 1 | 0 | 1 | 1 | 0 |
| 0 | 1 | 1 | 1 | 0 | 1 | 1 | 0 |
| 0 | 1 | 1 | 1 | 0 | 1 | 1 | 0 |
| 0 | 0 | 0 | 0 | 0 | 1 | 1 | 0 |
| 0 | 0 | 0 | 0 | 0 | 1 | 1 | 0 |
| 0 | 1 | 1 | 1 | 1 | 1 | 1 | 0 |
| 0 | 1 | 1 | 1 | 1 | 1 | 1 | 0 |

| 0 | 0 | 0 | 0 | 0 | 0 | 0 | 0 |
|---|---|---|---|---|---|---|---|
| 0 | 2 | 2 | 2 | 0 | 2 | 2 | 0 |
| 0 | 2 | 4 | 4 | 0 | 4 | 2 | 0 |
| 0 | 2 | 4 | 8 | 0 | 4 | 2 | 0 |
| 0 | 0 | 0 | 0 | 0 | 4 | 2 | 0 |
| 0 | 0 | 0 | 0 | 0 | 4 | 2 | 0 |
| 0 | 2 | 2 | 2 | 2 | 2 | 2 | 0 |
| 0 | 1 | 1 | 1 | 1 | 1 | 1 | 0 |

METHOD OF MANUFACTURING SEMICONDUCTOR DEVICE

BACKGROUND OF THE INVENTION

Field of the Invention

The present invention relates to a semiconductor device manufacturing technique and particularly to the technique which can effectively be adapted for acquisition of positional relationship information between dust-particle/fault and pattern in the external appearance inspection.

The technique explained below has sufficiently been discussed by the inventors of the present invention on the occasion of studying and completing the present invention and the summary of this technique is as follows.

Particularly, in the pre-process of the semiconductor manufacturing process, various types of external appearance inspection apparatus are used for the external appearance inspection of a semiconductor wafer or a semiconductor chip.

These external appearance inspection apparatus outputs sizes and number of dust-particles and faults.

For example, WO98/01903 describes the inspection technique in the semiconductor manufacturing process and the uniform technique of the coordinate system in each inspection is described there.

However, it is impossible in the external appearance inspection apparatus of the technique explained above to obtain the information about the generating position of such dust-particles and faults.

Therefore, it is impossible to detect the positional relationship between dust-particle/fault and pattern and thereby here rises a problem that fatal and non-fatal dust-particles/fault cannot be determined.

Namely, on the occasion of surveying the mutual relationship between the dust-particle/fault and yield, it is required to know the fatal coefficient of dust-particle/fault detected by the external appearance inspection apparatus. For this purpose, the positional relationship information among size of dust-particle/fault, generating position of dust-particle/fault and pattern (to know that the dust-particles/fault is generated on the pattern, or at the outside of pattern or in the memory mat or peripheral circuit) is required, but it has been impossible to obtain the information about the generating position, although the external appearance inspection apparatus can output the information about size of.

SUMMARY OF THE INVENTION

It is therefore an object of the present invention to provide a method of manufacturing a semiconductor device in which the fatal/non-fatal condition of the dust-particle/fault is obtained in the external appearance inspection and the result of this inspection is reflected on the semiconductor manufacturing process.

The aforementioned and other objects and features of the present invention will become apparent from the description of this specification and attached drawings.

The typical inventions among those disclosed in the present invention will be briefly explained below.

Namely, the method of manufacturing the semiconductor device of the present invention comprises a process to fetch the chip information for inspection which is the information including dust-particle/fault on the inspection chip by radiating the optical beam to the inspection chip of semiconductor wafer supported to freely move on the stage and then detecting the scattering/diffraction beam, a process to fetch the chip information for reference by radiating the optical beam to the reference chip of the semiconductor wafer which is assumed to have no dust-particle/fault, a process to obtain the dust-particle/fault information indicating position and size of dust-particle/fault on the inspection chip by comparing the inspection chip information with the reference chip information, a process to determine whether the dust-particles/fault is located on the pattern or at the outside of pattern by matching the dust-particle/fault information with the design pattern data which is the prepared pattern data, and a process to define such dust-particle/fault to the fatal condition when the dust-particle/fault is located on the pattern but to define such dust-particle/fault to the non-fatal condition when it is located at the outside of pattern.

Therefore, the fatal/non-fatal condition of dust-particles/fault can be determined.

Moreover, the method for manufacturing a semiconductor device of the present invention comprises a process to fetch first area information including dust-particle/fault of the first area of the main surface of the semiconductor wafer by radiating an optical beam to the main surface of the semiconductor wafer supported to move with the stage and then detecting the scattering/diffracting beam, a process to fetch second area information by radiating the optical beam to the second area different from the first area of the semiconductor wafer, a process to obtain the dust-particle/fault information such as position and size of the dust-particle/fault of the first area by comparing the first area information with the second area information, a process to obtain the pattern information of the second area with a Fourier image processing system by fetching the Fourier image of the second area, a process to determine existence of the pattern depending on the pattern information of the second area for the dust-particle/fault position depending on the dust-particle/fault information and a process to define the fatal dust-particle/fault when it is determined that the pattern exists in the position of dust-particles/fault and also define the non-fatal dust-particles/fault when it is determined that the pattern does not exist at the position of dust-particle/fault.

DETAILED DESCRIPTION OF THE PREFERRED EMBODIMENTS

Figure 1:
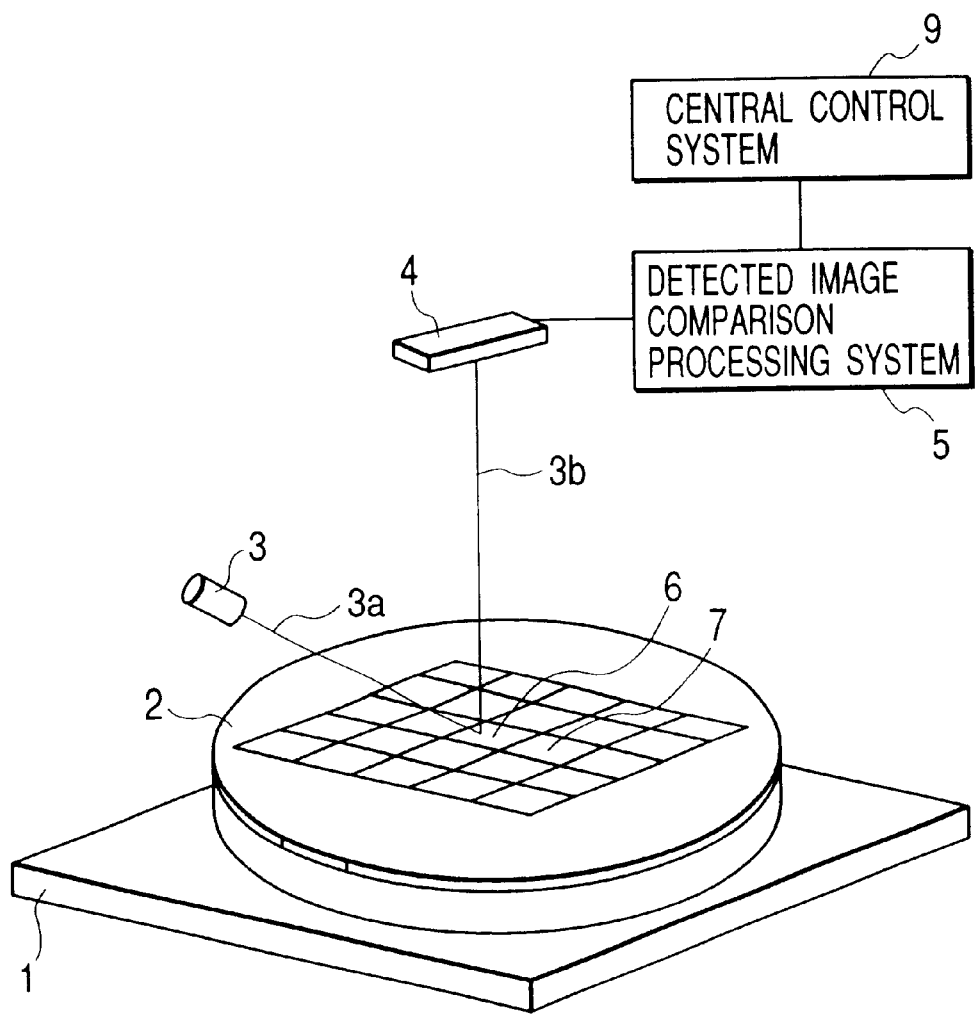
FIG. 1 is a perspective view illustrating an example of the structure of essential portion of the external appearance inspection apparatus of the first embodiment used in the inspection process of the method for manufacturing semiconductor device of the present invention.

The preferred embodiments of the present invention will be explained in detail with reference to the accompanying drawings. The structural elements having the like functions are designated with the like reference numerals throughout the drawings.

FIG. 1 is a perspective view illustrating an example of the structure of essential portion of the external appearance inspection apparatus of the first embodiment used in the inspection process of the method for manufacturing semiconductor device of the present invention.

Figure 2:
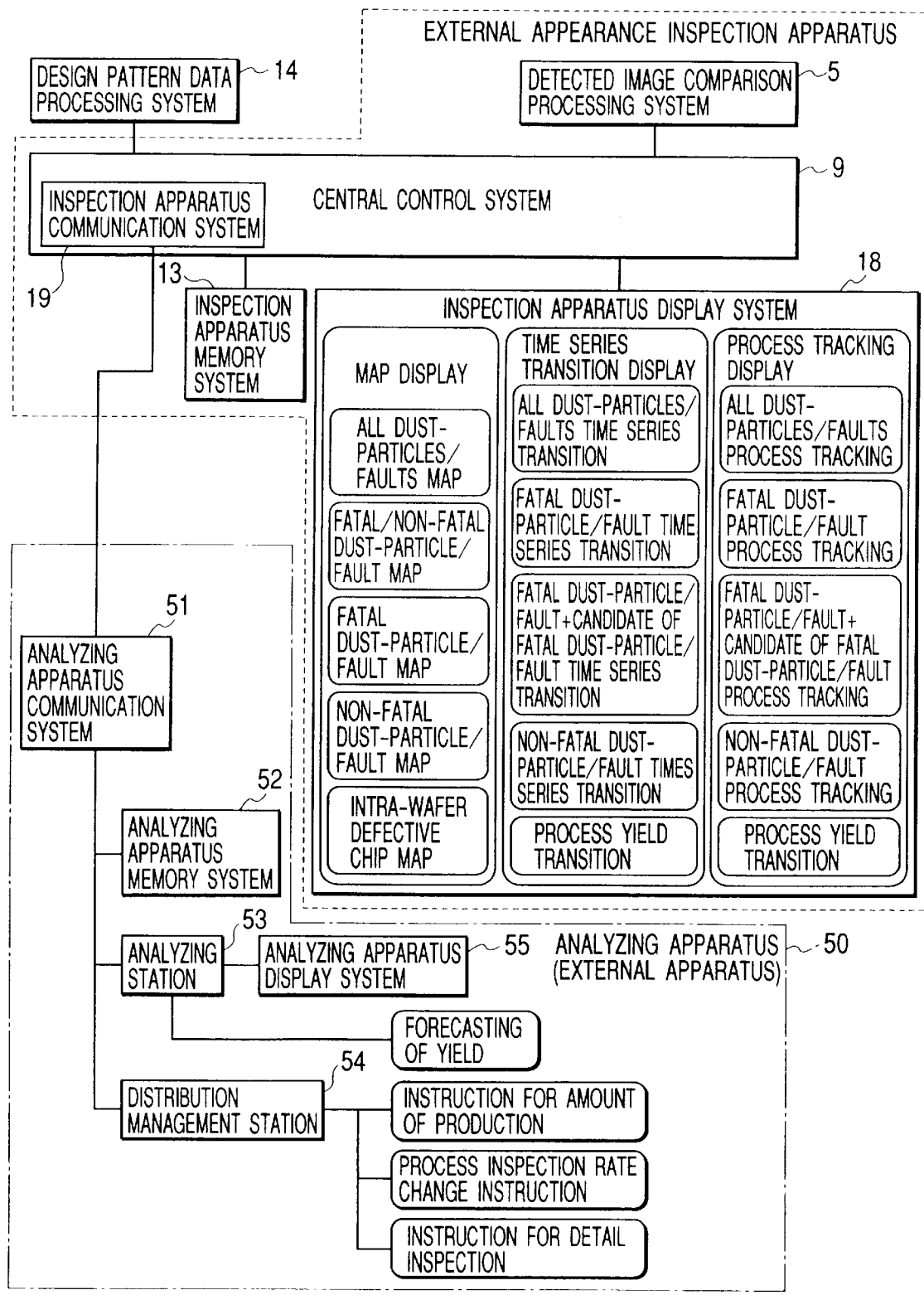
FIG. 2 is a block diagram illustrating an example of the structure of essential portions of the external appearance inspection apparatus of FIG. 1 and the external apparatus connected thereto.

FIG. 2 is a block diagram illustrating an example of the structure of essential portions of the external appearance inspection apparatus of FIG. 1 and the external apparatus connected thereto.

Figure 3:
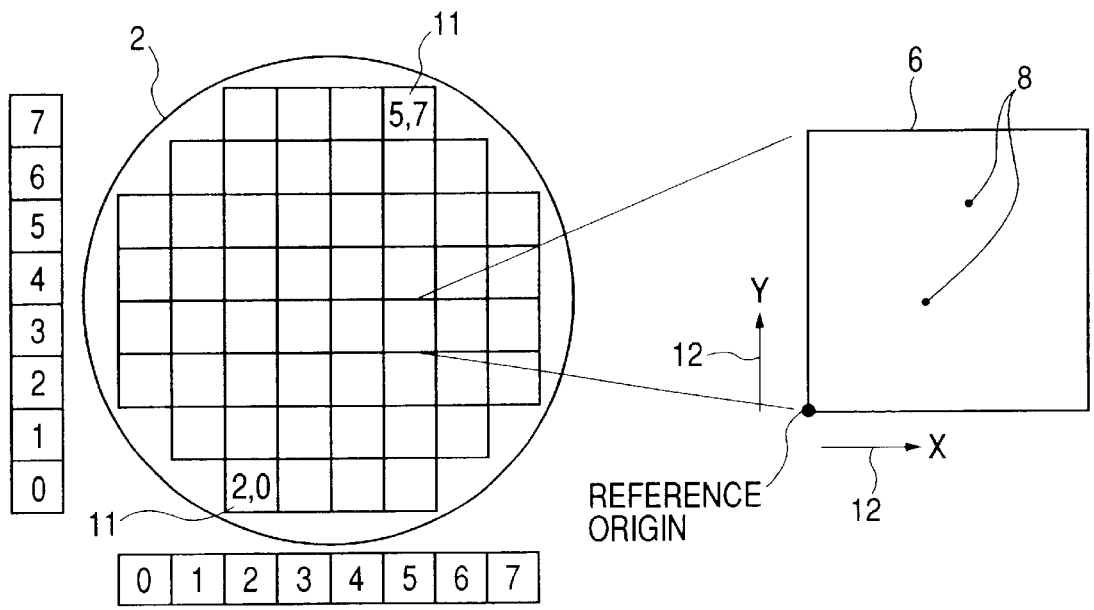
FIG. 3 is a chip layout illustrating an example of a chip matrix used in the external appearance inspection apparatus of FIG. 1.

FIG. 3 is a chip layout illustrating an example of a chip matrix used in the external appearance inspection apparatus of FIG. 1.

Figure 4A:
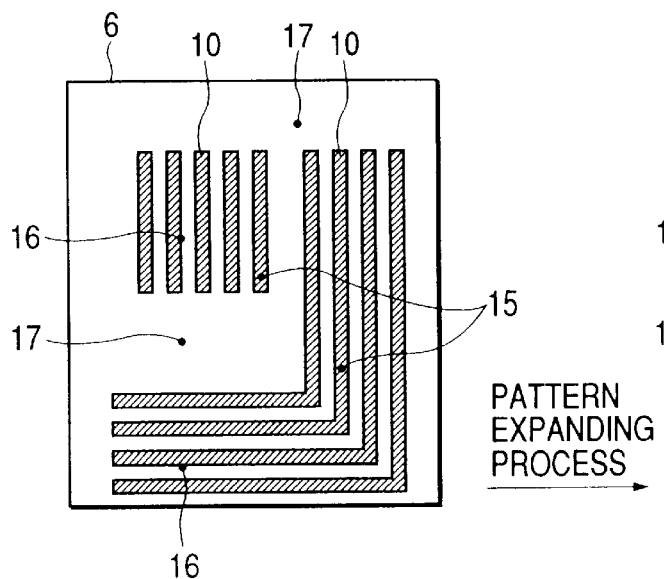
FIGS. 4(a), 4(b) illustrate examples of the fatal and non-fatal condition determining method used in the inspection process for the method for manufacturing semiconductor device of the first embodiment of the present invention, including the pattern diagram before the expanding process (a) and the pattern diagram after the expanding process (b).
Figure 4B:
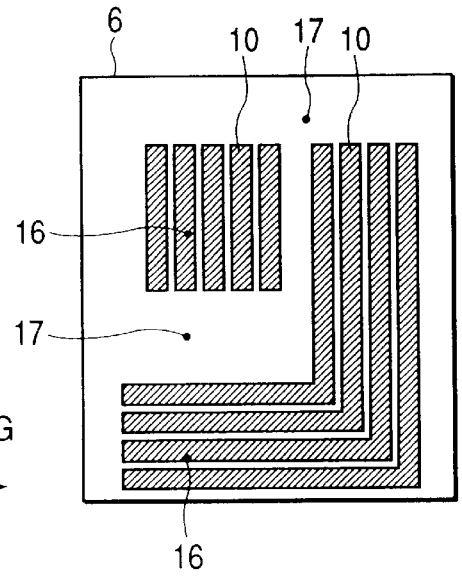

FIGS. 4(a), 4(b) illustrate examples of the fatal and non-fatal condition determining method used in the inspection process for the method for manufacturing semiconductor device of the first embodiment of the present invention, including the pattern diagram before the expanding process (a) and the pattern diagram after the expanding process (b).

Figure 5:
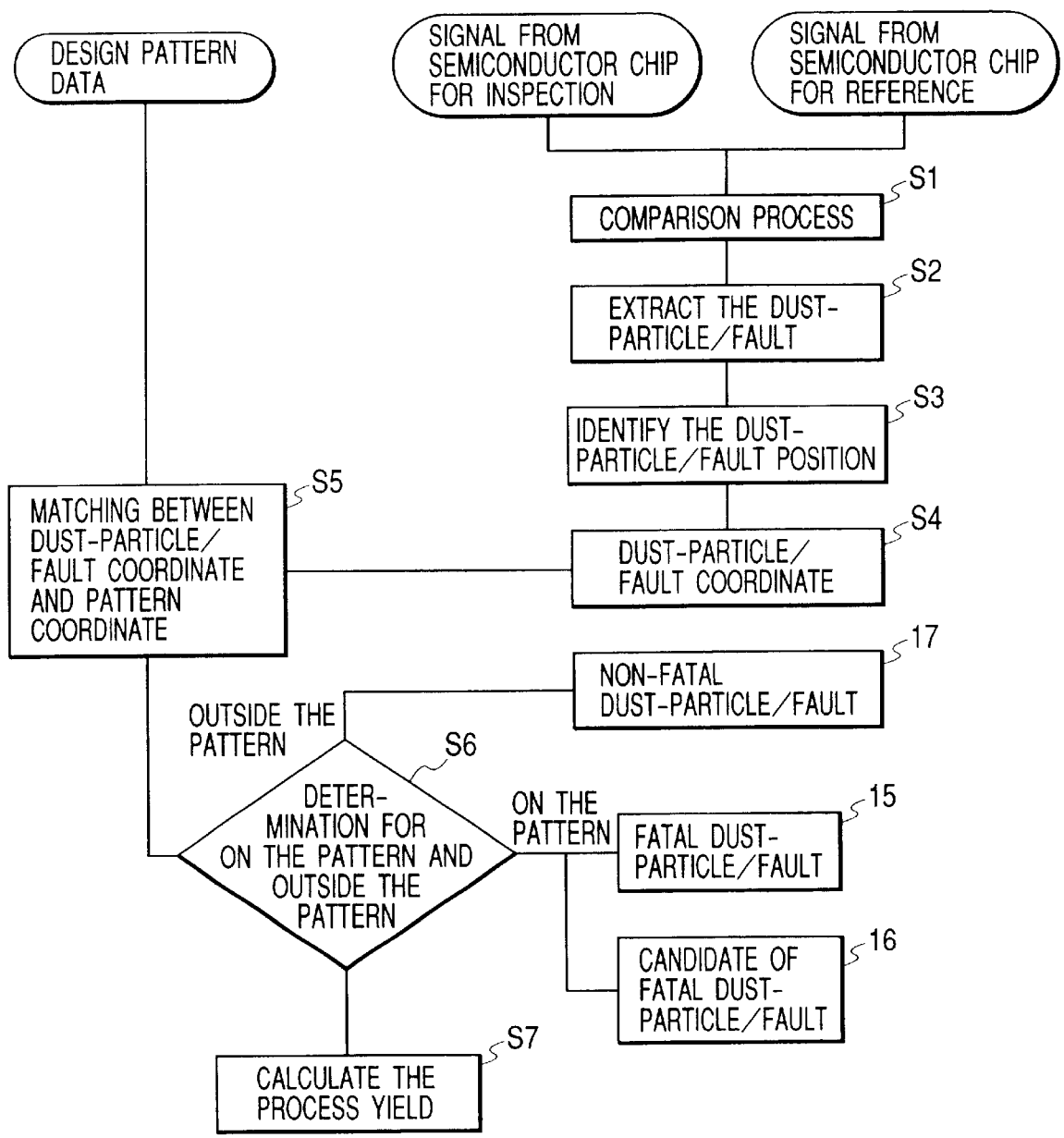
FIG. 5 is a flowchart of inspection sequence illustrating an example of the inspection sequence executed in the inspection process for the method for manufacturing semiconductor device of the embodiment 1 of the present invention.

FIG. 5 is a flowchart of inspection sequence illustrating an example of the inspection sequence executed in the inspection process for the method for manufacturing semiconductor device of the embodiment 1 of the present invention.

Figure 6:
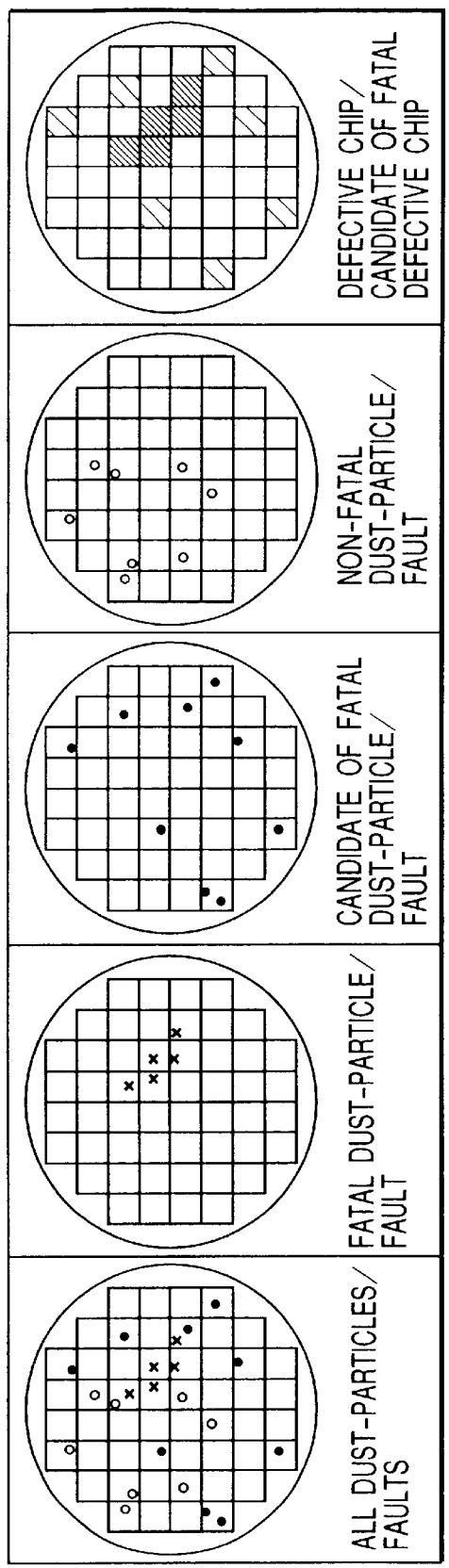
FIG. 6 is a map diagram illustrating chip map information as an example of the method for displaying inspection result for fatal/non-fatal condition determination with the external appearance inspection apparatus of FIG. 1.

FIG. 6 is a map diagram illustrating chip map information as an example of the method for displaying inspection result for fatal/non-fatal condition determination with the external appearance inspection apparatus of FIG. 1.

Figure 7:
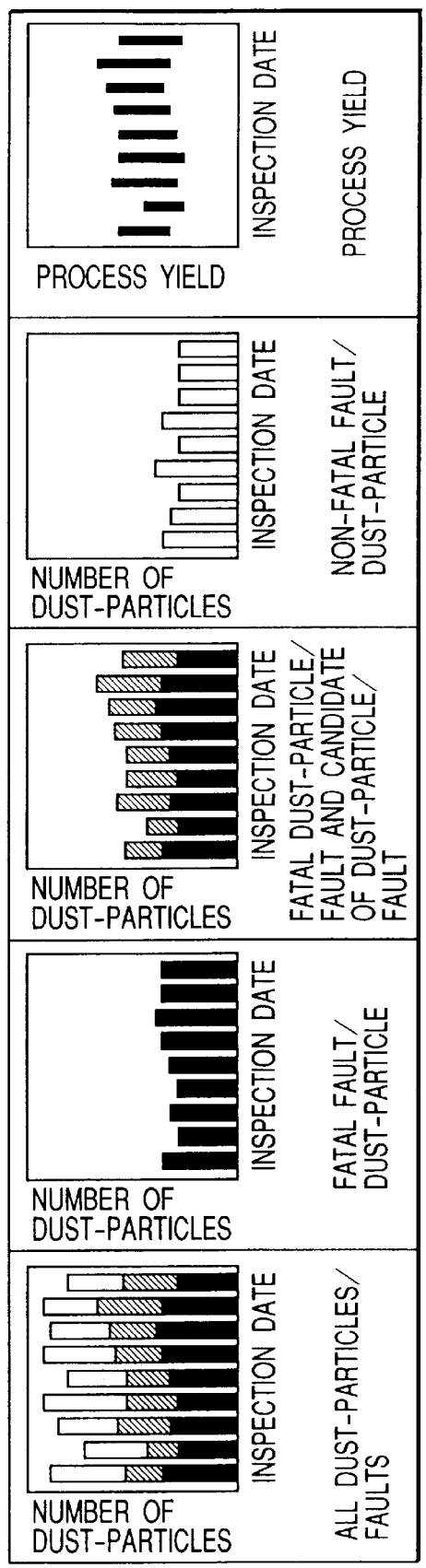
FIG. 7 is a time series transition diagram indicating the time series transition information as an example of the method for displaying inspection result of the fatal/non-fatal condition determination with the external appearance inspection apparatus of FIG. 1.

FIG. 7 is a time series transition diagram indicating the time series transition information as an example of the method for displaying inspection result of the fatal/non-fatal condition determination with the external appearance inspection apparatus of FIG. 1.

Figure 8:
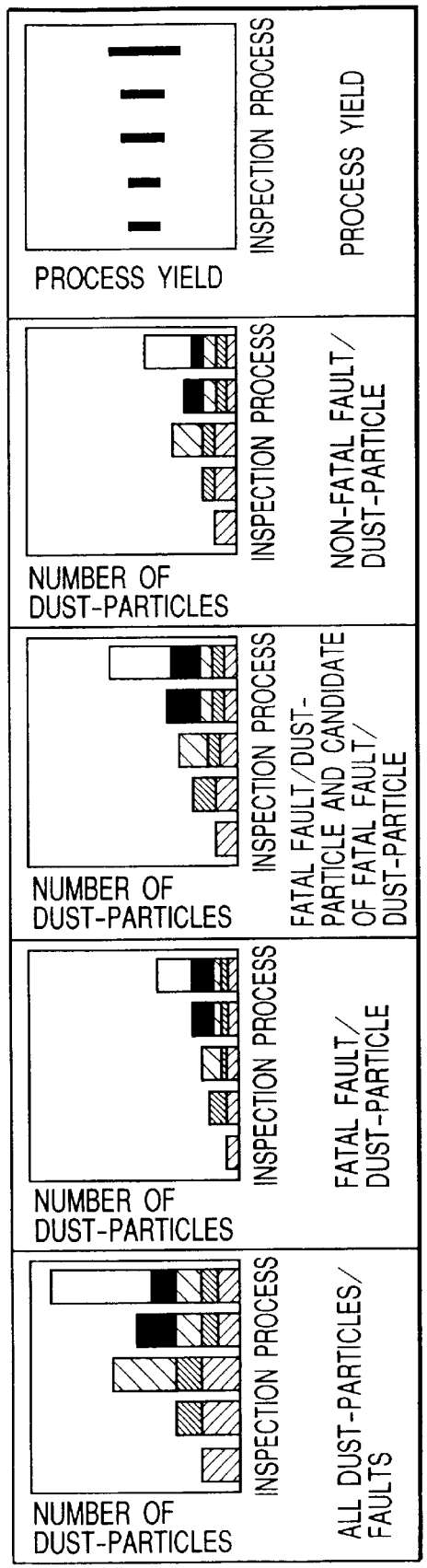
FIG. 8 is a process tracking diagram indicating a manufacturing process tracking information which is an example of the method for displaying inspection result of the fatal/non-fatal condition determination with the external appearance inspection apparatus of FIG. 1.

FIG. 8 is a process tracking diagram indicating manufacturing process tracking information which is an example of the method for displaying inspection result of the fatal/non-fatal condition determination with the external appearance inspection apparatus of FIG. 1.

Figure 9:
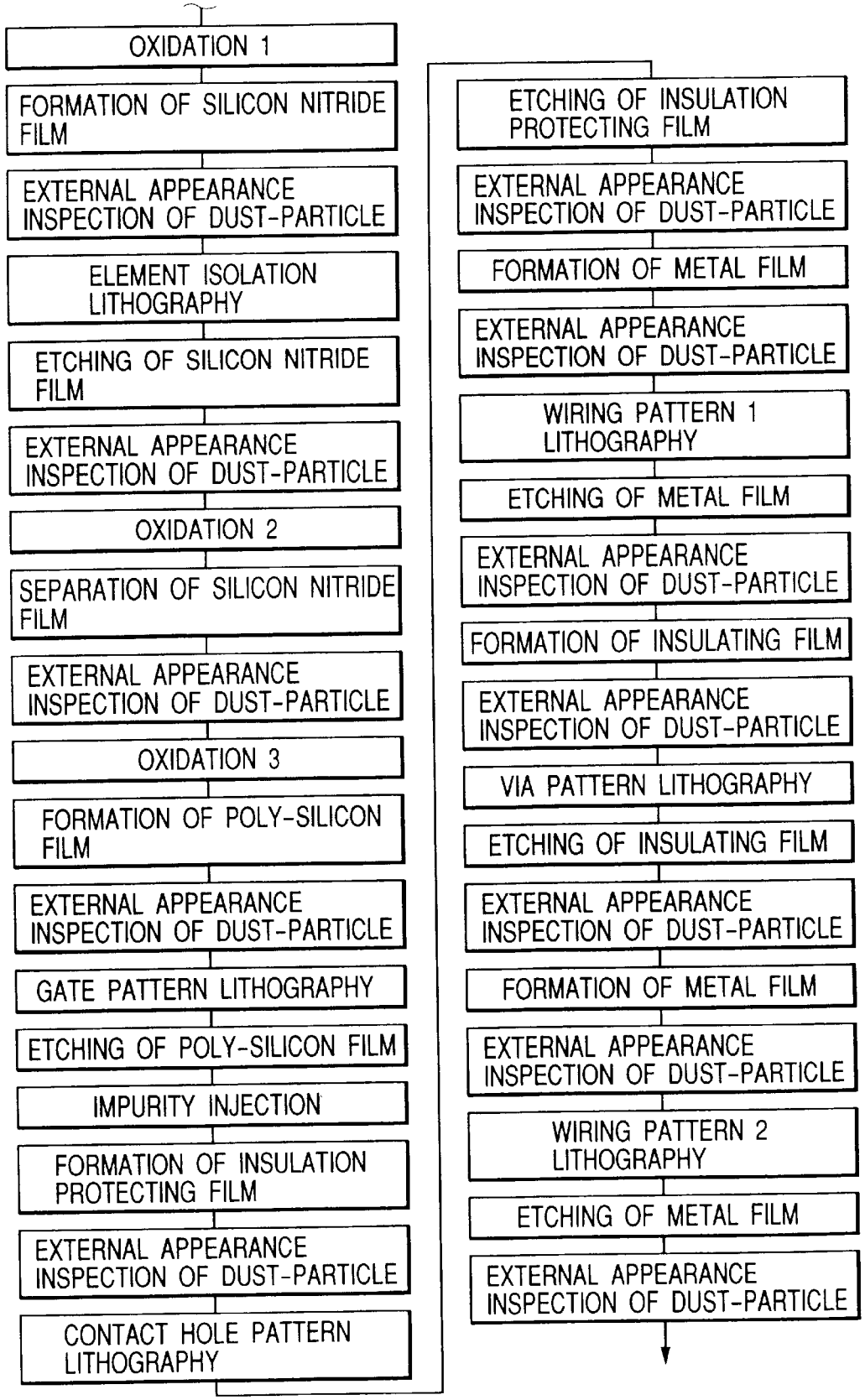
FIG. 9 is a process flow diagram indicating an example of the main preprocess of the semiconductor device manufacturing process in which the inspection is conducted with the external appearance inspection apparatus of FIG. 1.

FIG. 9 is a process flow diagram indicating an example of the main preprocess of the semiconductor device manufacturing process in which the inspection is conducted with the external appearance inspection apparatus of FIG. 1.

The external appearance inspection apparatus illustrated in FIG. 1 of the preferred embodiment 1 detects dust-particle/fault 8 adhered (generated) on a semiconductor wafer 2 as illustrated in FIG. 3 and also obtains the position in the form of coordinate and also determines the dust-particle/fault 8 as the fatal or non-fatale dust-particle/fault depending on the fact that the dust-particle/fault 8 exists on the pattern 10 illustrated in FIG. 4(a) or not.

When the dust-particle/fault 8 exists on the pattern 10, this dust-particle/fault is defined as the fatal dust-particles/fault and when it exists in the outside of the pattern, it is defined as the non-fatal dust-particle/fault. Moreover, when such dust-particle/fault is located in the area near the pattern 10, it is defined as a candidate of fatal dust-particles/fault.

The external appearance inspection apparatus of FIG. 1 is of a dark field system apparatus and its main portion is composed of a stage 1 which can move freely in the X direction and Y direction, a laser 3 as the light source, a detector 4 for detecting the scattering/diffracting beam 3b of the laser beam 3a (optical beam), a detected image comparison processing system 5 fetching and comparing the signal from the inspection chip 6 assumed to include a dust-particle/fault 8 and the signal from the reference chip 7 assumed to include no dust-particle/fault 8 and a central control system 9 for controlling movement of the stage 1 and determining the fatal/non-fatal dust-particles/fault by obtaining the coordinate of dust-particles/fault 8.

Next, a method of manufacturing semiconductor device of the preferred embodiment of the present invention will be explained with reference to FIG. 1 to FIG. 9.

The method of manufacturing semiconductor device explained above detects dust-particle/fault 8 of a semiconductor wafer 2 using the external appearance apparatus of FIG. 1 in the inspection process of the semiconductor manufacturing process and determines the fatal/non-fatal dust-particle/fault.

First, when the inspection chip 6 of the semiconductor wafer 2 on the stage 1 is irradiated with the laser beam 3a (optical beam) from the laser 3, the laser beam 3a is reflected at the semiconductor wafer 2 to become the scattering/diffracting beam 3b. Thereby, the signal from the pattern 10 and the signal from dust-particle/fault 8 are detected in the detector 4.

Moreover, the image signal (inspection chip information) of the inspection chip 6 fetched in the detector 4 is then transmitted to a detected image comparison processing system 5.

In this detected image comparison processing system 5, the image signal from the inspection chip 6 (inspection chip information) is compared with the image signal from the reference chip 7 (reference chip information) (step S1 of FIG. 5). Namely, a difference between the image signal of the inspection chip 6 and the image signal stored previously of the reference chip 7 located adjacent to the inspection chip 6 is extracted. The dust-particle/fault 8 and pattern 10 are determined respectively depending on the fact that this difference is larger than or smaller than the maximum value Thnmax (not illustrated) of the difference value of the pattern 10.

Thereafter, the dust-particle/fault 8 is extracted depending on the determination result of the detected image comparison processing system 5 (step S2).

While this comparison process is executed for entire part of the semiconductor wafer 2 by moving the stage 1 when the stage controller is controlled with the central control system 9.

As a result, position of dust-particle/fault 8 on the semiconductor wafer 2 can be identified (step S3) and the chip matrix 11 for identifying the chip and chip coordinate 12 in the XY directions which is the orthogonal coordinate from the predetermined reference origin in the chip regarding such position are stored in the inspection apparatus memory system 13 illustrated in FIG. 2 provided in the external appearance apparatus.

Thereby, the coordinate of a dust-particle/fault 8 on the semiconductor wafer 2 can be obtained (step S4).

Here, a size of dust-particle/fault 8 is also calculated using the image comparison process.

The information about position and size of dust-particles/fault 8 is called the dust-particle/fault information.

On the other hand, the design pattern data corresponding to respective coordinate data stored in the inspection apparatus memory system 13 is extracted from the design pattern data processing system 14 of FIG. 2 and it is then transmitted to the central control system 9.

In the central control system 9, calculation is conducted using the dust-particle/fault information such as position coordinate and size of dust-particle/fault 8 in order to determine that the dust-particle/fault 8 is located on a circuit or a wiring pattern (these are called as a pattern 10) or at the outside the pattern.

In this case, as is illustrated in FIG. 4(a), the matching between the pattern 10 by the design pattern data and position coordinate of dust-particle/fault 8 depending on the dust-particles/fault information is conducted (step S5) and thereby whether dust-particle/fault 8 is located on the pattern or at the outside the pattern (step S6).

Here, the design pattern data is compared with the position coordinate of dust-particle/fault 8 and size thereof. When the dust-particle/fault is determined to exist on the pattern, such dust-particle/fault is determined as the fatal dust-particle/fault and it is defined as the fatal dust-particles/fault 15 illustrated in FIG. 5 and is then recorded and stored in the inspection apparatus memory system 13.

Moreover, when the dust-particle/fault is located at the outside the pattern, as illustrated in FIG. 4(b), the design pattern data is expanded with the predetermined expansion rate and thereafter the result is compared with the coordinate of dust-particle/fault 8. Finally, when the dust-particle/fault 8 is determined to exist on the pattern, this dust-particles/fault 8 is determined as the fatal dust-particle/fault 16 and it is then recorded and stored in the inspection apparatus memory system 13.

The dust-particle/fault 8 other than the fatal dust-particles/fault 16 is determined as non-fatal dust-particles/fault 17 and it is then recorded and stored in the inspection apparatus memory system 13.

Accordingly, in the fatal/non-fatal dust-particle/fault determination, when the dust-particle/fault is located outside the pattern as illustrated in FIG. 5, this dust-particle/fault becomes the non-fatal dust-particle/fault 17 and when it is located on the pattern, it is classified as the dust-particles/fault to determine the fatal dust-particle/fault 15 and candidate of fatal dust-particle/fault 16.

Thereafter, fatal, candidate of fatal or non-fatal dust-particle/fault is recorded to a chip including the dust-particle/fault 8 determined as the fatal, candidate of fatal or non-fatal dust-particle/fault and such record is then stored.

Moreover, the assumed maximum yield and the assumed minimum yield of the manufacturing process of the semiconductor wafer 2 used in this inspection are respectively calculated respectively using the number of non-fatal chips and the number of non-fatal chips (step S7).

In addition, the external appearance inspection apparatus of FIG. 1 displays, with the inspection apparatus display system 18 of FIG. 2 provided therein, the estimated maximum yield and estimated minimum yield of the semiconductor wafer 2 used for inspection, various chip map information pieces of FIG. 6, various time series transition information pieces of FIG. 7 and manufacturing process tracking information of FIG. 8.

Here, FIG. 6 illustrates the positions of the dust-particles/fault 8 of the semiconductor wafer 2, respectively indicating, from the left side, the chip map information of all dust-particles/faults 8, chip map information of dust-particles/fault 8 corresponding to the fatal one, chip map information of dust-particle/fault 8 corresponding to the candidate thereof, chip map information corresponding to non-fatal one and chip map information replaced to defective/candidate of defective chip.

Moreover, FIG. 7 indicates the data of a particular inspection date among the times series transition information indicating that the number of dust-particles/faults 8 in a plurality of semiconductor wafers 2 for every inspection date. In FIG. 7, number of all dust-particles/fault 8, number of dust-particles/faults 8 corresponding to the fatal one, number of dust-particles/faults 8 corresponding to the fatal ones+candidate of fatal ones, number of dust-particles/faults 8 corresponding to non-fatal one and information replaced to the process yield are respectively indicated from the left side.

FIG. 8 illustrates the number of dust-particles/faults 8 as the manufacturing process tracking information in each manufacturing process (inspection process) for the manufacturing process in which the wafer process is conducted in the semiconductor device manufacturing process. In FIG. 7, the number of all dust-particles/fault 8, number of dust-particles/faults 8 corresponding to the fatal one, number of dust-particles/faults 8 corresponding to the fatal ones+candidate of fatal ones, number of dust-particles/faults 8 corresponding to non-fatal one and information replaced to the process yield are respectively indicated from the left side and the manufacturing process having the result and cause relationship for the result of determination for fatal/nonfatal dust-particle/fault can be tracked from the respective information pieces.

In regard to the displays of inspection results of each of the information illustrated in FIG. 6, FIG. 7 and FIG. 8, it is enough when at least apiece of information maybe displayed, or any two kinds among three kinds of information pieces may be displayed and three kinds of information pieces may be displayed.

Moreover, the external appearance inspection apparatus of this embodiment 1 can transmits, together with the identification code of semiconductor wafer 2 and inspection process, the data of chip matrix 11 for identifying chip including dust-particle/fault 8 as the inspection result, orthogonal coordinate from the predetermined reference origin in the chip and fatal/non-fatal determination result to the analyzing apparatus 50 as the external apparatus with the inspection apparatus communication system 19 provided at the central control system 9.

Here, as illustrated in FIG. 2, the analyzing apparatus 50 comprises an analyzing apparatus communication system 51, an analyzing apparatus memory system 52, an analyzing station 53, a distribution management station 54 and an analyzing apparatus display system 55. The analyzing apparatus communication system 52 is electrically connected with the inspection apparatus communication system 19 of the external appearance inspection apparatus for the purpose of information transmission.

Therefore, various information pieces transmitted from the inspection apparatus communication system 19 of the external appearance inspection apparatus are stored in the analyzing apparatus memory system 52 of the analyzing apparatus 50.

Moreover, the analyzing station 53 can display, with the analyzing apparatus display system 55 connected thereto, the same contents as that displayed with the inspection apparatus display system 18 of the external appearance apparatus, namely the estimated maximum yield and estimated minimum yield of the semiconductor wafer 2 used for inspection, various chip map information pieces of FIG. 6, various times series transition information pieces of FIG. 7 and manufacturing process tracking information of FIG. 8.

In addition, the analyzing station 53 estimates the yield in the electrical circuit operation inspection process from the process yield in each inspection process illustrated in FIG. 9 of the semiconductor wafer 2 and then stores this data in the analyzing apparatus memory system 52.

The various chip map information pieces of FIG. 6, various time series transition information pieces of FIG. 7 and manufacturing process tracking information of FIG. 8 may be displayed in any one of the inspection apparatus display system 18 and analyzing apparatus display system 55 or may be displayed in both display systems.

Moreover, the distribution management station 54 instructs, when the process yield in the inspection process in which the predetermined process is conducted to the semiconductor wafer 2 is identical to the specified value or less, that the relevant semiconductor wafer 2 should be sent to the detail inspection process using an electronic microscope.

In addition, the distribution management station 54 receives, in the inspection process of the semiconductor manufacturing process, the information of the fatal/non-fatal rate of the product in the manufacturing process inspected by the external appearance inspection apparatus with the inspection method and estimates, from this information, the yield of the relevant product existing in the inspection process and then analyzes deviation for the estimated amount of product to be delivered in order to control the amount of production of the relevant product.

The distribution management station 54 also instructs to increase the sampling inspection rate in the relevant inspection process, for example, to 25% from 10% as the initial setting value. Moreover, when the condition higher than the specified value is continued longer than the preset period in the process yield in the inspection process of the semiconductor wafer 2, the distribution management station 54 instructs to decrease the sampling inspection rate in the relevant inspection process, for example, to 5% from 10% of the initial setting value.

Therefore, the analyzing apparatus 50 is capable of controlling the inspection rate of the relevant type of product existing within the process by receiving the fatal/non-fatal rate of the product in the course of manufacturing process inspected with the inspection method in above inspection process.

Moreover, the distribution management station 54 issues, when the estimated yield is lower than that at the beginning, an instruct to increase the amount of product to be manufactured, while issues, when the estimated yield is higher than that at the beginning, an instruction to decrease the amount of product to be manufactured.

Therefore, efficiency of detail inspection maybe improved and shortening of manufacturing period of the product as a whole may be realized, depending on various instructions of the distribution management station 54 of the analyzing apparatus 50 which has received the result of destination for the fatal/non-fatal condition.

In addition, the inspection rate of the process reducing the yield of the product as a whole can be increased and thereby it can make much contribution to reduction of manufacturing cost by quickly finding a fault and providing a measure for this fault and it is also possible to realize management for delivery date of custom product and reduce the amount of defective stock.

Namely, according to the semiconductor device manufacturing method as the first embodiment of the present invention, the information about the result of determination for fatal/non-fatal fault of dust-particle/fault 8 is transmitted to the distribution management station 54 in the analyzing apparatus 50 (external apparatus) connected electrically to the external appearance inspection apparatus which has made such decision, the distribution management station 54 makes management for distribution of semiconductor manufacturing process based on the destination result information and thereafter instructs the adequate process in order to reflect the result of fatal/non-fatal condition by the external appearance inspection apparatus on the process in each manufacturing process.

(Embodiment 2)

Figure 10:
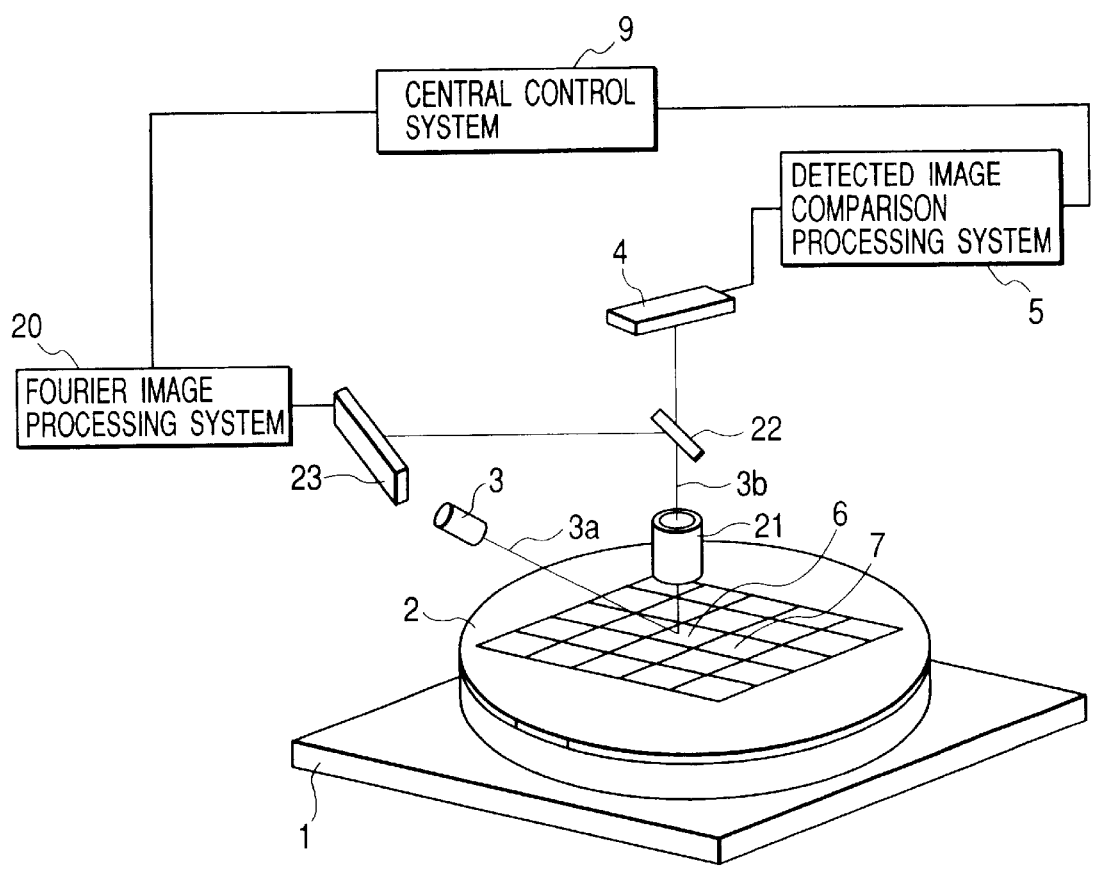
FIG. 10 is a perspective view illustrating an example of structure of the essential portion of the external appearance inspection apparatus of the embodiment 2 used in the inspection process of the semiconductor device manufacturing method of the present invention.

FIG. 10 is a perspective view illustrating an example of stricture of the essential portion of the external appearance inspection apparatus of the embodiment 2 used in the inspection process of the semiconductor device manufacturing method of the present invention.

Figure 11:
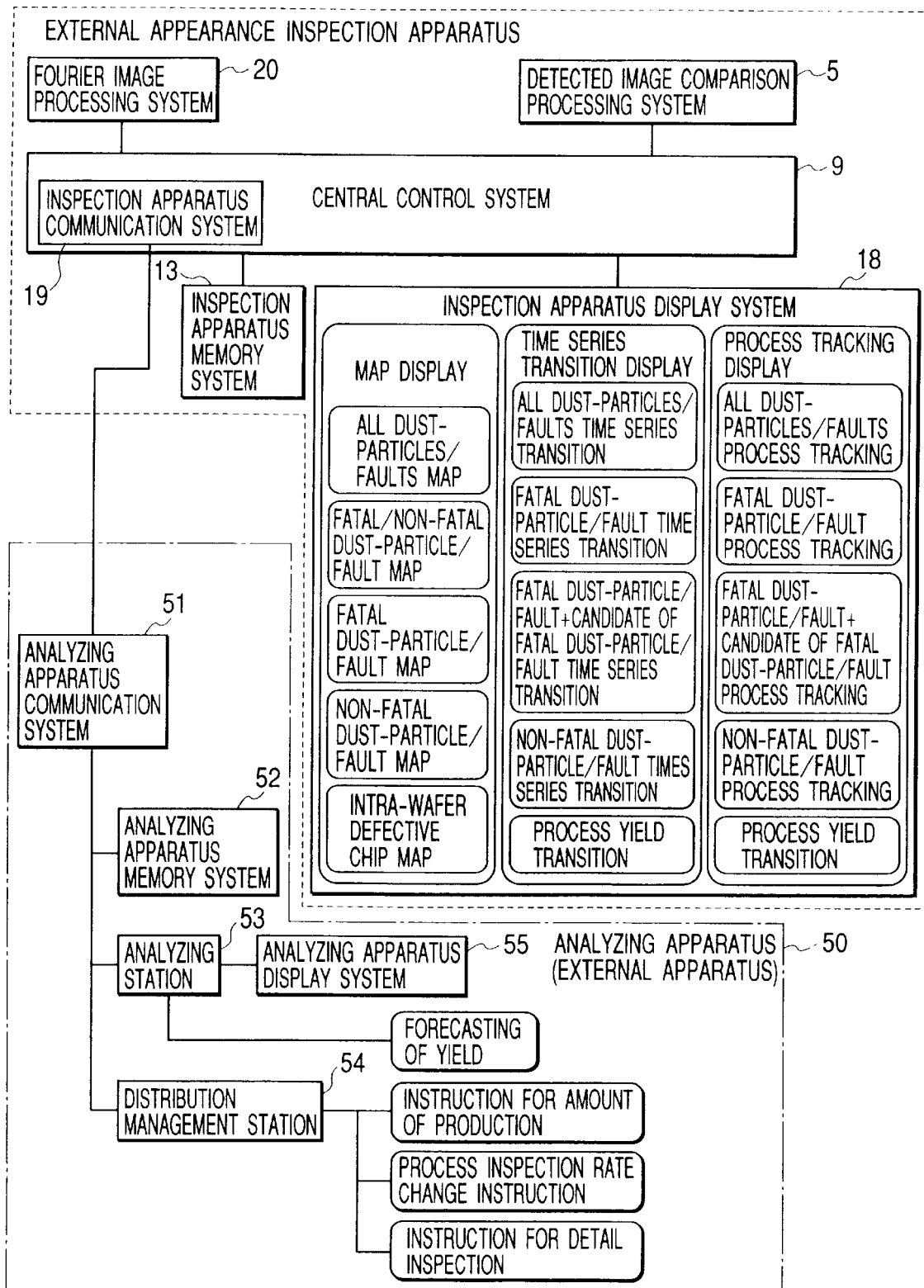
FIG. 11 is a block diagram illustrating respective examples of structures of the essential portions of external appearance inspection apparatus and external apparatus connected thereto of the embodiment 2 of FIG. 10.

FIG. 11 is a block diagram illustrating respective examples of structures of the essential portions of external appearance inspection apparatus and external apparatus connected thereto of the embodiment 2 of FIG. 10.

FIGS. 12(*a*), 12(*b*) are diagrams illustrating an example of the fatal/non-fatal condition determination method used in the inspection process of the semiconductor device manufacturing method in the embodiment 2 of the present invention, including a pattern diagram of reference chip (a) and Fourier image diagram of (a) (b).

Figure 13:
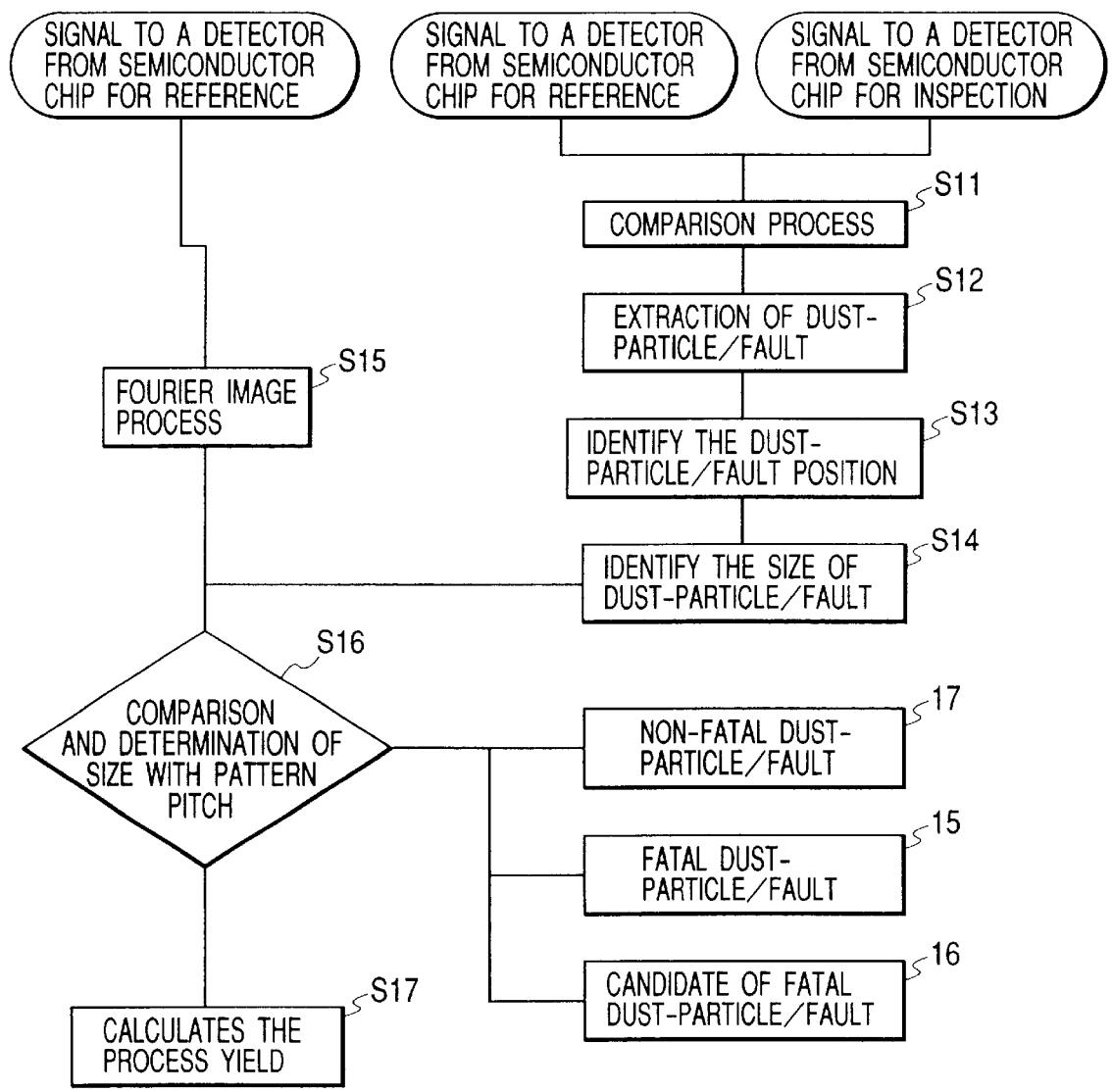
FIG. 13 is a flow diagram of inspection sequence indicating an example of the inspection sequence executed in the inspection process of the semiconductor manufacturing method of the embodiment 2 of the present invention.

FIG. 13 is a flow diagram of inspection sequence indicating an example of the inspection sequence executed in the inspection process of the semiconductor manufacturing method of the embodiment 2 of the present invention.

In the semiconductor manufacturing method of the embodiment 2 of the present invention, the fatal/non-fatal condition of dust-particle/fault 8 is determined using the external appearance inspection apparatus which is almost similar to that used in the semiconductor device manufacturing process of the embodiment 1.

Here, the structure of the external appearance inspection apparatus of the embodiment 2 of the present invention illustrated in FIG. 10 will be explained mainly in the difference from that illustrated in FIG. 1 of the embodiment 1.

The external appearance inspection apparatus of the embodiment 2 illustrated in FIG. 10 is a dark field type having the structure that the Fourier picture processing system 20 is added to the external appearance inspection apparatus of the embodiment 1 illustrated in FIG. 1. Therefore, for the purpose of Fourier picture processing, a lens 21 and a half-mirror 22 are provided on the optical path of the scatting/diffracting light beam 3b from the semiconductor wafer 2 of the laser beam 3a and moreover a detector 23 for Fourier process is also provided to detect the scattering/diffracting beam 3b from the half-mirror 22.

Here, the other structure of the external appearance inspection apparatus of the embodiment 2 is similar to that of the external appearance inspection apparatus of the embodiment 1.

Next, the semiconductor device manufacturing method of the embodiment 2 will be explained.

Here, only the method for determining the fatal/non-fatal condition of dust-particle/fault 8 of the embodiment 2 will be explained and the other semiconductor device manufacturing method is similar to that of the embodiment 1 and therefore the same explanation is not repeated here.

First, when the inspection chip 6 (first area) at the main surface of the semiconductor wafer 2 on the stage 1 is irradiated with the laser beam 3a (optical beam) from the laser 3, the laser beam 3a is reflected at the semiconductor wafer 2 to become the scattering/diffracting beam 3b and passes the lens 21. Thereafter, this optical beam is divided to the scattering/diffracting beam 3b passing the half-mirror 22 and the scattering/diffracting beam 3b reflected from the half-mirror 22. The former is detected with the detector 4 and the latter is detected with the detector 23 for Fourier process.

Accordingly, the signal from the pattern 24 (refer to FIG. 12) and the signal from the dust-particle/fault 8 are detected with the detector 4 and detector 23 for Fourier process.

Thereafter, the image signal of inspection chip 6 fetched by the detector 4 (which is the inspection chip and is also first area information in the embodiment 2) is transmitted to the detected image processing system 5.

In this detected image comparison processing system 5, the image signal from the inspection chip 6 (chip information for inspection) and the image signal from the reference chip 7 (second area) (which is the reference chip information and is also the second area information in the embodiment 2) are compared with each other (step S11 of FIG. 13). Namely, a difference between the image signal of inspection chip 6 and the image signal of reference chip 7 adjacent to the inspection chip 6 being stored previously is obtained and when this difference value is larger than the maximum value Thnmax(not illustrated) of difference value of pattern 10, the dust-particles/fault 8 is defined as dust-particle and when such difference value is smaller than the maximum value Thnmax, the dust-particle/fault 8 is defined as pattern 10.

Thereafter, dust-particle/fault 8 is extracted depending on the determination result of the detected image comparison processing system 5 (step S12).

This comparison process is performed for the entire surface of the semiconductor wafer 2 by moving the stage 1 while controlling the stage controller with the central control system 9.

As a result, position of the dust-particle/fault 8 on the semiconductor wafer 2 can be identified (step S13) and the chip matrix 11 for identifying the chip and chip coordinate 12 in the XY directions which is the orthogonal coordinate from the predetermined reference origin in the chip regarding such position are stored, as illustrated in FIG. 13 of the embodiment 1, in the inspection apparatus storing system 13 provided in the external appearance inspection apparatus.

Thereby, the coordinate of dust-particle/fault 8 on the semiconductor wafer 2 can be obtained and a size of dust-particles/fault 8 can also be calculated using the image comparison process (step S14).

Information about position and size of such dust-particles/fault 8 is called the dust-particle/fault information.

Meanwhile, during the inspection, an image at the optical Fourier transform plane is simultaneously detected with the Fourier processing detector 23 via the half-mirror 22.

Thereafter, the Fourier image process (step S15) is executed in the Fourier image processing system 20.

That is, the pattern information (here, main the pattern pitch) from the reference chip 7 is obtained in the Fourier image processing system 20.

Figure 12B:
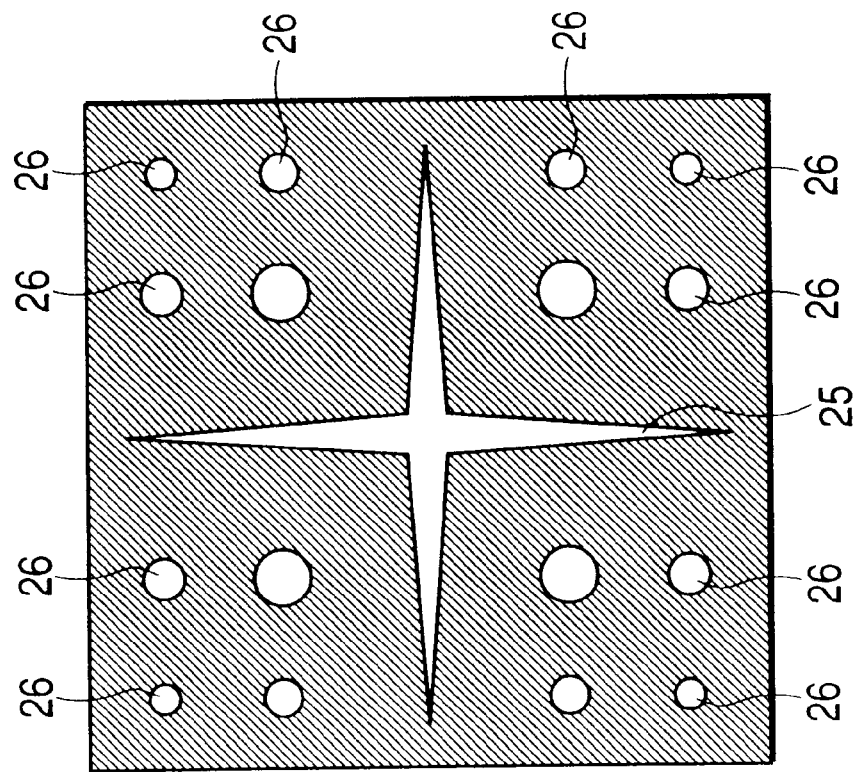
FIGS. 12(a), 12(b) are diagrams illustrating an example of the fatal/non-fatal condition determination method used in the inspection process of the semiconductor device manufacturing method in the embodiment 2 of the present invention, including a pattern diagram of reference chip (a) and Fourier image diagram of (a) (b).
Figure 12A:
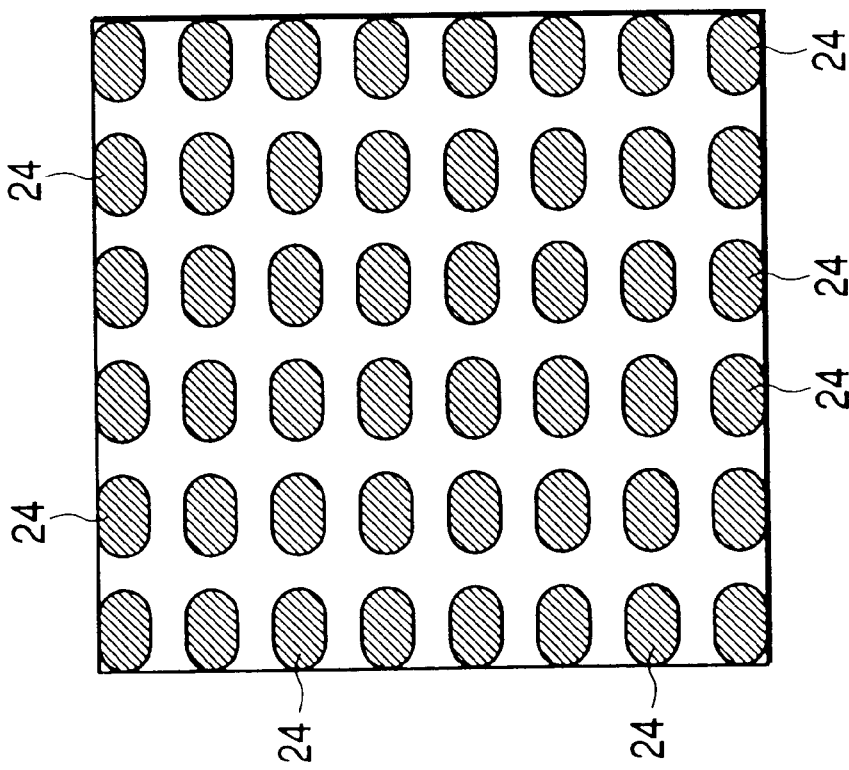

FIG. 12 illustrates the fatal/non-fatal condition determining method using the Fourier image process of the embodiment 2. As illustrated in FIG. 12(a), when a repeated pattern 24 such as memory LSI exists, its Fourier image changes to that illustrated in FIG. 12(b). When the $0^{th}$ order beam area 25 at the center is shielded, the characteristic Fourier image can be observed when the repeated pattern 24 exists and thereby the space frequency of the pattern 24 can be calculated from the interval of bright points 26 of the Fourier image and as a result, the pattern pitch can be calculated.

Subsequently, existence of pattern 24 based on the pattern information of the reference chip 7 for the position of dust-particle/fault 8 based on the dust-particle/fault information is determined. When it is determined that the pattern 24 exists at the position of the dust-particle/fault 8, the dust-particle/fault 8 is determined as the fatal dust-particle/fault and when it is determined that the pattern 24 is not located at the position of dust-particle/fault 8, such dust-particle/fault 8 is determined as the non-fatal dust-particles/fault.

In the embodiment 2, the pattern pitch is compared with a size of duct-particle/fault 8 (step S16), when it is determined that a size of dust-particle/fault 8 is 1.5 times or more the pattern pitch, such dust-particle/fault 8 is determined as the fatal dust-particle/fault and it is then stored in the inspection apparatus memory system 13 illustrated in FIG. 11 as the fatal dust-particle/fault 15 as illustrated in FIG. 13.

On the other hand, when a size of dust-particle/fault 8 is 0.5 times or less the pattern pitch, such dust-particle/fault 8 is defined as the non-fatal dust-particle/fault and it is then stored in the inspection apparatus memory system 13 as the non-fatal dust-particle/fault 17.

Moreover, when the size of dust-particle/fault 8 is an intermediate value of such magnifying factor and the shape is deviated to a large extent from the circular shape, such dust-particle/fault 8 is determined as a candidate of fatal dust-particle/fault and it is stored in the inspection apparatus memory system 13 as the candidate of fatal dust-particle/fault 16.

Thereafter, fatal condition, candidate of fatal condition or non-fatal condition is recorded to the chip including the dust-particle/fault 8 determined as the fatal, candidate or non-fatal dust-particle/fault and it is then stored in the inspection apparatus memory system 13.

Moreover, the estimated maximum yield and the estimated minimum yield of the relevant manufacturing process of the semiconductor wafer 2 used for this inspection are calculated using respectively the number of non-fatal chips and number of fatal chips (step S17).

The display type and method for the determination result of fatal/non-fatal conditions in the external appearance inspection apparatus of the embodiment 2, structure and function of the analyzing apparatus 50 (external apparatus) which is electrically connected to the external appearance inspection and the effect obtained from the semiconductor device manufacturing method of the embodiment 2 are identical to that of the first embodiment and the same explanation is not repeated here.

(Embodiment 3)

Figure 14:
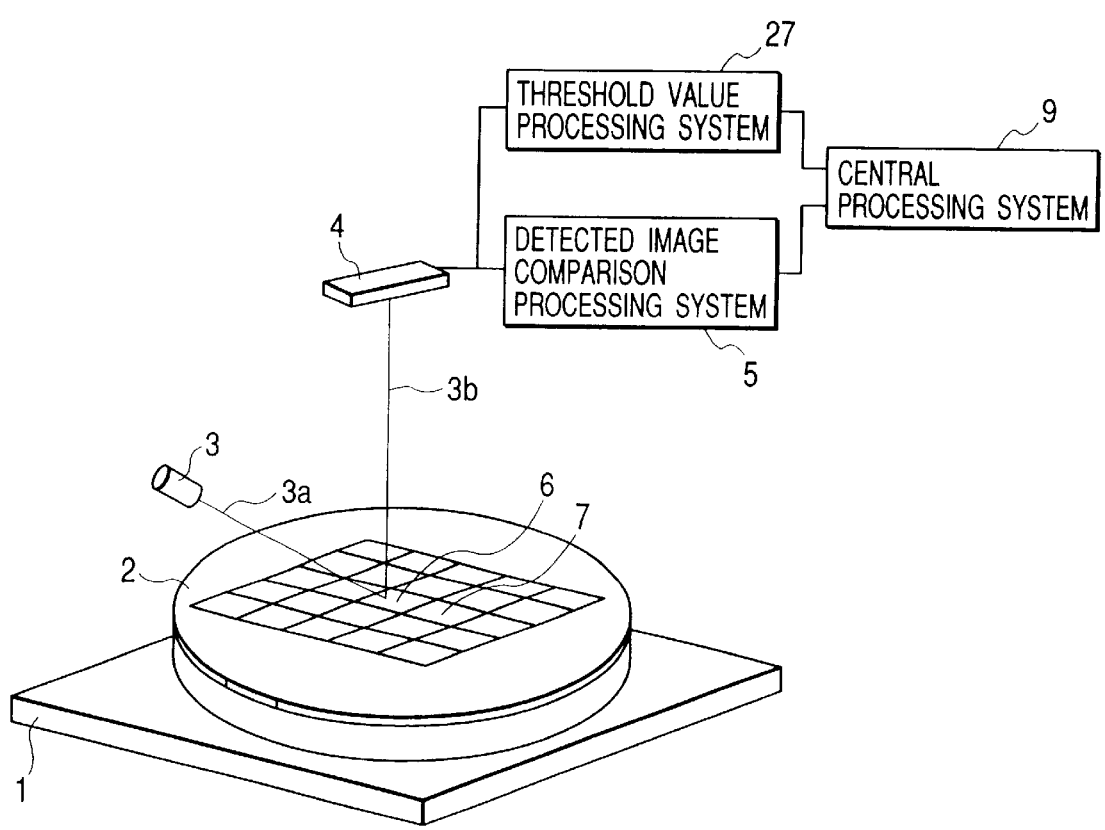
FIG. 14 is a perspective view illustrating an example of structure of the essential portion of the external appearance inspection apparatus of the embodiment 3 used in the inspection process of semiconductor device manufacturing method of the present invention.

FIG. 14 is a perspective view illustrating an example of structure of the essential portion of the external appearance inspection apparatus of the embodiment 3 used in the inspection process of semiconductor device manufacturing method of the present invention.

Figure 15:
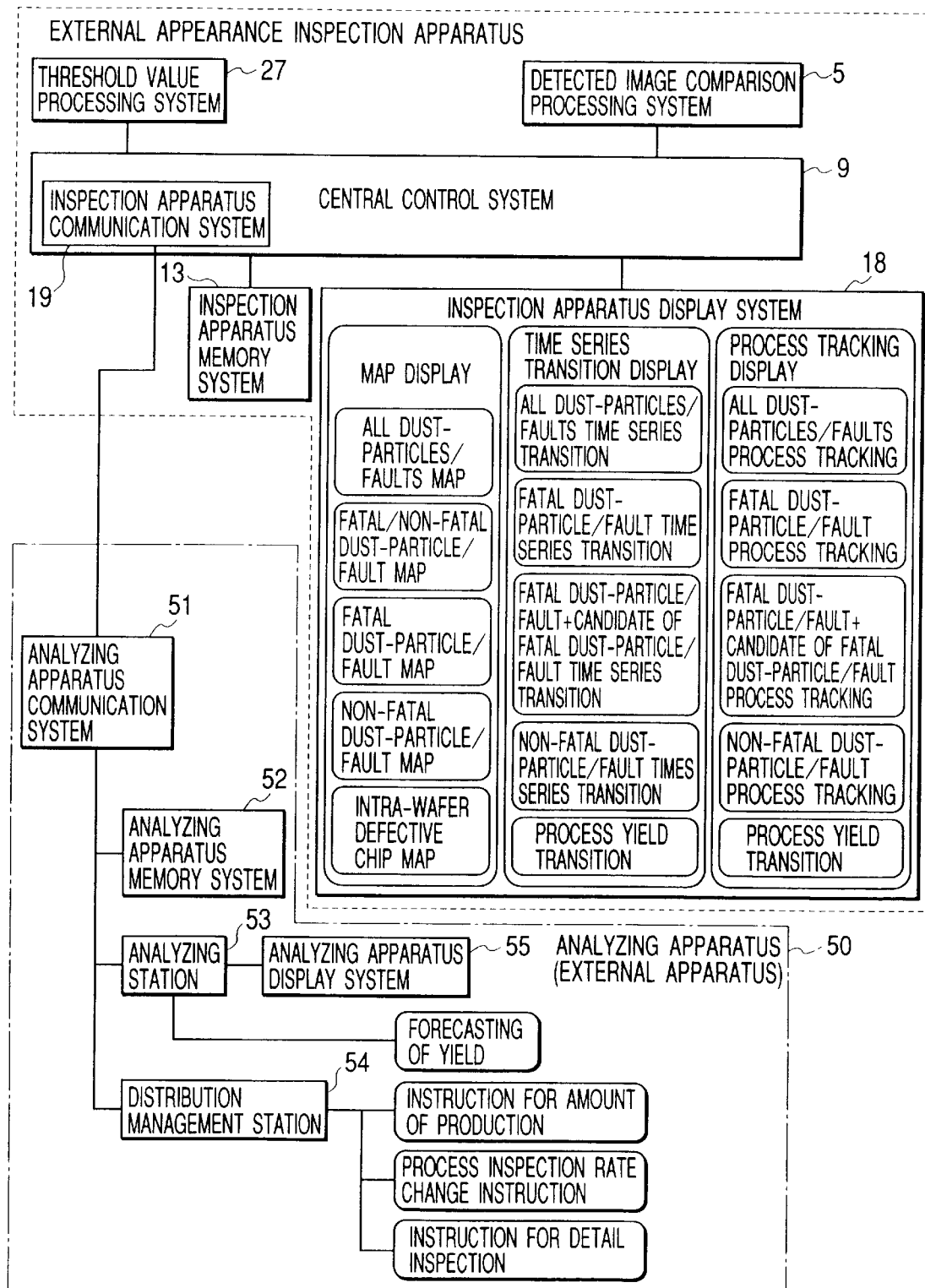
FIG. 15 is a block diagram illustrating examples of structures of the essential portions of the external appearance inspection apparatus of the embodiment 3 of FIG. 14 and the external apparatus connected thereto.

FIG. 15 is a block diagram illustrating examples of structures of the essential portions of the external appearance inspection apparatus of the embodiment 3 of FIG. 14 and the external apparatus connected thereto.

Figure 16A:
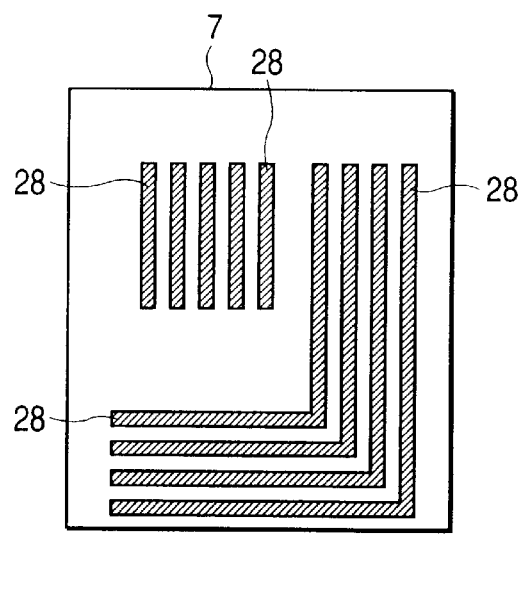
FIGS. 16(a), 16(b) are diagrams illustrating an example of the fatal/non-fatal condition determination method used in the inspection process of the semiconductor device manufacturing method of the embodiment 3 of the present invention, including pattern diagram of reference chip (a) and dark field detecting image of (a) (b).
Figure 16B:
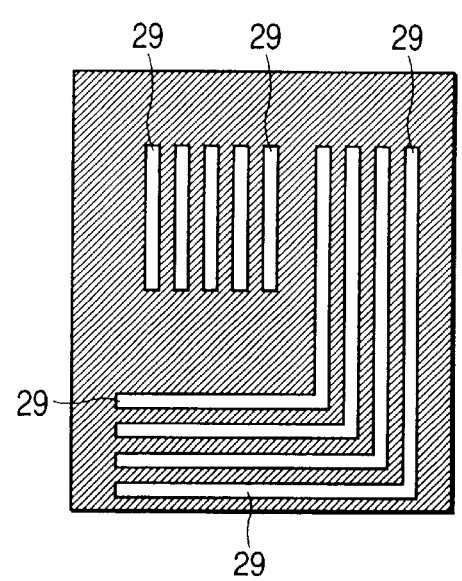

FIGS. 16(a), 16(b) are diagrams illustrating an example of the fatal/non-fatal condition determination method used in the inspection process of the semiconductor device manufacturing method of the embodiment 3 of the present invention, including pattern diagram of reference chip (a) and dark field detecting image of (a) (b).

Figure 17:
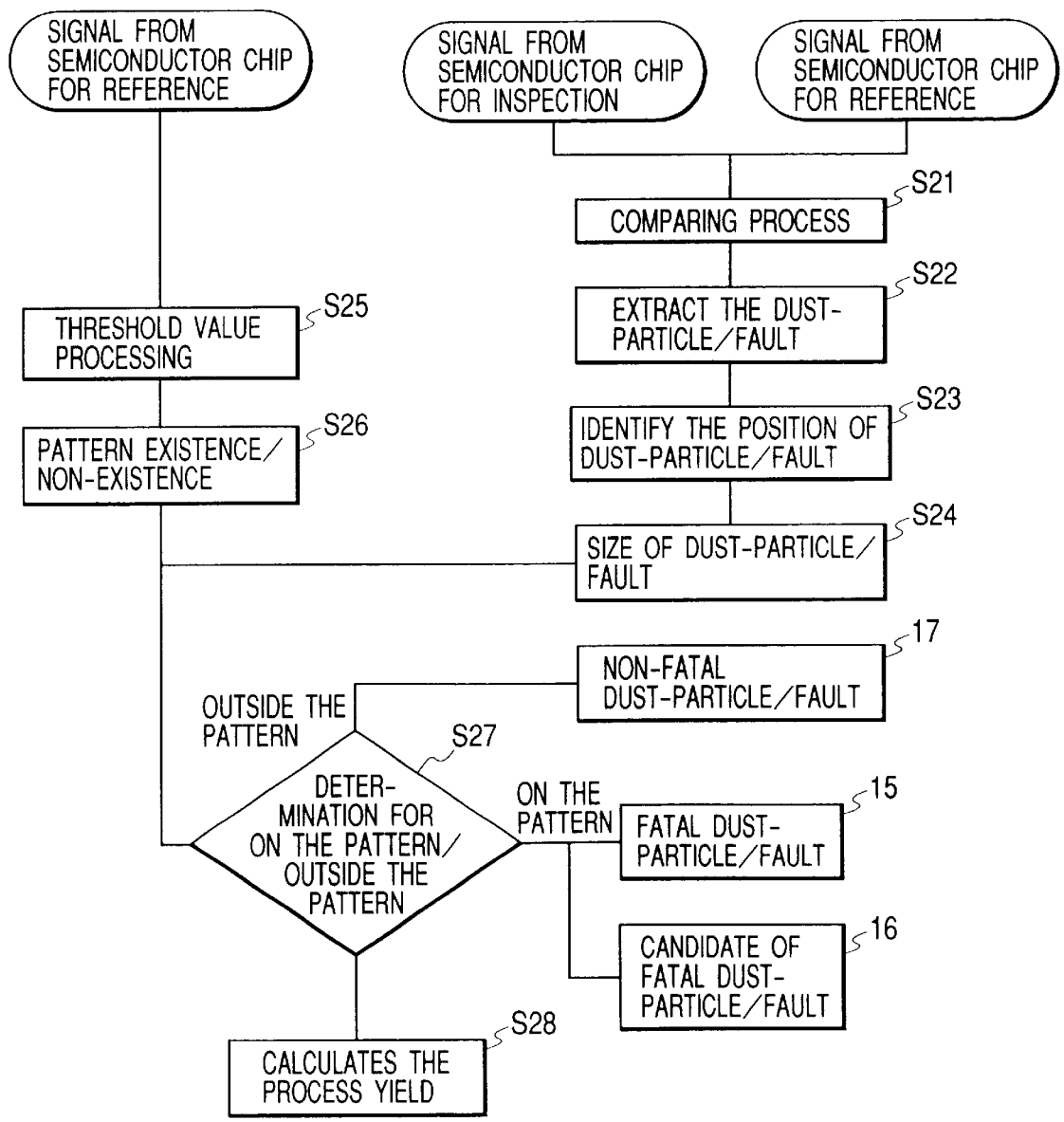
FIG. 17 is a flow diagram of inspection sequence indicating an example of the inspection sequence executed in the inspection process of semiconductor device manufacturing method of the embodiment 3 of the present invention.

FIG. 17 is a flow diagram of inspection sequence indicating an example of the inspection sequence executed in the inspection process of semiconductor device manufacturing method of the embodiment 3 of the present invention.

In the semiconductor device manufacturing method of the embodiment 3, determination for fatal/non-fatal condition of the dust-particle/fault 8 is made using the external appearance inspection apparatus which is almost similar to that used in the semiconductor device manufacturing process of the embodiment 1.

Here, the structure of the external appearance inspection apparatus of the embodiment 3 illustrated in FIG. 14 will be explained mainly in difference from the external appearance inspection apparatus illustrated in FIG. 1 of the embodiment 1.

The external appearance inspection apparatus of the embodiment 3 illustrated in FIG. 14 is a dark field type and has the structure that a threshold value processing system 27 is added to the external appearance inspection apparatus of the embodiment 1 illustrated in FIG. 1. In this structure, the threshold value process is executed to the pattern 28 of the reference chip 7 illustrated in FIG. 16(a) to determine the fatal/non-fatal condition.

The other structures of the external appearance inspection apparatus of the embodiment 3 are similar to that of the external appearance inspection apparatus of the embodiment 1 and therefore the same explanation not repeated here.

The semiconductor device manufacturing method of the embodiment 3 will be explained.

Here, only the fatal/non-fatal condition determining method of the dust-particle/fault 8 of the embodiment 3 will be explained and since the other semiconductor device manufacturing method is almost similar to that of the embodiment 1, the same explanation will not be repeated.

First, when the reference chip 6 of the semiconductor wafer 2 on the stage 1 is irradiated with the laser beam 3a (optical beam) from the laser 3, the laser beam 3a is reflected by the semiconductor wafer 2 to become the scattering/diffracting beam 3b and thereby the signal from pattern 28 and the signal from the dust-particle/fault 8 are detected with the detector 4.

Moreover, the image signal of the inspection chip 6 fetched with the detector 4 (inspection chip information) is transmitted to the detected image comparison processing system 5.

In this detected image comparison processing system 5, the image signal from the inspection chip 6 (inspection chip information) and the image signal from the reference chip 7 (reference chip information) are compared with each other (step S21 of FIG. 17). Namely, a difference between the image signal of inspection chip 6 and the image signal stored previously of the reference chip 7 adjacent to the inspection chip 6 is obtained and when this difference is larger than the maximum value Thnmax (not illustrated) of the difference value of the pattern 10, the dust-particle/fault 8 is determined as dust-particle and when such difference value is smaller than such maximum value Thnmax, the dust-particle/fault 8 is determined as the pattern 10.

Thereafter, the dust-particle/fault 8 is extracted depending on the determination result of the detected image comparison processing system 5 (step S22).

This comparison process is executed for the entire surface of the semiconductor wafer 2 by moving the stage while controlling the state controller with the central control system 9.

As a result, the position of dust-particle/fault on the semiconductor wafer 2 may be identified (step S23) and the chip matrix 11 for identifying the chip and the chip coordinate 12 in XY directions as the orthogonal coordinate from the predetermined reference origin in the chip are stored, for these positions, as illustrated in FIG. 3, to the inspection apparatus memory system 13 provided in the external appearance inspection apparatus.

Thereby, the coordinate on the semiconductor wafer 2 of the dust-particle/fault 8 may be obtained and moreover a size of such dust-particle/fault 8 can also be calculated using the image comparison processing process (step S24).

The information about position and size of these dust-particles/fault 8 is called the dust-particle/fault information.

Meanwhile, during such inspection, the dark field image pattern 29 (refer to FIG. 16(b)) of the pattern of reference chip 7 illustrated in FIG. 16(a) is simultaneously obtained.

Moreover, the threshold value process is executed in the threshold value processing system 27 (step S25) to recognize existence of the pattern 29 (step S26) in view of obtaining the pattern information of reference chip 7 and the pattern information of this pattern 29 is in turn transmitted to the central control system 9.

In the central control system 9, existence of the pattern 29 based on the pattern information of the reference chip 7 for the position of the dust-particle/fault 8 based on the dust-particle/fault information is determined using the dust-particle/fault information such as the position coordinate and size of dust-particle/fault 8 and the pattern information of the pattern 29 (step S27).

Here, when it is determined that the pattern 29 exists at the position of dust-particle/fault 8 (on the pattern), the dust-particle/fault 8 is defined as the fatal dust-particles/fault and it is recorded and stored in the inspection apparatus memory system 13 illustrated in FIG. 15 as the fatal dust-particle/fault 15 as illustrated in FIG. 17.

Moreover, the dust-particle/fault 8 exists at the outside of pattern 29, the pattern 29 is expanded with the predetermined expanding process. Thereafter, the expanding result is compared with the coordinate of the dust-particle/fault 8. When it is finally determined as it exists on the pattern, such dust-particle/fault 8 is determined as a candidate of fatal dust-particle/fault 16 and it is then recorded and stored in the inspection apparatus memory system 13.

The dust-particle/fault other than the candidate of dust-particle/fault 16 is determined as the non-fatal dust-particles/fault 17 and it is also recorded and stored in the inspection apparatus memory system 13.

Thereafter, the fatal condition, candidate of fatal condition and non-fatal condition are recorded on the chip including the dust-particle/fault 8 determined as the fatal, candidate of fatal or non-fatal dust-particle/fault and it is also stored in the inspection apparatus memory system 13.

In addition, the estimated maximum yield and estimate minimum yield of the relevant manufacturing process of the semiconductor wafer 2 used in this inspection are calculated respectively using the number of non-fatal chips and the number of fatal chips (step S28).

The display type and method for determination result of fatal/non-fatal condition in the external appearance inspection apparatus of the embodiment 3, the structure and function of the analyzing apparatus 50 (external apparatus) electrically connected to the external appearance apparatus and moreover the effect attained by the semiconductor device manufacturing method of the embodiment 3 are almost similar to that of the embodiment 1 and therefore the same explanation is not repeated here.

(Embodiment 4)

Figure 18:
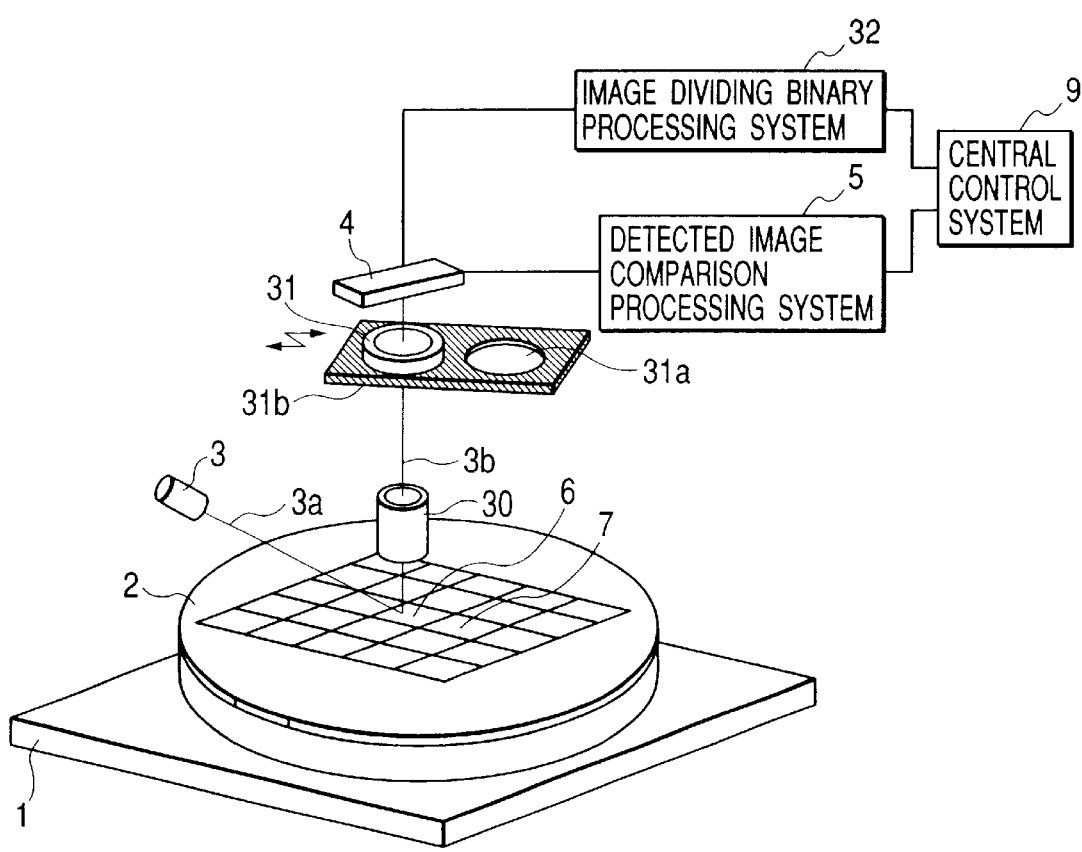
FIG. 18 is a perspective view illustrating an example of structure of the essential portion of the external appearance inspection apparatus of the embodiment 4 used in the inspection process of the semiconductor device manufacturing method of the present invention.

FIG. 18 is a perspective view illustrating an example of structure of the essential portion of the external appearance inspection apparatus of the embodiment 4 used in the inspection process of the semiconductor device manufacturing method of the present invention.

Figure 19:
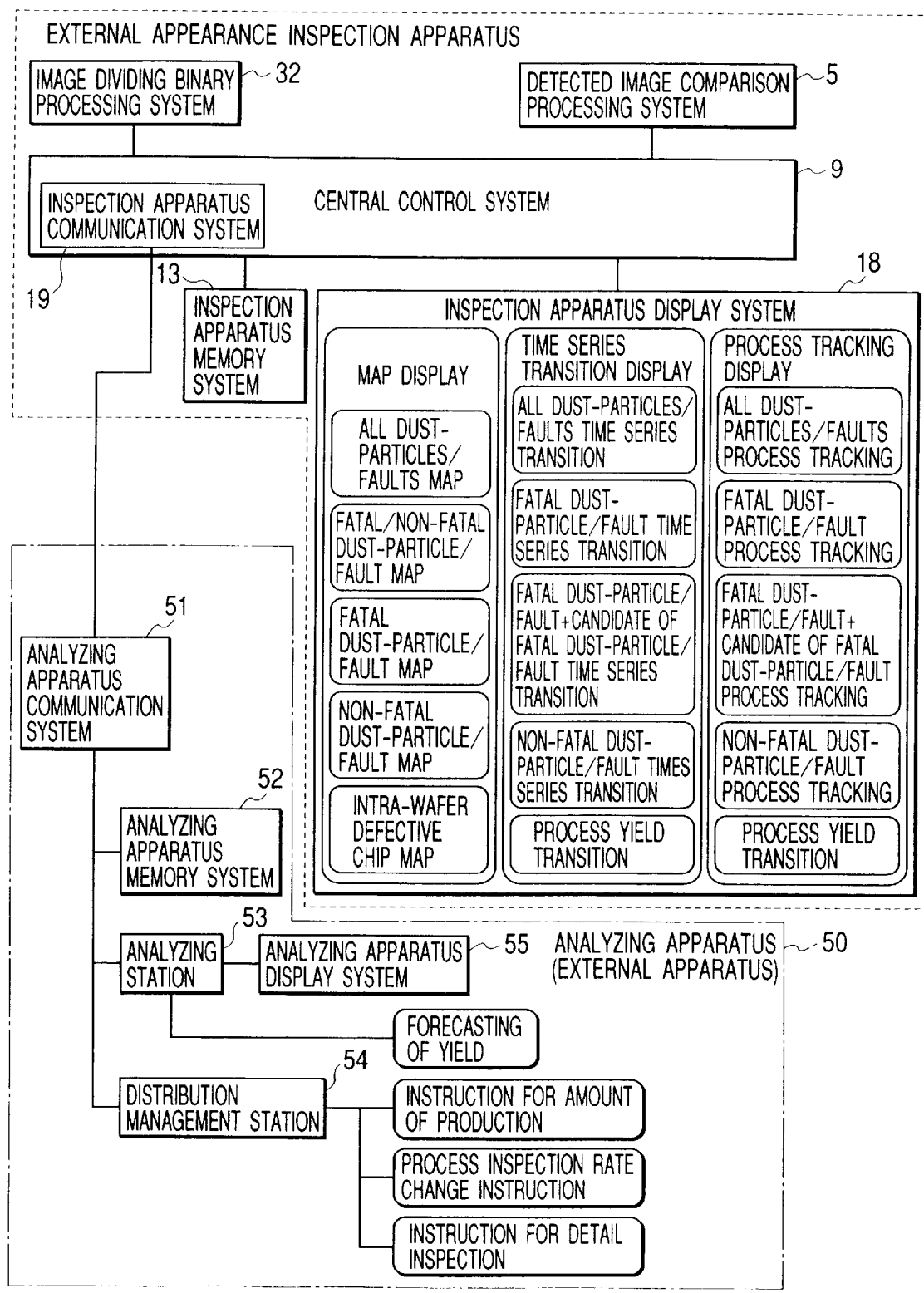
FIG. 19 is a block diagram illustrating an example of structure of the essential portion of the external appearance inspection apparatus of the embodiment 4 of FIG. 18 and the external apparatus connected thereto.

FIG. 19 is a block diagram illustrating an example of structure of the essential portion of the external appearance inspection apparatus of the embodiment 4 of FIG. 18 and the external apparatus connected thereto.

Figures 20A, 20B, 20C:
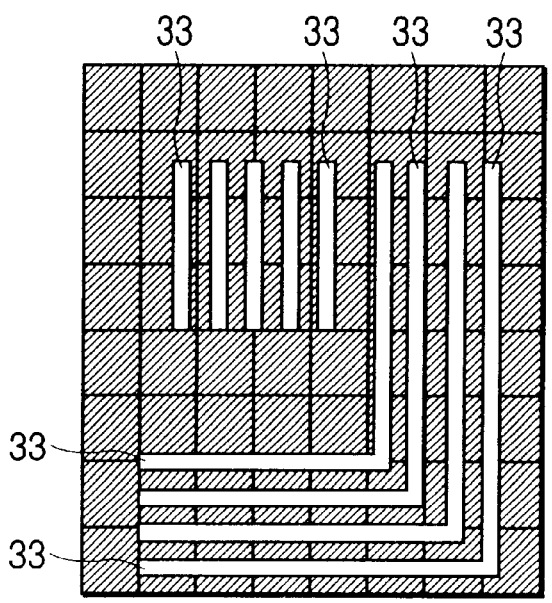
FIGS. 20(a), 20(b), 20(c) are diagrams illustrating examples of the fatal/non-fatal condition determination method used in the inspection process of the semiconductor device manufacturing method of the embodiment 4 of the present invention, including the dark field image diagram of pattern of reference chip (a), the 8×8 divided diagram through the binary process of (a)(b) and weighting diagram of (b)(c).

FIGS. 20(*a*), 20(*b*), 20(*c*) are diagrams illustrating examples of the fatal/non-fatal condition determination method used in the inspection process of the semiconductor device manufacturing method of the embodiment 4 of the present invention, including the dark field image diagram of pattern of reference chip (a), the 8×8 divided diagram through the binary process of (a)(b) and weighting diagram of (b)(c).

Figure 21:
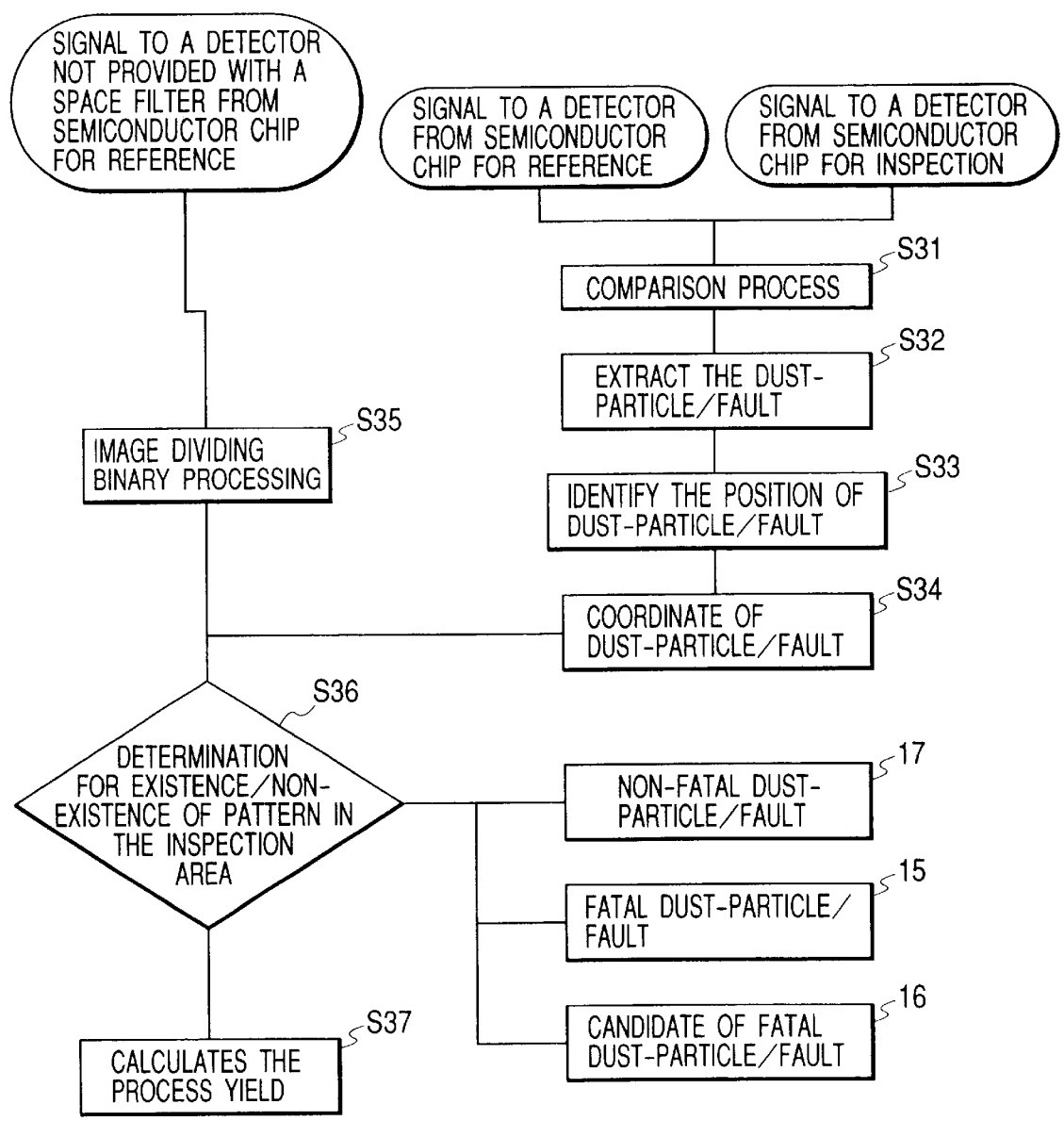
FIG. 21 is a flow diagram of inspection sequence illustrating an example of the inspection sequence executed in the inspection process of the semiconductor device manufacturing method in the embodiment 4 of the present invention.

FIG. 21 is a flow diagram of inspection sequence illustrating an example of the inspection sequence executed in the inspection process of the semiconductor device manufacturing method in the embodiment 4 of the present invention.

In the semiconductor device manufacturing method of the embodiment 4, the fatal/non-fatal condition of the dust-particles/fault 8 is determined using the external appearance inspection apparatus which is almost similar to the external appearance inspection apparatus used in the semiconductor device manufacturing process of the embodiment 1.

Here, the structure of the external appearance inspection apparatus of the embodiment 4 illustrated in FIG. 18 will be explained mainly in the difference from the external appearance inspection apparatus illustrated in FIG. 1 of the embodiment 1.

The external appearance inspection apparatus of the embodiment 4 illustrated in FIG. 18 is the dark field type apparatus and has the structure in which the image dividing binary processing system 32 is added to the external appearance inspection apparatus of the embodiment 1 illustrate in FIG. 1. Moreover, a lens 30 and a space filter (filter) 31 are provided on the optical path of the scattering/diffracting beam 3*b* from the semiconductor wafer 2 of the laser beam 3*a* and the fatal/non-fatal conditions are determined through the image dividing and binary processes.

The other structures of the external appearance inspection apparatus of the embodiment 4 are almost similar to that of the first embodiment and therefore the same explanation not repeated here.

Next, the semiconductor device manufacturing method of the embodiment 4 will be explained.

Here, only the fatal/non-fatal condition determining method of the dust-particle/fault 8 in the embodiment 4 will be explained and the other semiconductor device manufacturing method is similar to that of the embodiment 1 and therefore the same explanation is not repeated.

When the inspection chip 6 of semiconductor wafer 2 on the stage 1 is irradiated with the laser beam 3*a* (optical beam) from the laser 3, the laser beam 3*a* is reflected by the semiconductor wafer 2 to become the scatting/diffracting beam 3*b* and this scatting/diffracting beam 3*b* enters the detector 4 passing through the lens 30 and space filter 31. Thereby, the signal from the pattern 10 (refer to FIG. 4(*a*)) and the signal from the dust-particle/fault 8 are detected with the detector 4.

Moreover, the image signal (inspection chip information) of the inspection chip 6 fetched with the detector is then transmitted to the detected image comparison processing system 5.

In this detected image comparison processing system 5, the image signal from the inspection chip 6 (inspection chip information) and image signal from the reference chip 7 (reference chip information) are compared (step S31 of FIG. 21). Namely, a difference between the image signal of inspection chip 6 and the previously stored image signal of the reference chip 7 adjacent to the inspection chip 6 are obtained. When this difference is larger than the maximum value Thnmax (not illustrated) of the difference of pattern 10, the dust-particles/fault 8 is defined as the dust-particle and when such difference is smaller than the maximum value Thnmax, the dust-particle/fault 8 is defined as the pattern 10.

Thereafter, dust-particle/fault 8 is extracted depending on the determination result of the detected image comparison processing system 5 (step S32).

This comparison process is conducted for the entire surface of the semiconductor wafer 2 by moving the stage while controlling the stage controller with the central control system 9.

As a result, the position of dust-particle/fault 8 on the semiconductor wafer 2 can be identified (step S33) and the chip matrix 11 for identifying the chip and chip coordinate 12 of XY directions which is the predetermined orthogonal coordinate in the chip for the position are stored, as illustrated in FIG. 3, to the inspection apparatus memory system 13 provided in the external inspection apparatus.

Thereby, the coordinate of dust-particle/fault 8 on the semiconductor wafer 2 can be obtained and moreover a size of the dust-particle/fault 8 can also be calculated using the image comparison process (step S34).

The position and size information of the dust-particle/fault 8 is called the dust-particle/fault information.

After the step S34 illustrated in FIG. 21, the reference chip 7 is irradiated with the laser beam 3*a*, the scattering/diffracting beam 3*b* of the laser beam 3*a* is detected without passing through the space filter 31 to obtain the reference chip information. The reference chip information 2 obtained is subjected to the binary process to conduct the image dividing binary process in order to obtain the pattern information of the reference chip (step S35).

In this case, in the embodiment 4, the space filter 31 is moved to locate the opening 31*a* of the holder 31*b* of the space filter 31 on the optical path of the scatting/diffracting beam 3*b* so that the space filter 31 does not operate on the scatting/diffracting beam 3*b*.

Subsequently, the stage 1 is sequentially moved to the position where the pattern 33 of the reference chip 7 at the position of the detected dust-particle/fault 8 enters the field of the lens 30 and the dark field image illustrated in FIG. 20(*a*) can be obtained with the detector 4.

Moreover, after the dark field image is spatially divided into the small square areas, as illustrated in FIG. 20(*b*), for example, 64 (8×8) small square areas, and the binary process is conducted so that the predetermined threshold value process is performed in respective cells in which the brightness is previously determined and the bright area is defined as "1". Thereafter, the ratio (pattern information) which is compared with the case where the pattern 33 exists in all cells is obtained.

Here, as illustrated in FIG. 20(*b*), since "1" is obtained in the 31 areas among the 64 areas, the ratio (31/64) becomes almost 0.5.

The coefficient (for example, the binary process value is given the weight in each dividing position by sequentially multiplying "1", "2", "4" and "8" toward the center from the outer most circumference) depending on the dividing position for the binary process value of the respective cell obtained by space dividing illustrated in FIG. 20(*b*) is shown in FIG. 20(*c*).

Thereafter, the pattern information which is the ratio obtained in the image dividing binary processing system 32 is transmitted to the central control system 9.

In the central control system 9, existence of the pattern 33 based on the pattern information of the reference chip 7 for the position of dust-particle/fault 8 based on the dust-particles/fault information is determined using the dust-particles/fault information such as position coordinate and size of dust-particle/fault 8 and the pattern information obtained through the binary process (step S36).

Thereby, when the value of ratio based on the pattern information is, for example, 0.8 or higher (it is only a setting value and may be varied), the dust-particle/fault 8 is determined as the fatal dust-particle/fault and it is then recorded and stored, as illustrated in FIG. 21, to the inspection apparatus memory system 13 illustrated in FIG. 19 as the fatal dust-particle/fault 15.

Moreover, when the value of such ratio is, for example, 0.2 or less (it is only a setting value and may be varied), the dust-particle/fault 8 is determined as the non-fatal dust-particles/fault and it is then recorded and stored in the inspection apparatus memory system 13 as the non-fatale dust-particle/fault 17.

When the value of such ratio is in the range between 0.2 and 0.8, the dust-particle/fault 8 is determined as the candidate of fatal dust-particle/fault and it is then recorded and stored in the inspection apparatus memory system 13 as the candidate of fatal dust-particle/fault 16.

Thereafter, the fatal, candidate of fatal or non-fatal condition is recorded to the chip including the dust-particles/fault 8 determined as the fatal, candidate of fatal or non-fatal dust-particle/fault and it is then stored in the inspection apparatus memory system 13.

Moreover, the estimated maximum yield and estimated minimum yield of the relevant manufacturing process of the semiconductor wafer 2 used in this inspection are calculated respectively using the number of non-fatal chips and the number of fatal chips (step S37).

Display type and method of the determination result for fatal/non-fatal condition in the external appearance inspection apparatus of the embodiment 4, structure and function of the analyzing apparatus 50 (external apparatus) connected electrically to the external appearance inspection apparatus and moreover the effect of the semiconductor device manufacturing method of the embodiment 4 are similar to that of the embodiment 1. Therefore the same explanation is not repeated here.

(Embodiment 5)

Figure 22:
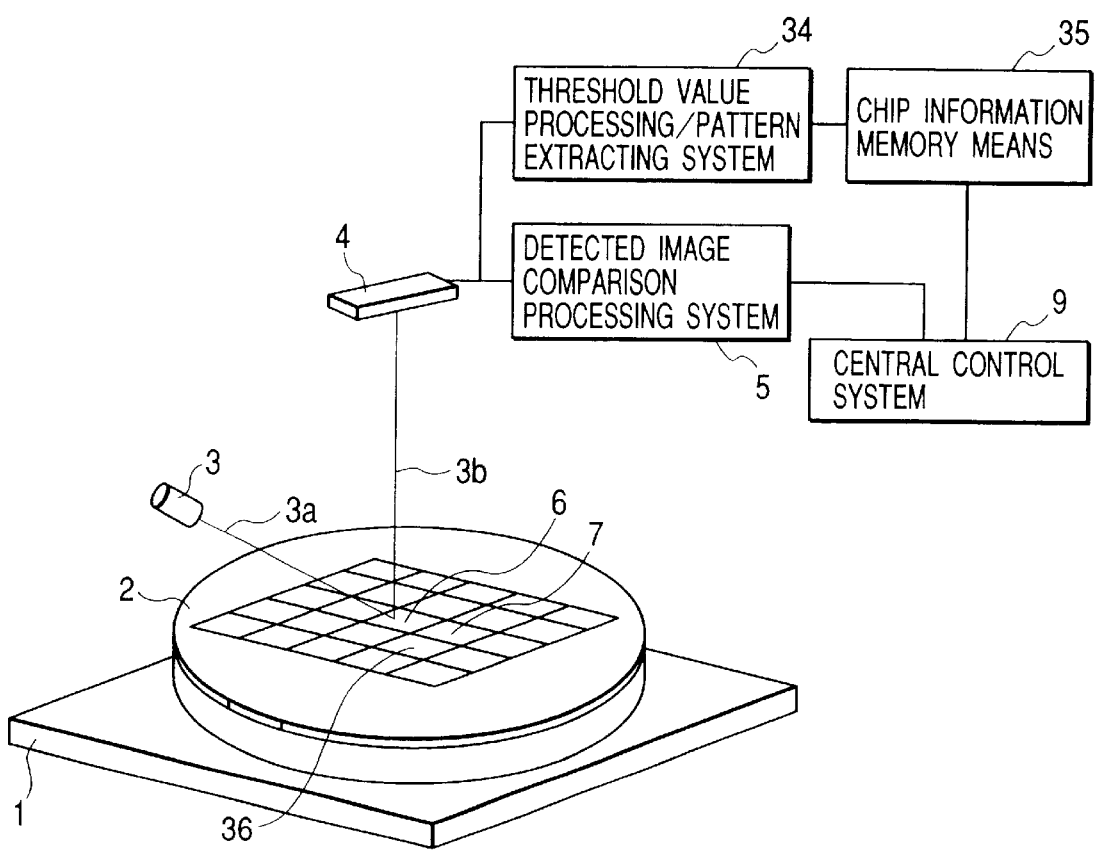
FIG. 22 is a perspective view illustrating an example of structure of the essential portion of the external appearance inspection apparatus of the embodiment 5 used in the inspection process of the semiconductor device manufacturing method of the present invention.

FIG. 22 is a perspective view illustrating an example of structure of the essential portion of the external appearance inspection apparatus of the embodiment 5 used in the inspection process of the semiconductor device manufacturing method of the present invention.

Figure 23:
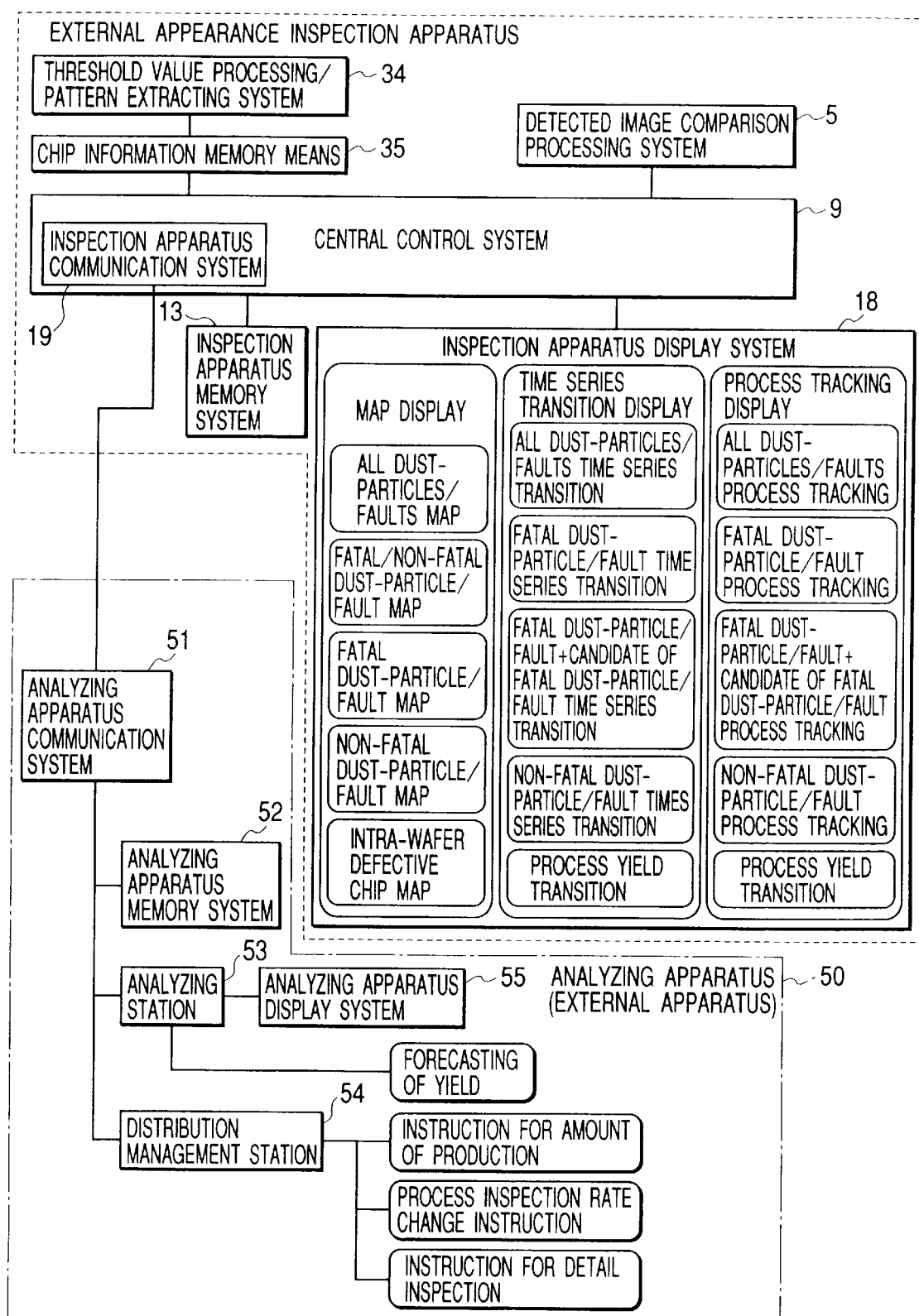
FIG. 23 is a block diagram illustrating an example of structure of the essential portion of the external appearance inspection apparatus of the embodiment 5 of FIG. 22 and the external apparatus connected thereto.

FIG. 23 is a block diagram illustrating an example of structure of the essential portion of the external appearance inspection apparatus of the embodiment 5 of FIG. 22 and the external apparatus connected thereto.

Figure 24:
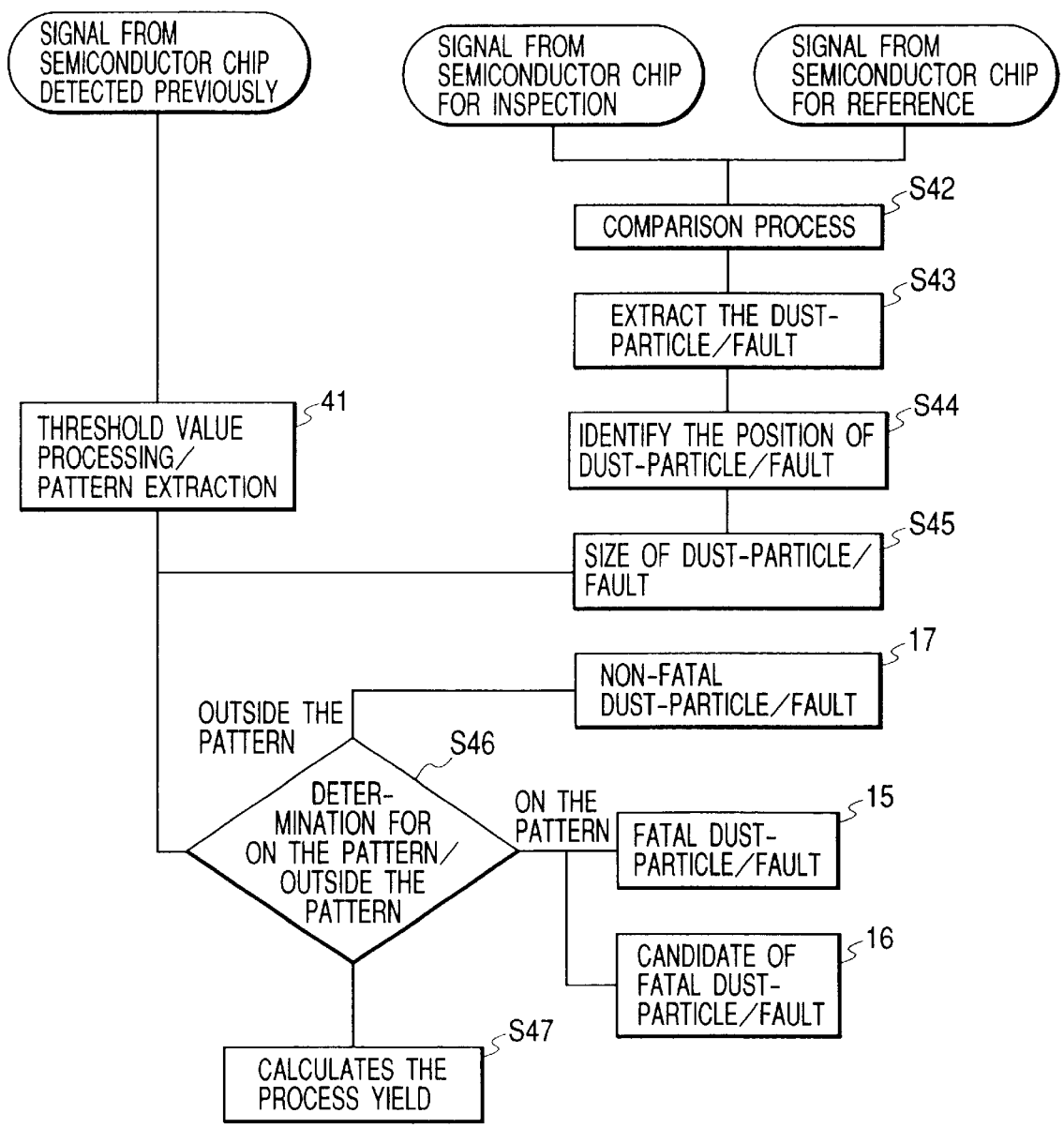
FIG. 24 is a flow diagram of inspection sequence illustrating an example of the inspection sequence executed in the inspection process of the semiconductor device manufacturing method of the embodiment 5 of the present invention.

FIG. 24 is a flow diagram of inspection sequence illustrating an example of the inspection sequence executed in the inspection process of the semiconductor device manufacturing method of the embodiment 5 of the present invention.

In the semiconductor device manufacturing method of the embodiment 5, the fatal/non-fatal condition of the dust-particles/fault 8 is determined using the external appearance inspection apparatus which is almost similar to that used in the semiconductor device manufacturing process of the embodiment 1.

Here, the structure of the external appearance inspection apparatus of the embodiment 5 illustrated in FIG. 22 will be explained mainly in the different from the external appearance inspection apparatus illustrated in FIG. 1 of the embodiment 1.

The external appearance inspection apparatus of the embodiment 5 illustrated in FIG. 22 is the dark field type and has the structure that the threshold value process/pattern extracting system 34 and the chip information memory means 35 are added to the external appearance inspection apparatus of the embodiment 1 of FIG. 1. In this structure, the data of pattern 10 (refer to FIG. 4) of the reference chip 7 is obtained before the inspection and it is then stored in the chip information memory means 35 and the fatal/non-fatal condition of dust-particle/fault is determined using this data at the time of inspection.

The other structure of the external appearance inspection apparatus of the embodiment 5 is similar to that of the external appearance inspection apparatus of the embodiment 1 and therefore the same explanation is not repeated here.

Next, the semiconductor device manufacturing method of the embodiment 5 will then be explained.

Here, only the fatal/non-fatal condition determining method for the dust-particle/fault 8 of the embodiment 5 will be explained and the other semiconductor device manufacturing method is similar to that of the embodiment 1 and therefore the same explanation will not be repeated.

First, before the inspection, one or a plurality of semiconductor chips 36 of the semiconductor wafer 2 supported with a stage 1 are irradiated with the laser beam 3*a* and the scatting/diffracting beam 3*b* of the laser beam 3*a* is detected and a dark field image thereof is obtained.

Subsequently, the chip information including pattern information on the semiconductor chip 36 from the dark field image and thereby the threshold value process/pattern extraction illustrated in the step S41 of FIG. 24 is conducted.

Namely, the dark field image is processed by the binary process to extract the pattern and thereby the chip information, namely pattern layout in the semiconductor chip 36 and its position in the chip are stored in the chip information memory means 35.

Thereafter, the inspection is performed.

First, when the inspection chip 6 of the semiconductor wafer 2 on the stage 1 is irradiated with the laser beam 3*a* (optical beam) from the laser 3, the laser beam 3*a* is reflected by the semiconductor wafer 2 to become the scattering/ diffracting beam 3b. Thereby, the signal from the pattern 10 and the signal from the dust-particle/fault 8 (refer to FIG. 3) are detected with the detector 4.

Moreover, the image signal of inspection chip 6 fetched by the detector 4 (inspection chip information) is transmitted to the detected image comparison processing system 5.

In this detected image comparison processing system 5, the image signal from the inspection chip 6 (inspection chip information) is compared with the image signal from the reference chip 7 (reference chip information) (step S42 of FIG. 24). Namely, a difference between the image signal of inspection chip 6 and the previously stored image signal of the reference chip 7 adjacent to the inspection chip 6 is obtained and when this difference is larger than the maximum value Thnmax (not illustrated) of the difference value of the pattern 10, the dust-particle/fault 8 is determined as dust-particle and when such difference is smaller than such maximum value Thnmax, the dust-particle/fault 8 is determined as pattern 10.

Thereafter, dust-particle/fault 8 is extracted depending on the result of determination of the detected image comparison processing system 5 (step S43).

This comparison process is performed for the entire surface of the semiconductor wafer 2 by moving the stage 1 while controlling the stage controller with the central control system 9.

As a result, position of dust-particle/fault 8 on the semiconductor wafer 2 can be identified (step S44) and the chip matrix 11 for identifying the chip and chip coordinate 12 of XY directions as the orthogonal coordinate from the predetermined reference origin in the chip for above position are stored as illustrated in FIG. 3 to the inspection apparatus memory system 13 provided in the external appearance inspection apparatus.

Thereby, the coordinate on the semiconductor wafer 2 of the dust-particle/fault 8 can be obtained and moreover a size of the dust-particle/fault 8 can also be calculated with the image comparison process (step S45).

The information about position and size of the dust-particles/fault 8 is called the dust-particle/fault information.

Thereafter, the central control system 9 extracts the chip information of semiconductor chip 36 stored previously in the chip information memory means 35 and determines existence of pattern 10 based on the pattern information of semiconductor chip 36 for the position of the dust-particle/fault 8 based on the dust-particle/fault information using the pattern information in the chip information (step S46).

Here, when it is determined that the pattern 10 exists (on the pattern) at the position of dust-particle/fault 8, the dust-particle/fault 8 is defined as the fatal dust particle/fault and it is then recorded and stored in the information apparatus memory system 13 illustrated in FIG. 23 as the fatal dust-particle/fault 15 as illustrated in FIG. 24.

Moreover, when it is determined that the dust-particles/fault 8 exists outside the pattern, the pattern 10 is previously expanded in the predetermined expanding rate and thereafter the result is compared with the coordinate of dust-particle/fault 8. When it is determined finally that the coordinate exists on the pattern, the relevant dust-particles/fault 8 is determined as the candidate of the fatal dust-particle/fault 16 and it is then recorded and stored in the inspection apparatus memory system 13.

The dust-particle/fault other than the candidate of fatal dust-particle/fault 16 is determined as the non-fatal dust-particles/fault 17 and it is then recorded and stored in the inspection apparatus memory system 13.

Thereafter, the fatal, candidate of fatal or non-fatal condition is recorded to the chip including the dust-particles/fault 8 determined as the fatal, candidate of fatal or non-fatal condition and it is then stored in the inspection apparatus memory system 13.

Moreover, the estimated maximum yield and estimated minimum yield of the manufacturing process of the semiconductor wafer 2 used in this inspection are calculated respectively using the number of non-fatal chips and the number of fatal chips (step S47).

Display type and method of destination result for fatal/non-fatal condition in the external appearance inspection apparatus of the embodiment 5, structure and function of the analyzing apparatus 50 (external apparatus) electrically connected to the external appearance inspection apparatus and moreover effect obtained by the semiconductor device manufacturing method of the embodiment 5 are similar to that of the first embodiment and therefore the same explanation is not repeated here.

(Embodiment 6)

Figure 25:
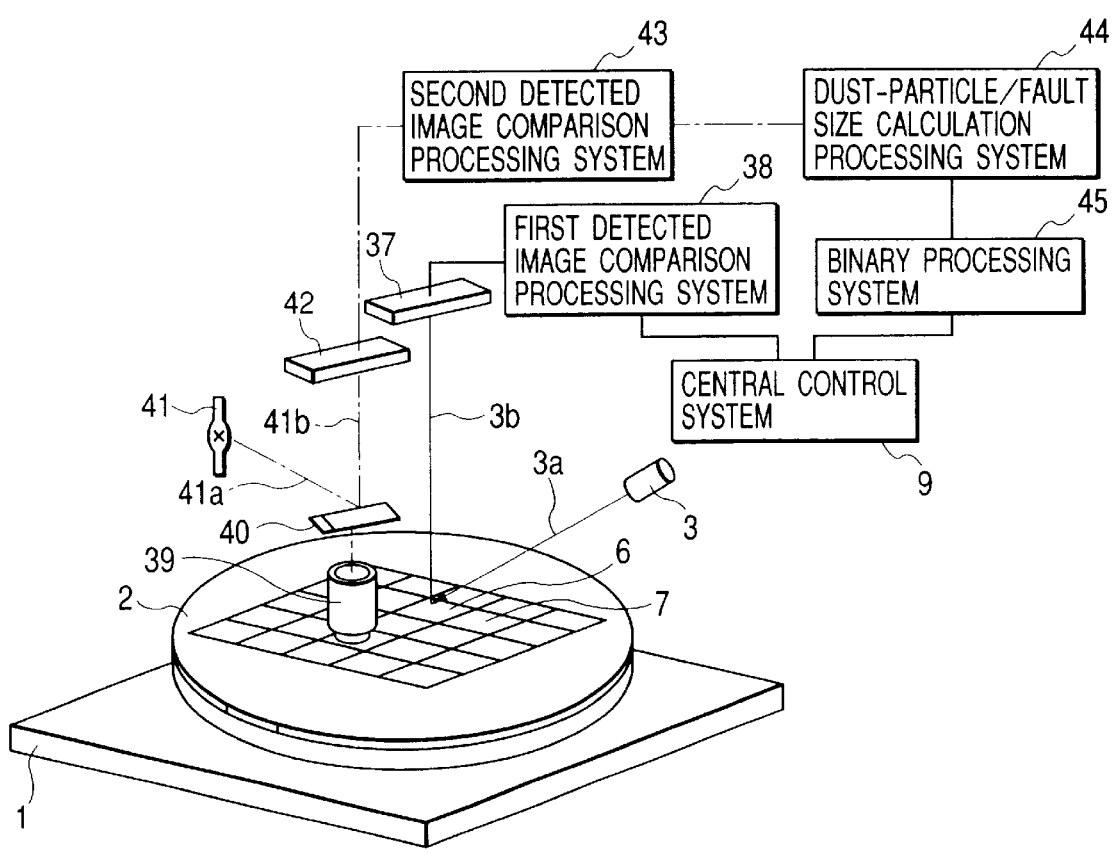
FIG. 25 is a perspective view illustrating an example of structure of the essential portion of the external appearance inspection apparatus of the embodiment 6 used in the inspection process of the semiconductor device manufacturing method of the present invention.

FIG. 25 is a perspective view illustrating an example of structure of the essential portion of the external appearance inspection apparatus of the embodiment 6 used in the inspection process of the semiconductor device manufacturing method of the present invention.

Figure 26:
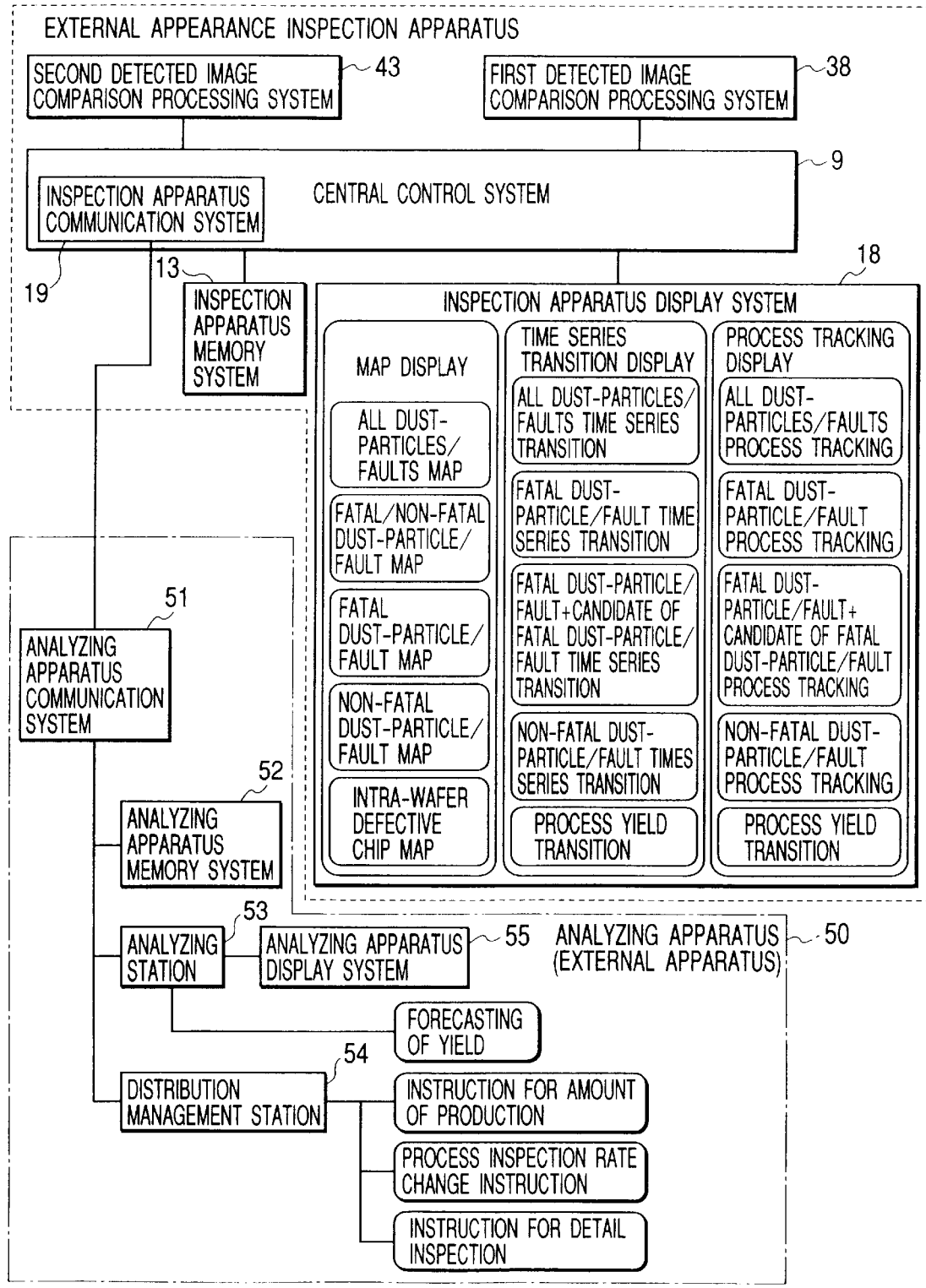
FIG. 26 is a block diagram illustrating an example of structure of the essential portion of the external appearance inspection apparatus of the embodiment 6 of FIG. 25 and the external apparatus connected thereto.

FIG. 26 is a block diagram illustrating an example of structure of the essential portion of the external appearance inspection apparatus of the embodiment 6 of FIG. 25 and the external apparatus connected thereto.

Figure 27:
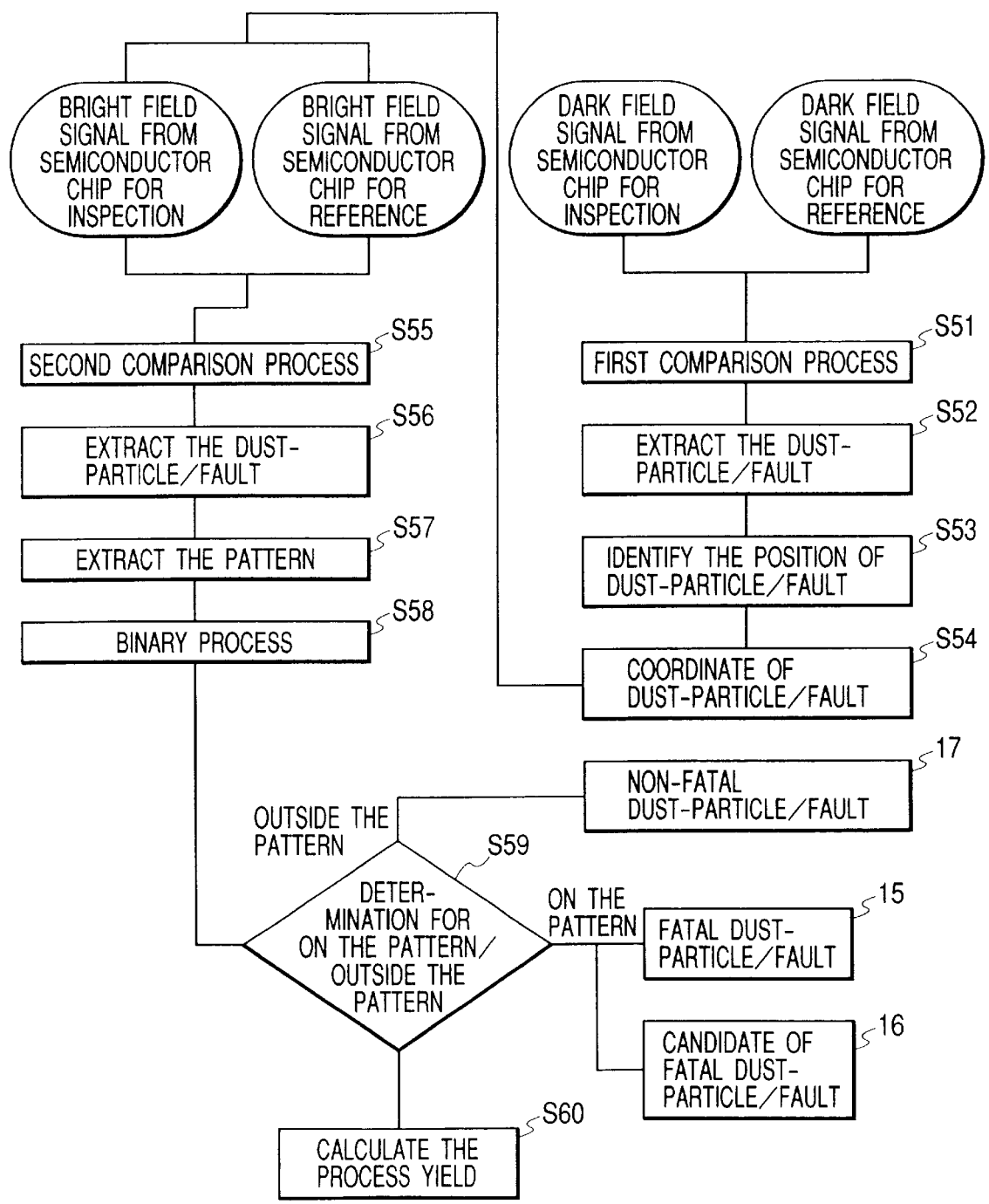
FIG. 27 is a flow diagram of inspection sequence illustrating an example of the inspection sequence executed in the inspection process of the semiconductor device manufacturing method of the embodiment 6 of the present invention.

FIG. 27 is a flow diagram of inspection sequence illustrating an example of the inspection sequence executed in the inspection process of the semiconductor device manufacturing method of the embodiment 6 of the present invention.

In the semiconductor device manufacturing method of the embodiment 6, the fatal/non-fatal condition of dust-particles/fault 8 is determined using the external appearance inspection apparatus which is almost similar to that used in the semiconductor device manufacturing process of the embodiment 1.

Here, the structure of the external appearance inspection apparatus of the embodiment 6 of FIG. 25 will be explained mainly in the difference from the external appearance inspection apparatus of FIG. 1 of the embodiment 1.

The external appearance inspection apparatus of the embodiment 6 of FIG. 25 is provided with two kinds of optical systems including the dark field system using the monochromatic light and the bright field system using visible light.

Namely, the dark field system is provided with a laser 3 for radiating the laser beam 3a of monochromatic light, a first detector 37 for detecting the scattering/diffracting beam 3b of such laser beam and a first detected image comparison processing system 38 for executing the comparison process of the dark field system, while the bright field system is provided with a lamp 41 as the light source for emitting the lamp beam 41a (visible light beam), a half-mirror 40 which reflects the lamp beam 41a and allows its reflected beam 41b to pass, a lens 39 for collecting the lamp beam 41a, a second detector 42 for detecting the reflected beam 41b from the semiconductor wafer 2 of lamp beam 41a, a second detected image comparison processing system 43 for executing the comparison process of the bright field system, a dust-particle/fault size calculating system 44 for obtaining a size of the dust-particle/fault 8 and a binary processing system 45 for executing the binary process.

Namely, the external appearance inspection apparatus of the embodiment 6 determines the fatal/non-fatal condition of dust-particle/fault 8 using the dark field system and bright field system.

The other structure of the external appearance inspection apparatus of the embodiment 6 is similar to that of the embodiment 1 and the same explanation is not repeated here.

Next, the semiconductor device manufacturing method of the embodiment 6 will then be explained.

Here, only the fatal/non-fatal condition determining method for the dust-particle/fault 8 of the embodiment 6 will be explained and since the other semiconductor manufacturing method is similar to that of the embodiment 1, the same explanation is not repeated here.

First, when the inspection chip 6 of the semiconductor wafer 2 on the stage 1 is irradiated with the monochromatic laser beam 3a (optical beam) from the laser in the dark field system, the laser beam 3a is reflected with the semiconductor wafer 2 to become the scattering/diffracting beam 3b and thereby the signal from the pattern 10 (refer to FIG. 4) and the signal from the dust-particle/fault 8 (refer to FIG. 3) are detected with the first detector 37.

Moreover, the image signal of inspection chip 6 fetched by the first detector 37 (inspection chip information) is transmitted to the first detected image comparison processing system 38.

In this first detected image comparison processing system 38, the first comparison process of the image signal from inspection chip 6 (inspection chip information) and the image signal from reference chip 7 (reference chip information) is executed (step S51 of FIG. 27). Namely, a difference between the image signal of inspection chip 6 and the previously stored image signal from reference chip adjacent to the inspection chip 6 is obtained and when this difference value is larger than the maximum value Thnmax (not illustrated) of the difference value of pattern 10, the dust-particle/fault 8 is defined as dust-particle and when such difference value is smaller than the maximum value Thnmax, the dust-particle/fault 8 is defined as the pattern 10.

Thereafter, the dust-particle/fault 8 is extracted depending on the result of determination in the first detected image comparison processing system 38 (step S52).

This first comparison process is executed for the entire part of the surface of semiconductor wafer 2 by moving the stage 1 while controlling the stage controller with the central control system 9.

As a result, position of the dust-particle/fault 8 on the semiconductor wafer 2 may be identified (step S53) and the chip matrix 11 for identifying the matrix and chip coordinate 12 in XY directions as the orthogonal coordinate from the predetermined reference origin in the chip are stored, for the position, in the inspection apparatus memory system 13 provided in the external appearance apparatus.

Thereby, the coordinate on the semiconductor wafer 2 of dust-particle/fault 8 may be obtained (step S54) and moreover a size of dust-particle/fault 8 can also be calculated using the first image comparison process.

The information about position and size of dust-particles/fault 8 is called the dust-particle/fault information.

Thereafter, inspection of the bright field system is conducted.

First, the stage 1 is moved until the visual field of lens 39 is placed in the detecting position of dust-particle/fault 8. Thereby, the lamp beam 41a is incident to the lamp 39 from the lamp 41 via the half-mirror 40. As a result, the bright field image is focused to the second detector 42 via the lens 39 and is once stored therein. Thereby, the chip information for visible beam inspection as the bright field signal from the inspection chip 6 can be obtained.

Meanwhile, the chip information for visible beam reference as the bright field image can be obtained by fetching the bright field image from the reference chip 7 to the second detector 42 with the similar method.

Thereafter, the chip information for visible beam inspection and the chip information for visible beam reference are compared in the first detected image comparison processing system 38 as the second comparison process (step S55) and thereby dust-particle/fault 8 (step S56) is extracted and moreover size of dust-particle/fault 8 and pattern 10 are extracted (step S57).

Such operation is repeated for the detected dust-particles/fault 8.

Thereafter, the central control system 9 executes the threshold value process (binary process of step S58) to the pattern information of reference chip information of visible beam and thereby determines existence of pattern 10 of the pattern information after the threshold value process for the position of dust-particle/fault 8 based on the dust-particles/fault information (step S59).

In this case, the pattern information after the threshold value process is compared with the position and size of dust-particle/fault 8. When a part of the entire part of dust-particle/fault 8 is overlapped with the pattern area (on the pattern), the dust-particle/fault 8 is defined as the fatal dust-particle/fault and it is recorded and stored in the inspection apparatus memory system 13 of FIG. 26 as the fatal dust-particle/fault 15 of FIG. 27.

Moreover, when the dust-particle/fault 8 is located at the outside of pattern (outside the pattern), this dust-particles/fault 8 is defined as the non-fatal dust-particles/fault 17 and it is then recorded and stored in the inspection apparatus memory system 13.

Moreover, when distance between dust-particle/fault 8 and pattern area is less than the predetermined value, the dust-particle/fault 8 is defined as a candidate of fatal dust-particle/fault 16 and it is then recorded and stored in the inspection apparatus memory system 13.

Thereafter, the fatal, candidate of fatal and non-fatal dust-particle/fault is recorded to the chip including the dust-particle/fault 8 determined as the fatal, candidate of fatal or non-fatal dust-particle/fault and it is then stored in the inspection apparatus memory system 13.

Moreover, the maximum yield and minimum yield of the manufacturing process of the semiconductor wafer 2 used in this inspection may be calculated respectively using the number of non-fatal chips and the number of fatal chips (step S60).

Display type and method of determination result for fatal/non-fatal dust-particle/fault in the external appearance inspection apparatus of the embodiment 6 and structure and function of the analyzing apparatus 50 (external apparatus) electrically connected to the external appearance inspection apparatus are similar to that of the embodiment 1 and the same explanation is not repeated here.

In the embodiment 6, after the pattern information of dust-particle/fault 8 is obtained from the image of dark field system, the pattern information of dust-particle/fault 8 is obtained from the image of the bright field system and fatal/non-fatal dust-particle/fault is determined using the image of bright field system.

Accordingly, resolution of image to be fetched can be improved using the image of bright field system and as a result, accuracy for determination of dust-particle/fault can be enhanced.

Since the other effect obtained by the semiconductor device manufacturing method of the embodiment is similar to that of the embodiment 1, the same explanation is not repeated here.

(Embodiment 7)

Figure 28:
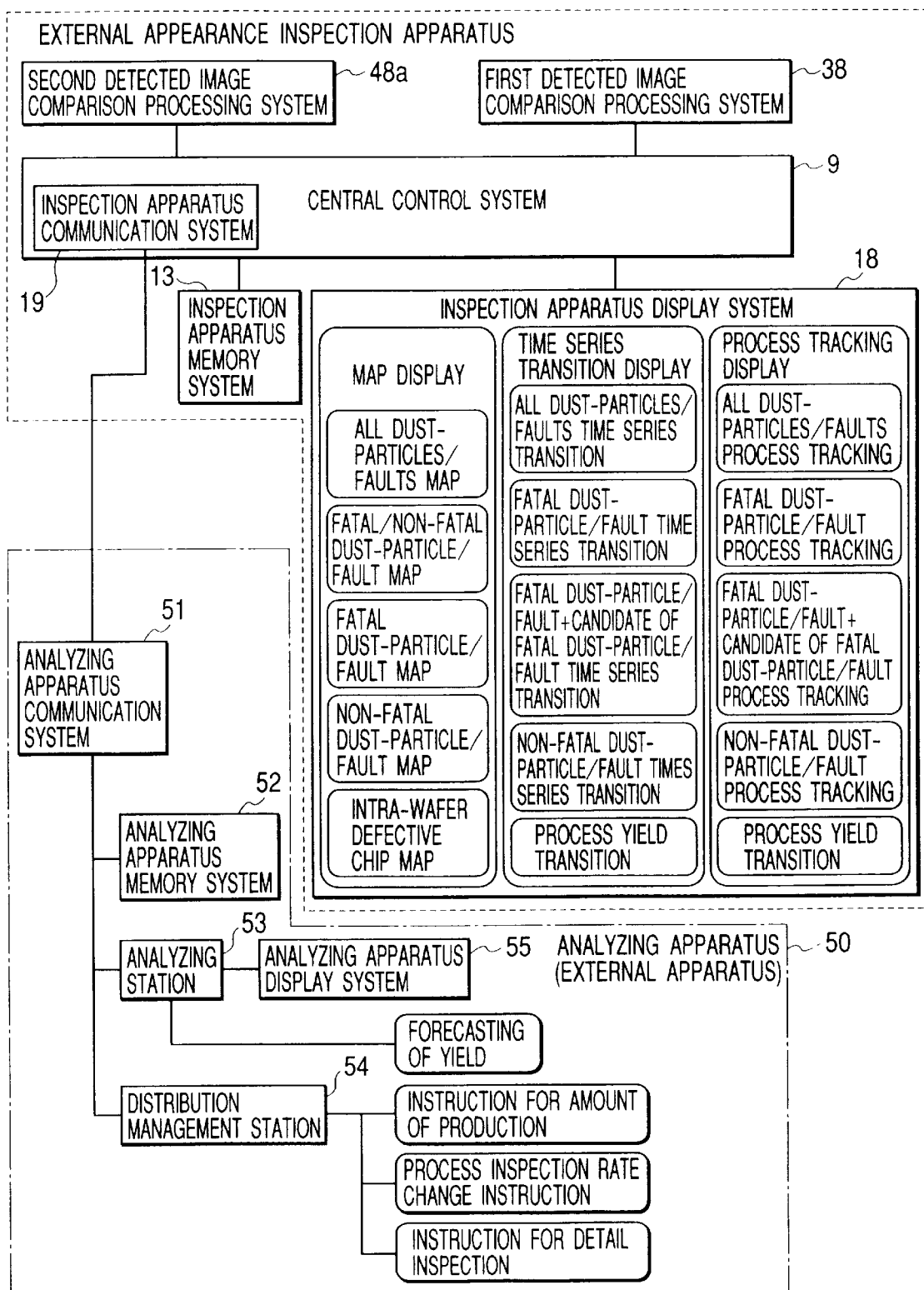
FIG. 28 is a block diagram illustrating an example of structure of the essential portion of the external appearance inspection apparatus of the embodiment 7 and the external apparatus connected thereto used in the inspection process of the semiconductor device manufacturing method of the present invention.

FIG. 28 is a block diagram illustrating an example of structure of the essential portion of the external appearance inspection apparatus of the embodiment 7 and the external apparatus connected thereto used in the inspection process of the semiconductor device manufacturing method of the present invention.

Figure 29:
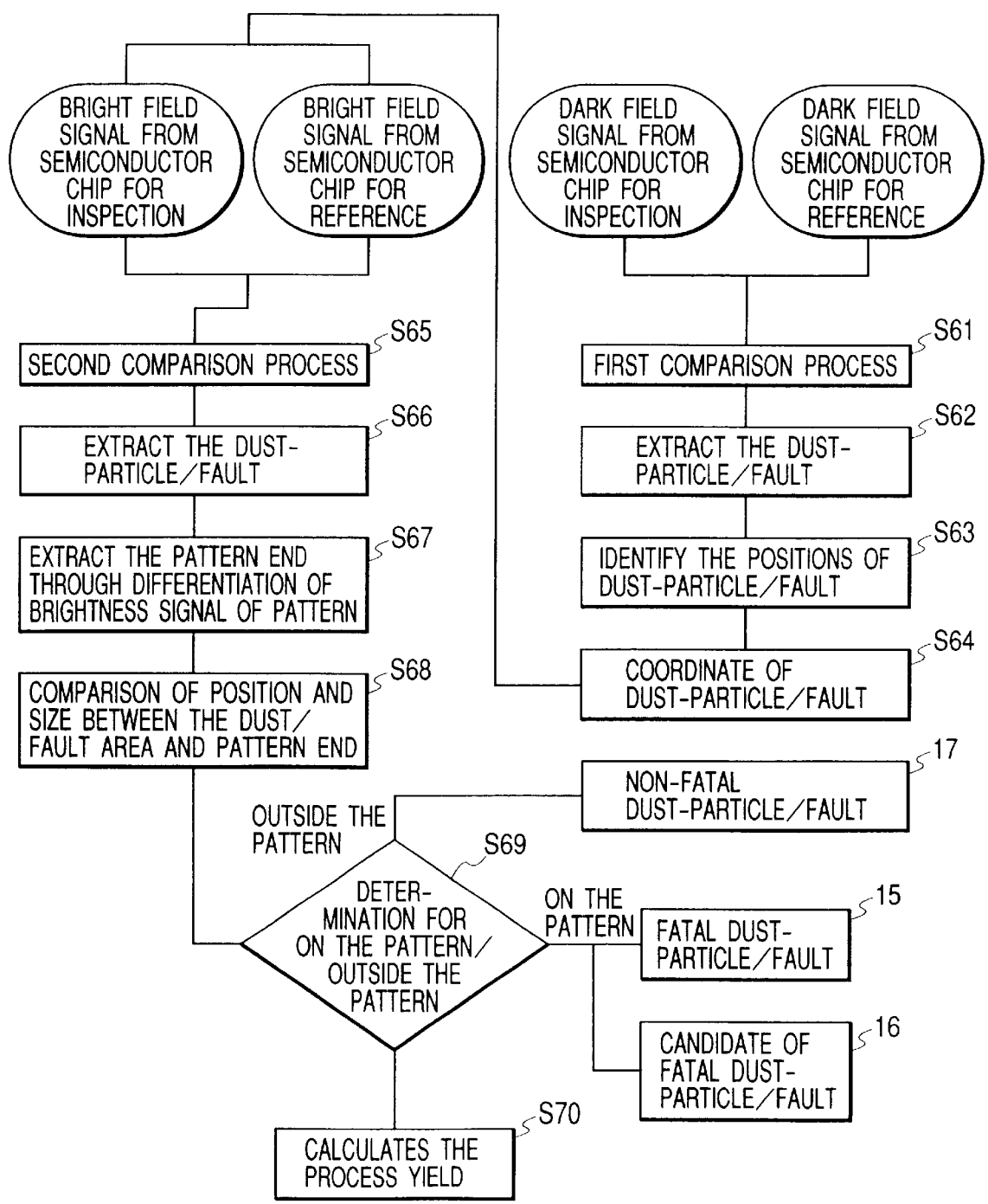
FIG. 29 is a flow diagram of inspection sequence illustrating an example of the inspection sequence executed in the inspection process of the semiconductor device manufacturing method of the embodiment 7 of the present invention.

FIG. 29 is a flow diagram of inspection sequence illustrating an example of the inspection sequence executed in the inspection process of the semiconductor device manufacturing method of the embodiment 7 of the present invention.

In the semiconductor device manufacturing method of the embodiment 7, the fatal/non-fatal condition of the dust-particles/fault 8 is determined using the external appearance inspection apparatus which is almost similar to that used in the semiconductor device manufacturing process of the embodiment 6.

The external appearance inspection apparatus of the embodiment 7 of FIG. 28 comprises the dark field system (first detected image comparison processing system 38) and the bright field system (second detected image comparison processing system 48a) as in the case of the external appearance inspection apparatus of the embodiment 6 and the structure thereof is also similar to that of the embodiment 6. Only difference is that the pattern information is obtained with the differentiation on the occasion of determination for fatal/non-fatal dust-particles/fault after the second comparison process conducted in the second detected image comparison processing system 48a.

Since the other structure of the external appearance inspection apparatus of the embodiment 7 is similar to that of the external appearance inspection apparatus of the embodiment 6, the same explanation is not repeated here.

Next, the semiconductor device manufacturing method of the embodiment 7 will be explained.

Only the method of determining the fatal/non-fatal condition of the dust-particle/fault 8 of the embodiment 7 will be explained and since the other semiconductor device manufacturing method is similar to that of the embodiment 1, the same explanation is not repeated here.

First, when the inspection chip 6 of the semiconductor wafer 2 on the stage 1 is irradiated with the monochromatic laser beam 3a (optical beam) from the laser 3, the laser beam 3a is reflected with the semiconductor wafer 2 to become the scattering/diffracting beam 3b. Thereby, the signal from pattern 10 (refer to FIG. 4) and the signal from dust-particles/fault 8 (refer to FIG. 3) are detected with the first detector 37.

Moreover, the image signal of inspection chip 6 fetched by the first detector 37 (inspection chip information) is transmitted to the first detected image comparison processing system 38.

In the first detected image comparison processing system 38, the image signal from inspection chip 6 (inspection chip information) is compared with the image signal from reference chip 7 (reference chip information) as the first comparison process (step S61 of FIG. 29). Namely, a difference between the image signal of inspection chip 6 and the previously stored image signal of reference chip 7 adjacent to the inspection chip 6 is obtained and when this difference value is larger than the maximum value Thnmax (not illustrated) of the difference value of the pattern 10, the dust-particle/fault 8 is defined as dust-particle and when such difference value is smaller than such maximum value, the dust-particle/fault 8 is defined as the pattern 10.

Thereafter, the dust-particle/fault 8 is extracted depending on the determination result of the first detected image comparison processing system 38 (step S62).

This first comparison process is executed for the entire part of the surface of semiconductor wafer 2 by moving the stage 1 while controlling the stage controller with the central control system 9.

As a result, position of dust-particle/fault 8 on the semiconductor wafer 2 may be identified (step S63) and the chip matrix 11 for identifying the chip and the chip coordinate 12 in the XY directions as the orthogonal coordinate from the predetermined reference origin in the chip for the above position are stored, as illustrated in FIG. 3, in the inspection apparatus memory system 13 provided in the external appearance inspection apparatus.

Thereby, the coordinate on the semiconductor wafer 2 of the dust-particle/fault 8 may be obtained (step S64) and moreover the size of dust-particle/fault 8 can also be calculated using the first image comparison process.

The information about position and size of dust-particles/fault 8 is called the dust-particle/fault information.

Thereafter, the inspection is conducted for the bright field system.

First, the stage 1 is moved until the visual field of the lens 39 is set to the detecting position of the dust-particles/fault 8. Thereby, the lamp beam 41a from the lamp 41 is incident to the lens 39 via the half-mirror 40. As a result, the bright field image is focused to the second detector 42 via the lens 39 and is temporarily stored there. Accordingly, the chip information for visible beam inspection as the bright field signal from the inspection chip 6 can be obtained.

Meanwhile, the chip information for visible beam reference as the bright field signal is obtained by fetching the bright field image from the reference chip 7 with the second detector 42 is also obtained by the similar method.

Thereafter, the chip information for visible beam inspection is compared with the chip information for visible beam reference in the first detected image comparison processing system 38 as the second comparison process (step S65) and thereby the dust-particle/fault 8 may be extracted (step S66).

These operations are repeated for the detected dust-particles/fault 8.

Thereafter, the central control system 9 differentiates in the X and Y directions the pattern information of reference chip information of the visible beam, namely the brightness signal of the pattern area extracted with the bright field image and thereby the end part of pattern 10 can be extracted (step S67).

As a result, density of pattern 10 can be detected.

Subsequently, this result is compared with the position and size of extracted dust-particle/fault 8 (step S68) and thereby existence of pattern 10 based on the pattern information after such comparison process for the position of dust-particles/fault 8 based on the dust-particle/fault information is determined (step S69).

Here, when a part or entire part of the dust-particle/fault 8 overlaps with the pattern area (one the pattern), such dust-particle/fault 8 is defined as the fatal dust-particles/fault and it is then recorded and stored in the inspection apparatus memory system 13 of FIG. 28 as the fatal dust-particle/fault 15 of FIG. 29.

Moreover, when the dust-particle/fault 8 is located at the outside of pattern area (outside the pattern), this dust-particles/fault is determined as the non-fatal dust-particle/fault 17 and it is then recorded and stored in the inspection apparatus memory system 13.

Moreover, when the distance between dust-particle/fault 8 and pattern area is less than the predetermined value, such dust-particle/fault is determined as the candidate of fatal dust-particle/fault 16 and it is then recorded and stored in the inspection apparatus memory system 13.

Thereafter, the fatal, candidate of fatal or non-fatal condition is recorded to the chip including the dust-particles/fault 8 which is determined as the fatal, candidate of fatal or non-fatal dust-particle/fault and it is then stored in the inspection apparatus memory system 13.

In addition, the estimated maximum yield and estimated minimum yield of the manufacturing process of semiconductor wafer 2 used in this inspection are calculated respectively using the number of non-fatal chips and the number of fatal chips (step S70).

Display type and method of the determination result for fatal/non-fatal dust-particle/fault in the external appearance inspection apparatus of the embodiment 7, structure and function of the analyzing apparatus 50 (external apparatus) electrically connected to the external appearance inspection apparatus and moreover the effect of the semiconductor device manufacturing method of the embodiment 7 are similar to that of the embodiment 6 and therefore the same explanation is not repeated here.

(Embodiment 8)

Figure 30:
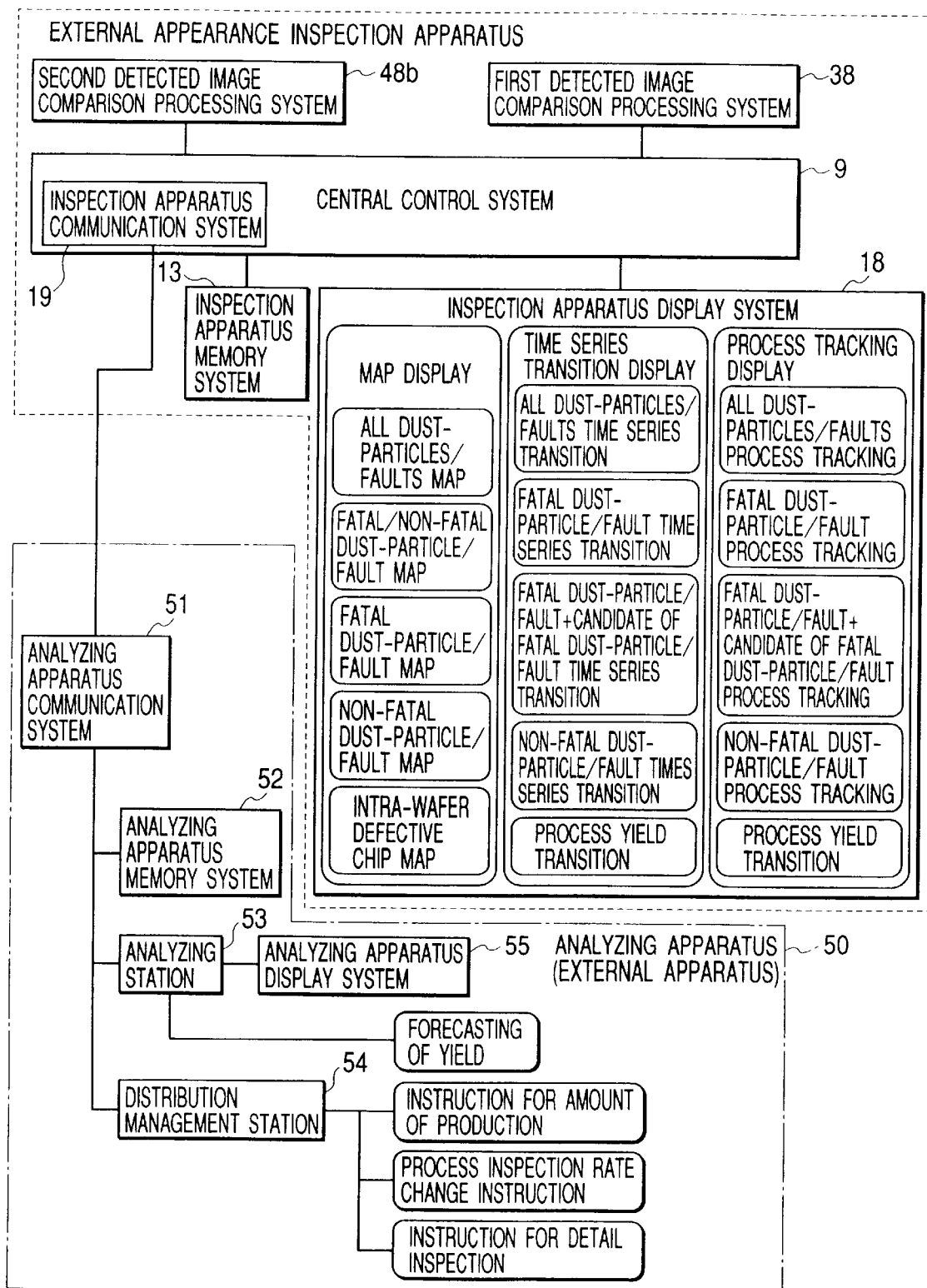
FIG. 30 is a block diagram illustrating an example of structure of the essential portion of the external appearance inspection apparatus of the embodiment 8 and the external apparatus connected thereto used in the inspection process of the semiconductor device manufacturing method of the present invention.

FIG. 30 is a block diagram illustrating an example of structure of the essential portion of the external appearance inspection apparatus of the embodiment 8 and the external apparatus connected thereto used in the inspection process of the semiconductor device manufacturing method of the present invention.

Figure 31:
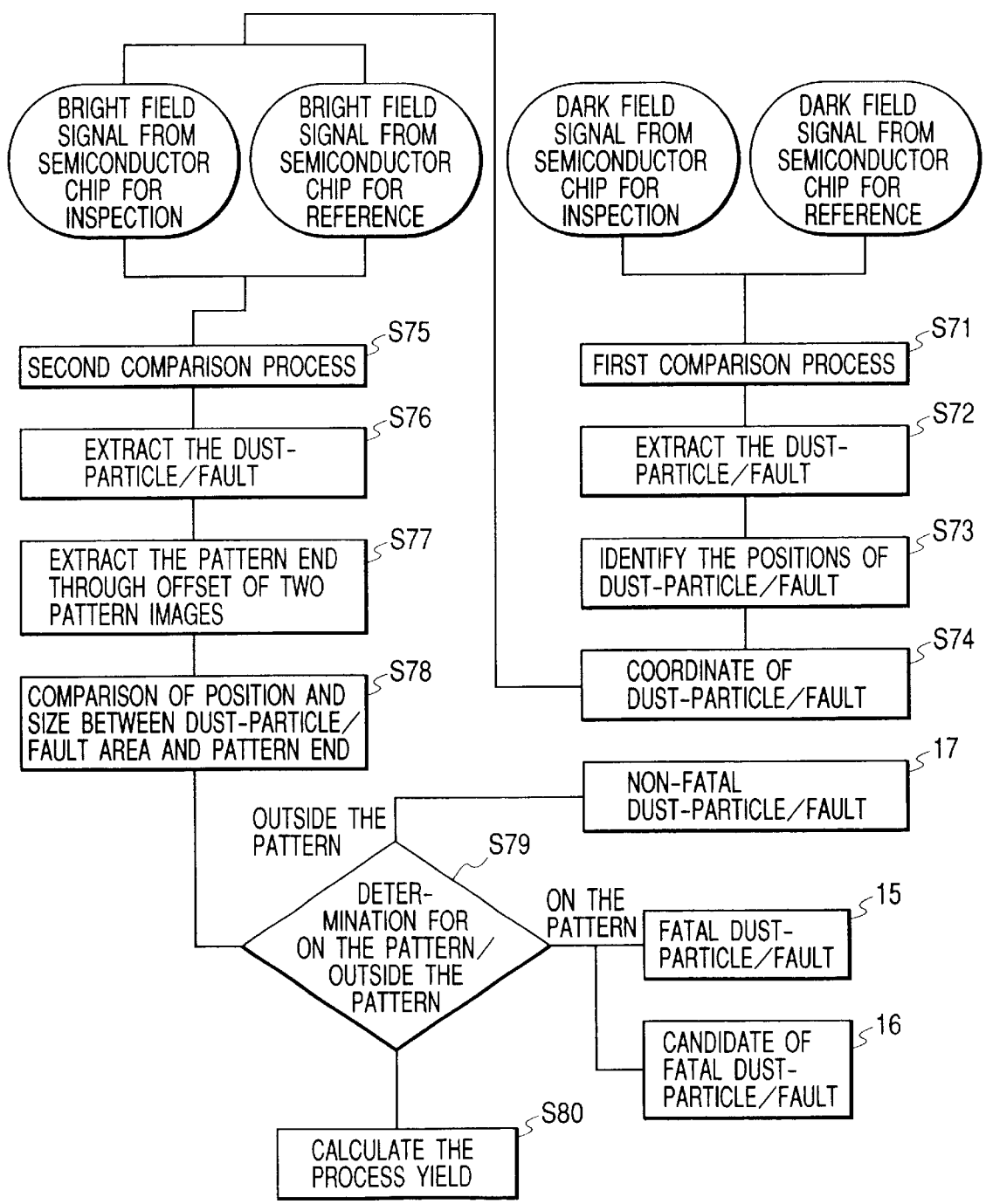
FIG. 31 is a flow diagram of the inspection sequence illustrating an example of the inspection sequence executed in the inspection process of the semiconductor device manufacturing method of the embodiment 8 of the present invention.

FIG. 31 is a flow diagram of the inspection sequence illustrating an example of the inspection sequence executed in the inspection process of the semiconductor device manufacturing method of the embodiment 8 of the present invention.

In the semiconductor device manufacturing method of the embodiment 8, the fatal/non-fatal condition of the dust-particles/fault 8 is determined using the external appearance inspection apparatus which is almost similar to that used in the semiconductor device manufacturing process of the embodiment 6.

The external appearance inspection apparatus of the embodiment 8 of FIG. 30 comprises, like the external appearance inspection apparatus of the embodiment 6, the dark field system (first detected image comparison processing system 38) and bright field system (second detected image comparison processing system 48b) and the structure thereof is also similar to that of the embodiment 6. Only difference is that the pattern information is obtained with an image offset at the time of determining the fatal/non-fatal dust-particle/fault after the second comparison process executed in the second detected image comparison processing system 48b.

The other structure of the external appearance inspection apparatus of the embodiment 8 is similar to that of the embodiment 6 and therefore the same explanation is not repeated here.

Next, the semiconductor device manufacturing method of the embodiment 8 will be explained.

Only the method of determining fatal/non-fatal condition of the dust-particle/fault 8 of the embodiment 8 is explained here and the other semiconductor device manufacturing method is similar to that of the embodiment 1 and therefore the same explanation is not repeated here.

First, when the inspection ship 6 of semiconductor wafer 2 on the stage 1 is irradiated with the monochromatic laser beam 3a (optical beam) from the laser 3, the laser beam 3a is reflected with the semiconductor wafer 2 to become the scattering/diffracting beam 3b. Thereby, the signal from pattern 10 (refer to FIG. 4) and the signal from dust-particle/fault 8 (refer to FIG. 3) are detected with the first detector 37.

Moreover, the image signal of inspection chip 6 fetched to the first detector 37 (inspection chip information) is transmitted to the first detected image comparison processing system 38.

In the first detected image comparison processing system 38, the image signal from inspection chip 6 (inspection chip information) is compared with the image signal from reference chip 7 (reference chip information) as the first comparison process (step S71 of FIG. 31). That is, a difference value between the inspection chip 6 and the previously stored image signal of reference chip 7 adjacent to the inspection chip 6 is obtained and when this difference value is larger than the maximum value Thnmax (not illustrated) of the difference value of pattern 10, the dust-particle/fault 8 is determined as the dust-particle and when such different value is smaller than the maximum value, the dust-particle/fault 8 is determined as the pattern 10.

Thereafter, the dust-particle/fault 8 is extracted depending on the determination result of the first detected image comparison processing system 38 (step S72).

This first comparison process is executed for the entire part of the semiconductor wafer 2 by moving the stage 1 while controlling the stage controller with the central control system 9.

As a result, position of the dust-particle/fault 8 on the semiconductor wafer 2 may be identified (step S73) and the chip matrix 11 for identifying the chip and the chip coordinate 12 in the XY directions as the orthogonal coordinate from the predetermined reference origin in the chip for such position are stored, as illustrated in FIG. 3, in the inspection apparatus memory system 13 provided in the external appearance inspection apparatus.

Thereby, the coordinate on the semiconductor wafer 2 of dust-particle/fault 8 can be obtained (step S74) and a size of dust-particle/fault 8 can also be calculated using the first image comparison process.

The information about position and size of dust-particle/fault 8 is called the dust-particle/fault information.

Thereafter, the inspection is conducted for the bright field system.

First, the stage 1 is moved until the visual field of the lens 39 is set to the detecting position of the dust-particles/fault 8. Thereby, the lamp beam 41a from the lamp 41 is incident to the lens 39 via the half-mirror 40. As a result, the bright field image is focused to the second detector 42 via the lens 39 and it is then temporarily stored therein. Thereby, the chip information for visible beam inspection as the bright field signal from the inspection chip 6 can be obtained.

Meanwhile, the bright field image from the reference chip 7 is also fetched to the second detector 42 with the similar method and thereby the chip information for visible beam reference as the bright field signal can also be obtained.

Thereafter, the chip information for visible beam inspection is compared with the chip information for visible beam reference in the first detected image comparison processing system 38 as the second comparison process (step S75) and thereby the dust-particle/fault 8 can be extracted (step S76).

Thereafter, the central control system 9 shifts (offset) the pattern information of reference chip information of visible light, namely the brightness signal of the pattern area extracted with the bright field image and thereby the end part of the pattern 10 is extracted from the difference signal (step S77).

This operation is repeated for the detected dust-particles/fault 8.

As a result, density of pattern 10 can be detected.

Subsequently, this result is compared with position and size of the extracted dust-particle/fault 8 (step S78) and thereby existence of the pattern based on the pattern information after the comparison process for the position of dust-particle/fault 8 based on the dust-particle/fault information can be determined (step S79).

Here, when a part or the entire part of the dust-particles/fault 8 is overlapped with the pattern area (on the pattern), the dust-particle/fault 8 is determined as the fatal dust-particle/fault and it is recorded and stored in the inspection apparatus memory system 13 of FIG. 30 as the fatal dust-particle/fault 15 as illustrated in FIG. 31.

Moreover, when the dust-particle/fault is located at the outside of the pattern area (outside the pattern), the dust-particle/fault 8 is determined as the non-fatal dust-particles/fault 17 and it is then recorded and stored in the inspection apparatus memory system 13.

Moreover, distance between the dust-particle/fault 8 and pattern area is less than the predetermined value, the dust-particle/fault 8 is determined as the candidate of fatal dust-particle/fault 16 and it is then recorded and stored in the inspection apparatus memory system 13.

Thereafter, the fatal, candidate of fatal or non-fatal condition is recorded to the chip including the dust-particles/fault 8 determined as the fatal, candidate of fatal and non-fatal dust-particle/fault and it is then stored in the inspection apparatus memory system 13.

Moreover, the estimated maximum yield and estimated minimum yield of the manufacturing process of semiconductor wafer 2 used in this inspection are calculated respectively using the number of non-fatal chips and the number of fatal chips (step S80).

Display type and method of determination result for fatal/non-fatal dust-particle/fault in the external appearance inspection apparatus of the embodiment 8, structure and function of the analyzing apparatus 50 (external apparatus) electrically connected to the external appearance inspection apparatus and the effect of the semiconductor device manufacturing method of the embodiment 8 are similar to that of the embodiment 6 and therefore the same explanation is not repeated here.

(Embodiment 9)

Figure 32:
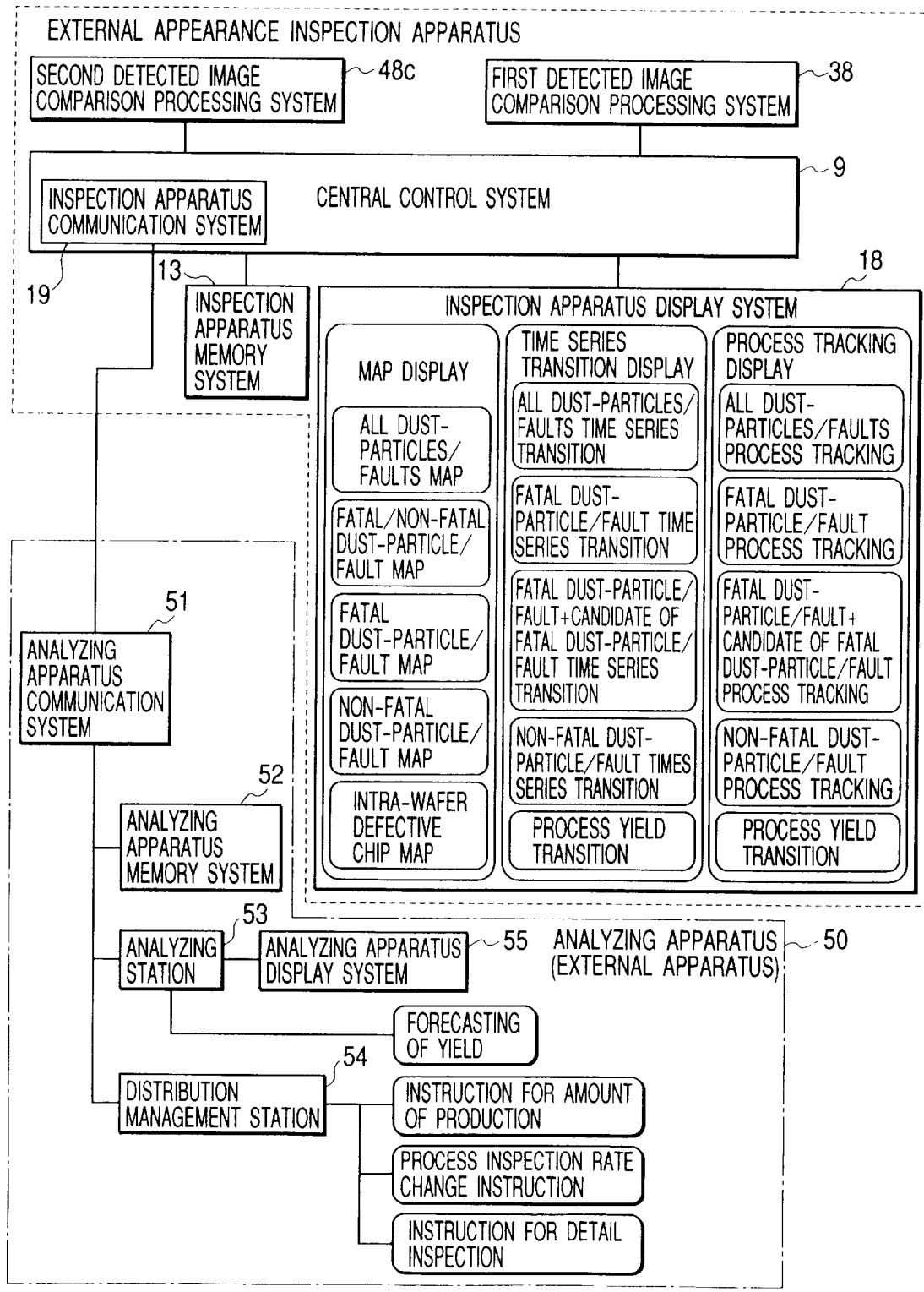
FIG. 32 is a block diagram illustrating an example of structure of the essential portion of the external appearance inspection apparatus of the embodiment 9 and the external apparatus connected thereto used in the inspection process of the semiconductor device manufacturing method of the present invention.

FIG. 32 is a block diagram illustrating an example of structure of the essential portion of the external appearance inspection apparatus of the embodiment 9 and the external apparatus connected thereto used in the inspection process of the semiconductor device manufacturing method of the present invention.

Figure 33:
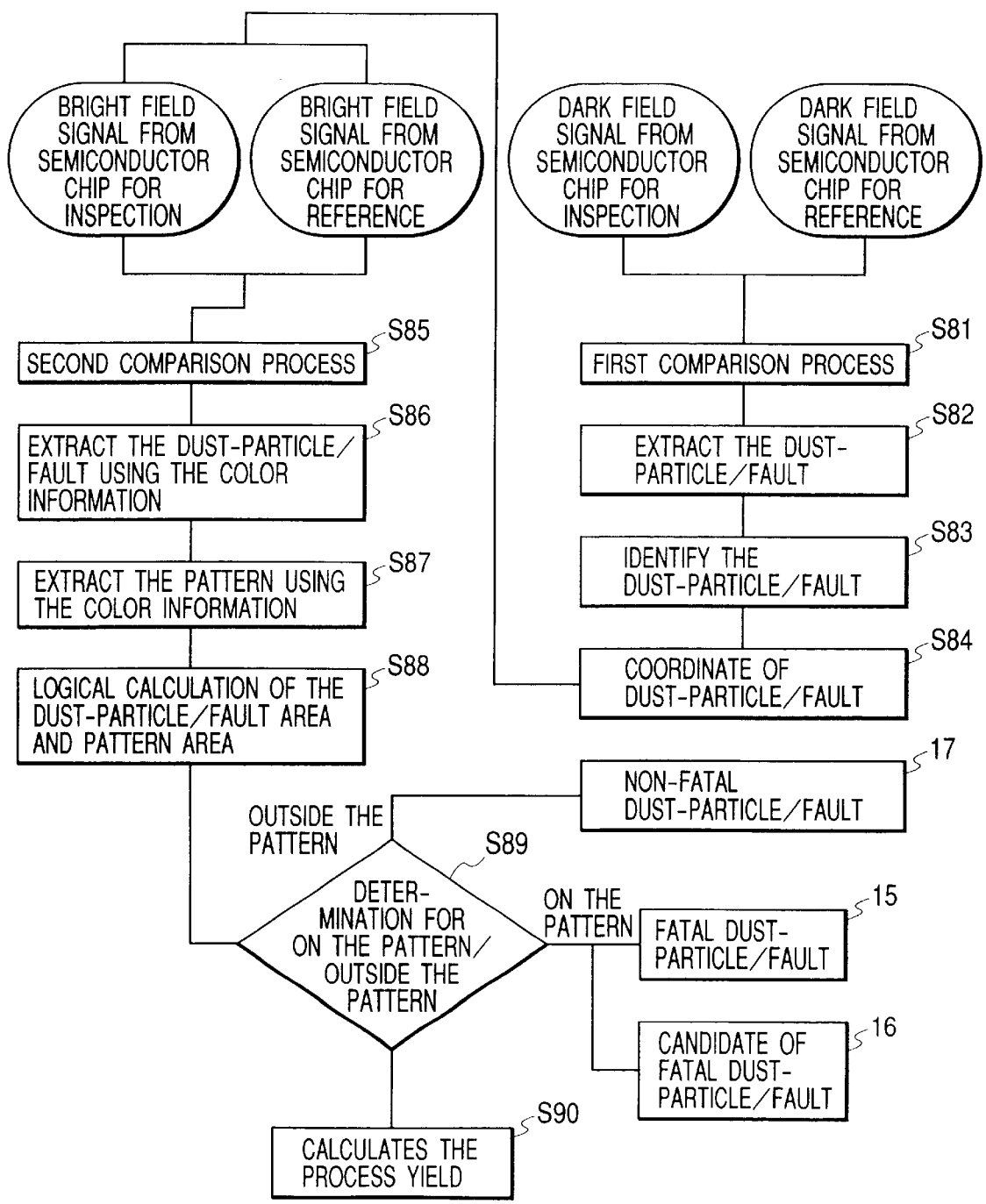
FIG. 33 is a flow diagram of inspection sequence illustrating the inspection sequence executed in the inspection process of the semiconductor device manufacturing method of the embodiment 9 of the present invention.

FIG. 33 is a flow diagram of inspection sequence illustrating the inspection sequence executed in the inspection process of the semiconductor device manufacturing method of the embodiment 9 of the present invention.

In the semiconductor device manufacturing method of the embodiment 9, the fatal/non-fatal condition of the dust-particles/fault 8 is determined using the external appearance inspection apparatus which is almost similar to that used in the semiconductor device manufacturing process of the embodiment 6.

The external appearance inspection apparatus of the embodiment 9 illustrated in FIG. 32 comprises, like the external appearance inspection apparatus of the embodiment 6, the dark field system (first detected image comparison processing system 38) and the bright field system (second detected image comparison processing system 48c) and the structure thereof is also similar to that of the embodiment 6. Only difference is that the pattern information is obtained using the color information at the time of determining the fatal/non-fatal condition after the second comparison process conducted in the second detected image comparison processing system 48c.

Namely, the second detected image comparison processing system 48c in the external appearance inspection apparatus of the embodiment 9 is the color information inspection system for inspecting color information fetched with the bright field optical system.

Since the other structure of the external appearance inspection apparatus of the embodiment 9 is similar to that of the embodiment 6, the same explanation is not repeated here.

Next, the semiconductor device manufacturing method of the embodiment 9 will be explained.

Here, only the method for determining the fatal/non-fatal condition of the dust-particle/fault 8 of the embodiment 9 is explained and since the other semiconductor device manufacturing method is also similar to that of the embodiment 1, the same explanation is not repeated here.

First, in the dark field system, when the inspection chi 6 of semiconductor wafer 2 on the stage 1 is irradiated with the monochromatic laser beam 3a (optical beam) from the laser 3, the laser beam 3a is reflected from the semiconductor wafer 2 to become the scattering/diffracting beam 3b. Thereby, the signal from pattern 10 (refer to FIG. 4) and signal from dust-particle/fault 8 (refer to FIG. 3) are detected with the first detector 37.

Moreover, the image signal of inspection chip 6 fetched to the first detector 37 (inspection chip information) is transmitted to the first detected image comparison processing system 38.

In this first detected image comparison processing system 38, the image signal from inspection chip 6 (inspection chip information) is compared with the image signal from reference chip 7 (reference chip information) as the first comparison process (step S81 of FIG. 33). Namely, a difference value between the image signal of inspection chip 6 and the previously stored image signal of reference chip 7 neighboring the inspection chip 6 and when this difference value is larger than the maximum value Thnmax (not illustrated) of the difference value of pattern 10, the dust-particle/fault 8 is determined as dust-particle and when such difference value is smaller than such maximum value, the dust-particle/fault 8 is determined as pattern 10.

Thereafter, the dust-particle/fault 8 is extracted depending on the determination result of the first detected image comparison processing system 38 (step S82).

This first comparison process is executed for the entire part of the semiconductor wafer 2 by moving the stage 1 while controlling the stage controller with the central control system 9.

As a result, the dust-particle/fault 8 on the semiconductor wafer 2 is identified (step S83) and the chip matrix 11 for identifying the chip and the chip coordinate 12 in the XY directions as the orthogonal coordinate from the predetermined reference origin in the chip for such position are stored, as illustrated in FIG. 3, in the inspection apparatus memory system 13 provided in the external appearance inspection apparatus.

Thereby, the coordinate on the semiconductor wafer 2 of dust-particle/fault 8 can be obtained (step S84) and a size of dust-particle/fault 8 can also be calculated using the first image comparison process.

The information about position and size of dust-particles/fault 8 is called the dust-particle/fault information.

Thereafter, the inspection is conducted for the bright field system.

First, the stage 1 is moved until the visual field of the lens 39 is set to the detecting position of the dust-particles/fault 8. Thereby, the lamp beam 41a from the lamp is incident to the lens 39 via the half-mirror 40. As a result, the bright field image is focused to the second detector 42 via the lens 39 and it is then temporarily stored therein. Thereby, the chip information for visible beam inspection as the bright field signal from the inspection chip 6 can be obtained.

Meanwhile, the bright field image from the reference chip 7 is also fetched to the second detector 42 with the similar method and thereby the chip information for visible beam reference as the bright field signal can also be obtained.

Thereafter, the chip information for visible beam inspection is compared with the chip information for visible beam reference in the second detected image comparison processing system 48c, namely in the color information inspection system as the second comparison process (step S85)

In this case, the central control system 9 extracts the dust-particle/fault 8 using the color information in the dark field system of the inspection chip 6 of visible beam (step S86)

Moreover, the pattern information based on the reference chip information is obtained using the color information. Namely, the pattern 10 using color information is extracted (step S87).

This operation is repeated for the detected dust-particles/fault 8.

Thereafter, density of pattern 10 can be detected using the color information of the pattern area extracted with the bright field image.

When a plurality of dust-particles/faults 8 exist in one visual field, these are considered as the single dust-particles/fault by inclusion of the dust-particles/faults 8 which can be seen as the dust-particles/faults of the same color.

This result is compared with position and size of the extracted dust-particle/fault 8 (step S88) and thereby existence of the pattern based on the pattern information after the comparison process for the position of dust-particle/fault 8 based on the dust-particle/fault information can be determined (step S89).

Here, when a part or the entire part of the dust-particles/fault 8 is overlapped with the pattern area (on the pattern), the dust-particle/fault 8 is determined as the fatal dust-particle/fault and it is recorded and stored in the inspection apparatus memory system 13 of FIG. 32 as the fatal dust-particle/fault 15 as illustrated in FIG. 33.

Moreover, when the dust-particle/fault is located at the outside of the pattern area (outside the pattern), the dust-particle/fault 8 is determined as the non-fatal dust-particles/fault 17 and it is then recorded and stored in the inspection apparatus memory system 13.

Moreover, distance between the dust-particle/fault 8 and pattern area is less than the predetermined value, the dust-particle/fault 8 is determined as the candidate of fatal dust-particle/fault 16 and it is then recorded and stored in the inspection apparatus memory system 13.

Thereafter, the fatal, candidate of fatal or non-fatal condition is recorded to the chip including the dust-particles/fault 8 determined as the fatal, candidate of fatal and non-fatal dust-particle/fault and it is then stored in the inspection apparatus memory system 13.

Moreover, the estimated maximum yield and estimated minimum yield of the manufacturing process of semiconductor wafer 2 used in this inspection are calculated respectively using the number of non-fatal chips and the number of fatal chips (step S90).

Display type and method of determination result for fatal/non-fatal dust-particle/fault in the external appearance inspection apparatus of the embodiment 9, structure and function of the analyzing apparatus 50 (external apparatus) electrically connected to the external appearance inspection apparatus and the effect of the semiconductor device manufacturing method of the embodiment 9 are similar to that of the embodiment 6 and therefore the same explanation is not repeated here.

(Embodiment 10)

Figure 34:
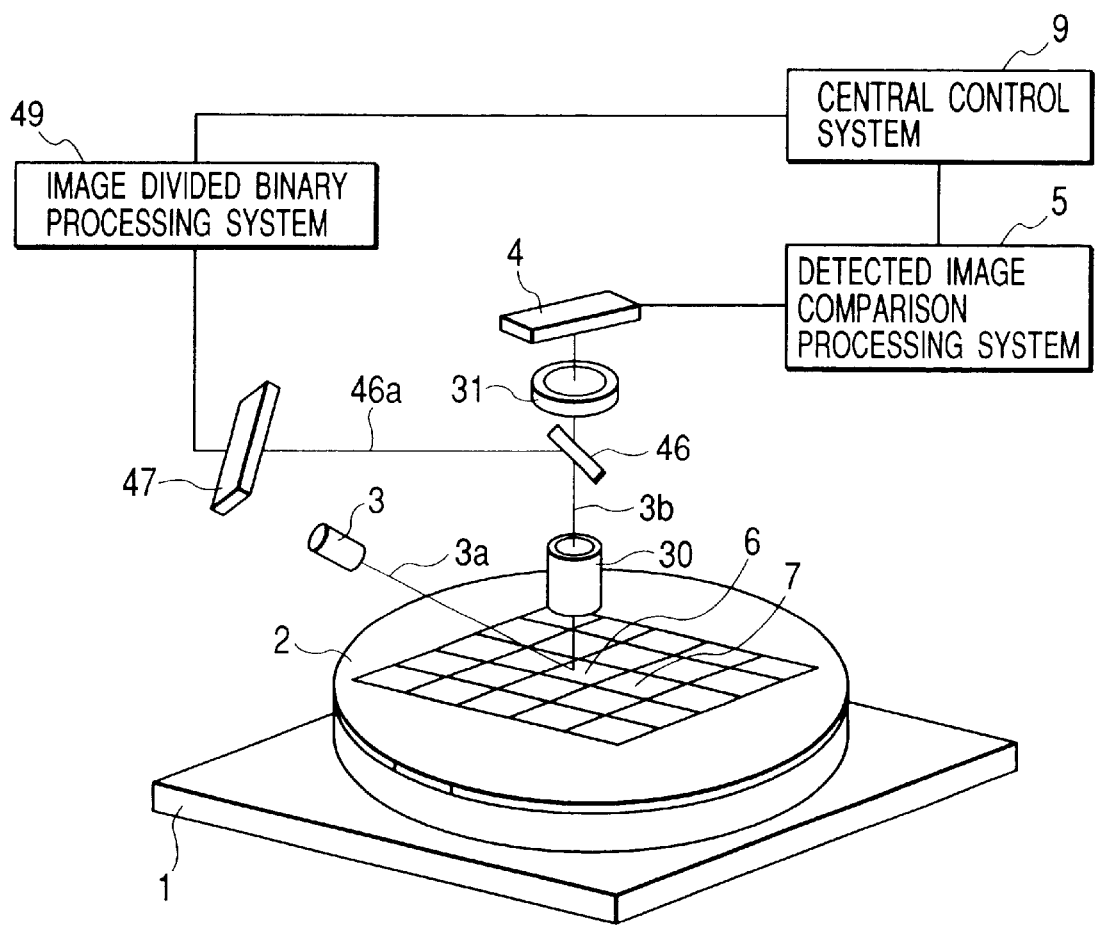
FIG. 34 is a perspective view illustrating an example of structure of the essential portion of the external appearance inspection apparatus of the embodiment 10 used in the inspection process of the semiconductor device manufacturing method of the present invention.

FIG. 34 is a perspective view illustrating an example of structure of the essential portion of the external appearance inspection apparatus of the embodiment 10 used in the inspection process of the semiconductor device manufacturing method of the present invention.

Figure 35:
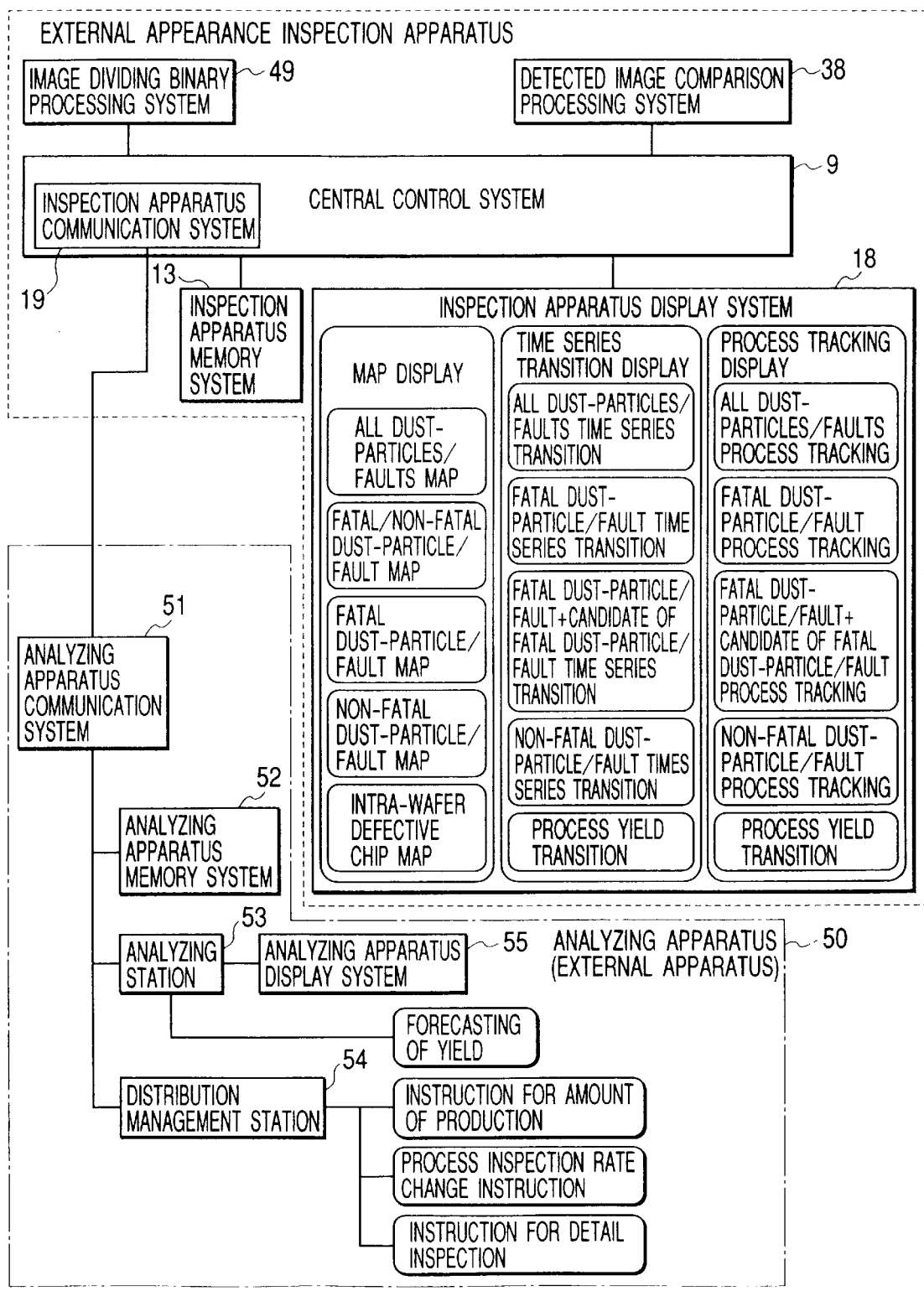
FIG. 35 is a block diagram illustrating an example of the essential portion of the external appearance inspection apparatus of the embodiment 10 of FIG. 34 and the external apparatus connected thereto.

FIG. 35 is a block diagram illustrating an example of the essential portion of the external appearance inspection apparatus of the embodiment 10 of FIG. 34 and the external apparatus connected thereto.

Figures 36A, 36B:
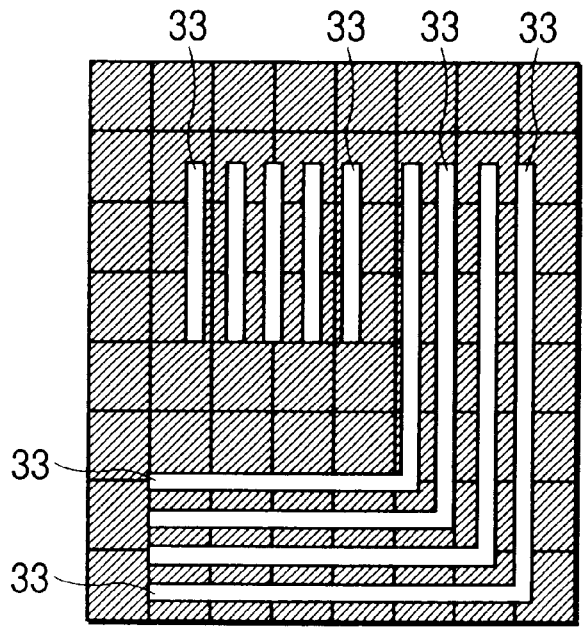
FIGS. 36(a), 36(b) are diagrams illustrating examples of the fatal/non-fatal condition determination method used in the inspection process of the semiconductor device manufacturing method of the embodiment 10 of the present invention, including the dark field image diagram of pattern of the reference chip (a) and the 8×8 divided diagram divided through the binary process of (a) (b).

FIGS. 36(a), 36(b) are diagrams illustrating examples of the fatal/non-fatal condition determination method used in the inspection process of the semiconductor device manufacturing method of the embodiment 10 of the present invention, including the dark field image diagram of pattern of the reference chip (a) and the 8×8 divided diagram divided through the binary process of (a) (b).

Figure 37:
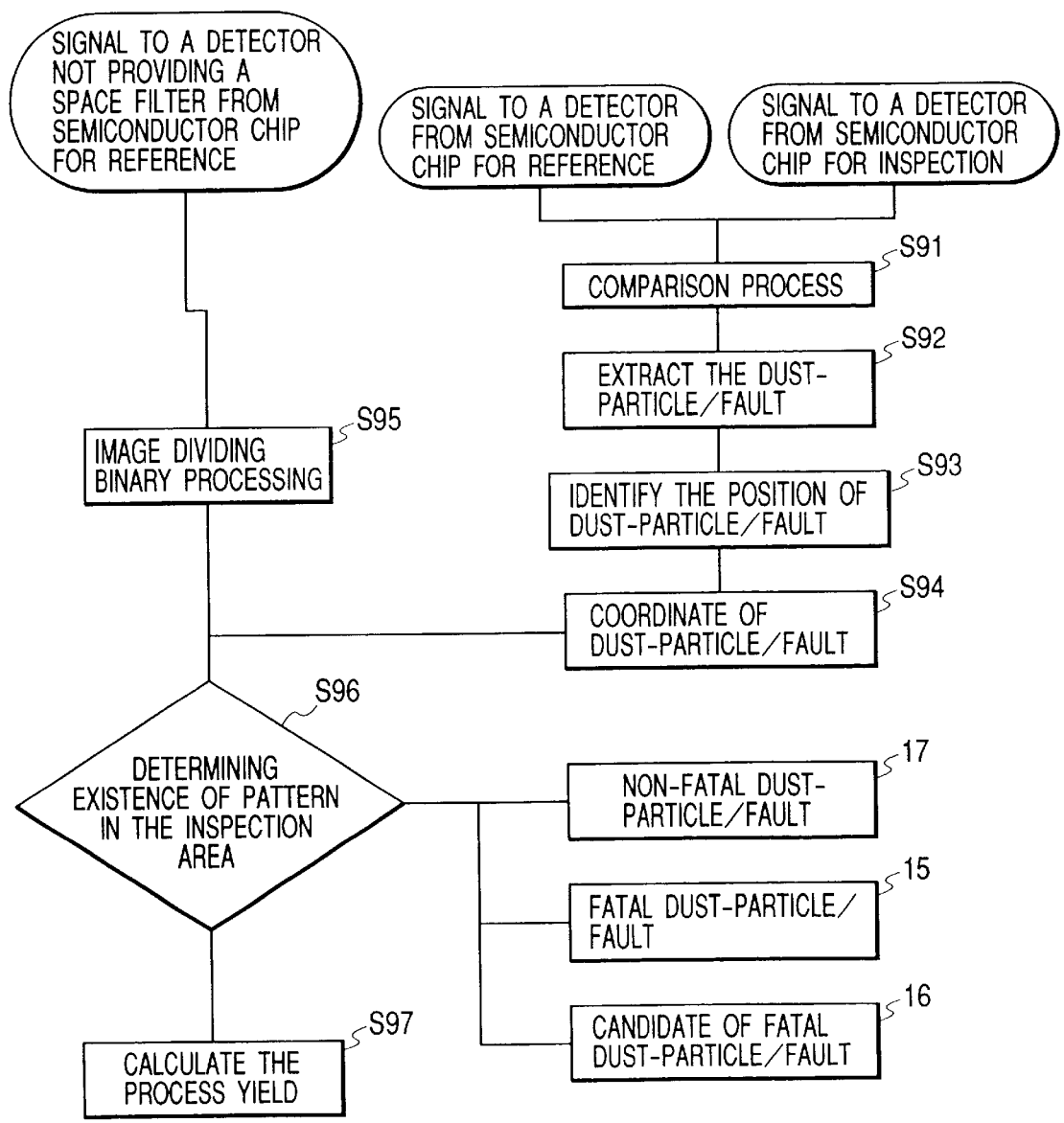
FIG. 37 is the flow diagram of inspection sequence illustrating an example of the inspection sequence executed in the inspection process of the semiconductor device manufacturing method of the embodiment 10 of the present invention.

FIG. 37 is the flow diagram of inspection sequence illustrating an example of the inspection sequence executed in the inspection process of the semiconductor device manufacturing method of the embodiment 10 of the present invention.

In the semiconductor manufacturing method of the embodiment 10, the fatal/non-fatal condition of the dust-particles/fault 8 is determined using the external appearance inspection apparatus which is almost similar to that used in the semiconductor manufacturing process of the embodiment 4.

Here, difference from the external appearance inspection apparatus of FIG. 18 of the embodiment 4 will be explained in regard to the structure of the external appearance inspection apparatus of the embodiment 10 of FIG. 34.

The external appearance inspection apparatus of the embodiment 10 of FIG. 34 is the dark field type apparatus in which a half-mirror 46 is provided between the lens 30 and space filter 31 (filter) on the optical path 16 of the scatting/diffracting beam 3b of the external appearance inspection apparatus of the embodiment 4 of FIG. 18 and moreover a binary processing system detector 47 is also provided to the binary processing system (image dividing binary processing system 49) for determining the fatal/non-fatal dust-particles/fault.

Accordingly, detection of size and position of dust-particles/fault 8 and determination of fatal/non-fatal dust-particles/fault are performed sequentially and almost simultaneously by simultaneously fetching the scattering/diffracting beam 3b from the semiconductor wafer 2 of the laser beam 3a to both detector 4 and binary processing system detector 47 with the half-mirror 46.

The other structure of the external appearance inspection apparatus of the embodiment 10 is almost similar to that of the embodiment 4 and therefore the same explanation is not repeated here.

Next, the semiconductor device manufacturing method of the embodiment 10 will be explained.

Here, only the method of determining the fatal/non-fatal condition of the dust-particle/fault 8 of the embodiment 10 is explained and since the other semiconductor device manufacturing method is similar to that of the embodiment 4, the same explanation is not repeated here.

First, when the inspection chip 6 of semiconductor wafer 2 on the stage 1 is irradiated with the laser beam 3a (optical beams) from the laser 3, the laser beam 3a is reflected with the semiconductor wafer 2 to become the scattering/diffracting beam 3b and this scattering/diffracting beam 3b enters the detector 4 passing through the lens 30, half-mirror 46 and space filter 31. Thereby, the signal from pattern 10 (refer to FIG. 4) and the signal from dust-particle/fault 8 are detected with the detector 4.

Moreover, the image signal of inspection chip 6 fetched by the detector 4 (inspection chip information) is transmitted to the detected image comparison processing system 5.

In this detected image comparison processing system 5, the image signal from inspection chip 6 (inspection chip information) and the image signal from reference chip 7 (reference chip information) are compared (step S91 of FIG. 37). Namely, a difference between the image signal of inspection chip 6 and the previously stored image signal of reference chip 7 adjacent to the inspection chip 6 is obtained when this difference value is larger than the maximum value Thnmax (not illustrated) of the difference value of pattern 10, the dust-particle/fault 8 is determined as dust-particle and when such difference value is smaller than such maximum value, the dust-particle/fault 8 is determined as the pattern 10.

Thereafter, the dust-particle/fault 8 is extracted depending on the determination result of the detected image comparison processing system 5 (step S92).

This comparison process is performed for the entire part of the surface of semiconductor wafer 2 by moving the stage 1 while controlling the stage controller with the central control system 9.

As a result, position of the dust-particle/fault 8 on the semiconductor wafer 2 (step S93) may be identified and the chip matrix 11 for identifying the chip and chip coordinate 12 in the XY direction as the orthogonal coordinate from the predetermined reference origin in the chip for such position may be stored in the inspection apparatus memory system 13 provided in the external appearance inspection apparatus as illustrated in FIG. 3.

Thereby, the coordinate of dust-particle/fault 8 on the semiconductor wafer 2 can be obtained and moreover a size of dust-particle/fault 8 can also be calculated using the image comparison processing system (step S94).

The information about position and size of the dust-particles/fault 8 is called the dust-particle/fault information.

Meanwhile, in the embodiment 10, during such inspection, the optical path of the scattering/diffracting beam 3b of the laser beam 3a from the semiconductor wafer 3 is changed with the half-mirror 46 and thereby the optical beam 46a reflected from the half-mirror 46 is fetched as the dark field image with the binary processing system detector 47.

Moreover, the reference chip information is obtained through detection of the half-mirror reflected optical beam 46a of the binary processing system detector 47 and the reference chip information obtained as explained above is then subjected to the binary-process as the image dividing binary process in order to obtain the pattern information of reference chip (step S95).

In this case, the dark field image fetched to the binary processing system detector 47 is divided, for example, into 64 square areas (=8×8) as illustrated in FIG. 36(a) and thereafter the binary process is conducted to define the bright area as "1" through the predetermined threshold value process for the bright areas in respective cells as illustrated in FIG. 36(b) and the information obtained by such binary process is defined as the pattern information.

Here, as illustrated in FIG. 36(b), 31 square areas defined as "1" among the 64 square areas.

Thereafter, the pattern information obtained in the image dividing binary processing system 49 is transmitted to the central control system 9.

The central control system 9 determines existence or no-existence of the pattern based on the pattern information of the reference chip 7 for the position of dust-particle/fault 8 based on the dust-particle/fault information using the dust-particle/fault information such as position coordinate and size of dust-particle/fault 8 and the pattern information obtained through the binary process (step S96).

Namely, when "1" is defined to at least one cell in terms of the value of binary process in the cells corresponding to the position of dust-particle/fault 8 in the comparison of the dust-particle/fault information and the pattern information of reference chip 7, this dust-particle/fault 8 is determined as the fatal dust-particle/fault and it is then recorded and stored in the inspection apparatus memory system 13 of FIG. 35 as the fatal dust-particle/fault 15 as illustrated in FIG. 37.

Moreover, when "1" is defined to at least one adjacent cell of one or a plurality of cells corresponding to the coordinate and size of the dust-particle/fault 8, this dust-particle/fault 8 is defined as the candidate of fatal dust-particle/fault and it is recorded and stored in the inspection apparatus memory system 13 as the candidate of fatal dust-particle/fault 16.

In other cases, the dust-particle/fault 8 is determined as the non-fatal dust-particle/fault and it is then recorded and stored in the inspection apparatus memory system 13 as the non-fatal dust-particle/fault 17.

Thereafter, the fatal, candidate of fatal or non-fatal condition is recorded to the chip including the dust-particles/fault 8 determined as the fatal, candidate of fatal or non-fatal dust-particle/fault and it is then stored in the inspection apparatus memory system 13.

Moreover, the estimated maximum yield and estimated minimum yield of the manufacturing process of the semiconductor wafer 2 used in this inspection are calculated respectively using the number of non-fatal chips and the number of fatal chips (step S97).

Display type and method of determination result for fatal/non-fatal dust-particle/fault in the external appearance inspection apparatus of the embodiment 10, structure and function of the analyzing apparatus (external apparatus) electrically connected to the external appearance inspection apparatus and effect of the semiconductor device manufacturing method of the embodiment 10 are similar to that of the embodiment 4 and therefore same explanation is not repeated here.

The present invention has been explained practically based on the embodiments thereof but the present invention is not limited only to the embodiments explained above and it naturally allows various changes or modifications within the scope of the invention.

For example, in the embodiments 1 to 10, the inspection object of the external appearance inspection apparatus is defined as the semiconductor wafer 2 but such inspection object may be a reticle or liquid crystal substrate other than the semiconductor wafer 2.

Moreover, a laser 3 is used as the light source for emitting the monochromatic optical beam in the embodiments 1 to 10 but the light source other than laser 3, which can generate the monochromatic optical beam, may be used and moreover the device other than lamp 41 may also be used as the light source for emitting the visible optical beam.

The effects obtained by the typical invention among those disclosed in this specification may be summarized as listed below.

(1) Determination of fatal dust-particle/fault may be realized using the external appearance inspection apparatus in the semiconductor manufacturing process and thereby it is now possible to the contribution rate to the yield of product.

(2) It is now possible, from the item (1), to analyze and take a measure for the dust-particle/fault having the higher fatal condition and thereby high efficient improvement of yield can also be realized.

What is claimed is:

1. A method of manufacturing semiconductor device comprising processes for:

fetching inspection chip information as the information including dust-particle/fault on said inspection chip by irradiating said inspection chip of a semiconductor wafer supported with a movable stage with an optical beam and by detecting the scattering/diffracting beam of said optical beam;

fetching reference chip information as the information of said reference chip by irradiating said reference chip, with said optical beam, which is estimated as not including dust-particle/fault of said semiconductor wafer;

obtaining dust-particle/fault information as the information about position and size of said dust-particle/fault on said inspection chip by comparing said inspection chip information with said reference chip information;

determining whether said dust-particle/fault is located on the pattern or in the outside of pattern by matching between said dust-particle/fault information and the design pattern data as the data of the prepared pattern; and defining said dust-particle/fault as the fatal dust-particle/fault when said dust-particle/fault is located on the pattern or as the non-fatal dust-particle/fault when said dust-particle/fault is located in the outside the pattern.

2. A method of manufacturing semiconductor device comprising processes for:

fetching first area information as the information including the dust-particle/fault of the first area of the main surface of said semiconductor wafer by irradiating the main surface of semiconductor wafer supported with the movable stage with an optical beam and then detecting the scattering/diffracting beam of said optical beam;

fetching second area information as the information of a second area by irradiating said second area, with the optical beam, which is different from said first area of said semiconductor wafer;

obtaining dust-particle/fault information as the information about position and size of the dust-particle/fault of said first area by comparing said first area information with said second area information;

obtaining pattern information of said second area with the Fourier image processing system by fetching the Fourier image of said second area;

determining existence of the pattern based on said pattern information of said second area for the position of dust-particle/fault based on said dust-particle/fault information; and defining said dust-particle/fault as the fatal dust-particle/fault when it is determined that said pattern exists at the position of said dust-particle/fault and also defining said dust-particle/fault as the non-fatal dust-particle/fault when it is determined that said pattern does not exist in the position of said dust-particle/fault.

3. A method of manufacturing semiconductor device comprising processes for:

fetching inspection chip information as the information including a dust-particle/fault on said inspection chip by irradiating said inspection chip of semiconductor wafer supported with a movable stage with an optical beam and then detecting the scattering/diffracting beam of said optical beam;

fetching reference chip information as the information of said reference chip by irradiating, with said optical beam, the reference chip which is estimated as having no dust-particle/fault of said semiconductor wafer;

obtaining the dust-particle/fault information as the information about position and size of said dust-particle/fault on said inspection chip by comparing said inspection chip information with said reference chip information;

obtaining pattern information of said reference chip by executing the threshold value process to said reference chip information;

determining existence of pattern based on said pattern information of said reference chip to said dust-particle/fault based on said dust-particle/fault information; and defining said dust-particle/fault as the fatal dust-particle/fault when said pattern exists at the position of said dust-particle/fault or as the non-fatal dust-particle/fault when said pattern does not exist at the position of said dust-particle/fault.

4. A method of manufacturing semiconductor device comprising processes for:

fetching inspection chip information as the information including a dust-particle/fault on said inspection chip by irradiating, with an optical beam, said inspection chip of semiconductor wafer supported with a movable stage and detecting the scattering/diffracting beam of said optical beam using a filter;

fetching reference chip information as said reference chip information by detecting the scattering/diffracting beam of said optical beam using a filter after the reference chip which is estimated as having no dust-particle/fault of said semiconductor wafer is irradiated with said optical beam;

obtaining dust-particle/fault information as the information about position and size of said dust-particle/fault on said inspection chip by comparing said inspection chip information with said reference chip information;

obtaining pattern information of said reference chip by obtaining said reference chip information by irradiating said reference chip with said optical beam and detecting the scattering/diffracting beam of said optical beam without use of a filter and then executing the binary process to this reference chip information;

determining existence of pattern based on said pattern information of said reference chip for the position of said dust-particle/fault based on said dust-particle/fault information; and defining said dust-particle/fault as the fatal dust-particle/fault when it is determined that said pattern is located at the position of said dust-particle/fault or as the non-fatal dust-particle/fault when it is determined that said pattern is not located at the position of said dust-particle/fault.

5. A method of manufacturing semiconductor device comprising processes for:

obtaining chip information including a pattern information of said semiconductor chip and then storing said chip information to chip information memory means by irradiating a semiconductor chip of semiconductor wafer supported with a movable stage with an optical beam and then detecting the scattering/diffracting beams of said optical beam;

fetching inspection chip information as the information including a dust-particle/fault on said inspection chip by irradiating said inspection chip of said semiconductor wafer supported with said stage with an optical beam and then detecting the scatting/diffracting beam of said optical beam;

fetching reference chip information as the information of said reference chip by irradiating, with said optical beam, the reference chip which is estimated as having no dust-particle/fault of said semiconductor wafer and thereafter detecting the scattering/diffracting beam of said optical beam;

obtaining dust-particle/fault information as the information about position and size of said dust-particle/fault on said inspection chip by comparing said inspection chip information with said reference chip information;

determining existence of a pattern based on said pattern information of said semiconductor chip for the position of said dust-particle/fault based on said dust-particle/fault information by extracting said pattern information of said semiconductor chip of said chip information memory means; and defining said dust-particle/fault as the fatal dust-particle/fault when it is determined that said pattern is located at the position of said dust-particle/fault or as the non-fatal dust-particle/fault when it is determined that said pattern is not located at the position of said dust-particle/fault.

6. A method of manufacturing semiconductor device comprising processes for:

fetching inspection chip information as the information including a dust-particle/fault on said inspection chip by irradiating said inspection chip of semiconductor wafer supported with a movable stage with a monochromatic optical beam;

fetching reference chip information as the information of said reference chip by irradiating, with said monochromatic optical beam, the reference chip which is estimated as having no dust-particle/fault of said semiconductor wafer;

obtaining the dust-particle/fault information as the information about position and size of said dust-particle/fault on said inspection chip by comparing said inspection chip information with said reference chip information;

fetching, after said dust-particle/fault information is obtained using said monochromatic optical beam, the chip information for visible beam inspection as the information including a dust-particle/fault on said inspection chip by irradiating said inspection chip with a visible optical beam;

fetching chip information for visible optical beam reference as the information of said reference chip by irradiating said reference chip with said visible optical beam after said dust-particle/fault information is obtained using said monochromatic optical beam;

executing the threshold value process to the pattern information of chip information for reference of said visible optical beam obtained by comparing said chip information for visible beam optical inspection with the chip information for said visible beam reference;

determining existence of a pattern based on said pattern information after said threshold value process of said reference chip for the position of said dust-particle/fault based on said dust-particle/fault information; and defining said dust-particle/fault as the fatal dust-particle/fault when it is determined that said pattern is located at the position of said dust-particle/fault or as the non-fatal dust-particle/fault when it is determined that said pattern is not located at the position of said dust-particle/fault.

7. A method of manufacturing semiconductor device comprising processes for;

fetching inspection chip information as the information including a dust-particle/fault on said inspection chip by irradiating, with an optical beam, said inspection chip of semiconductor wafer supported with a movable stage and detecting the scattering/diffracting beam of said optical beam using a filter;

fetching reference chip information as said reference chip information by detecting the scattering/diffracting beam of said optical beam using a filter after the reference chip which is estimated as having no dust-particle/fault of said semiconductor wafer is irradiated with said optical beam and detecting, on the other hand, a half-mirror reflected beam by reflecting said scatting/diffracting beam with a half-mirror in order to obtain the chip information for mirror reference and obtaining pattern information of said reference chip by executing the binary process to the chip information for mirror reference;

obtaining dust-particle/fault information as the information about position and size of said dust-particle/fault on said inspection chip by comparing said inspection chip information with said reference chip information;

determining existence of a pattern based on said pattern information of said reference chip for the position of said dust-particle/fault based on said dust-particle/fault information; and defining said dust-particle/fault as the fatal dust-particle/fault when it is determined that said pattern is located at the position of said dust-particle/fault or as the non-fatal dust-particle/fault when it is determined that said pattern is not located at the position of said dust-particle/fault.

8. A method of manufacturing semiconductor device according to the claim 1, 2, 3, 4, 5, 6 or 7, wherein any one of the chip map information for determining said fatal/non-fatal condition of said dust-particle/fault of said semiconductor wafer, time series transition information for determining said fatal/non-fatal condition or manufacturing process tracking information for determination of said fatal/non-fatal condition is displayed in the external appearance inspection apparatus which can determine the fatal/non-fatal condition of said dust-particle/fault.

9. A method of manufacturing semiconductor device according to claim 1, 2, 3, 4, 5, 6, 7 or 8, wherein the determination result information of said fatal/non-fatal condition of said dust-particle/fault is transmitted to a distribution management station in the external apparatus electrically connected to the external appearance inspection apparatus having conducted said determination and distribution in the semiconductor manufacturing process is managed on the basis of said determination result information with said distribution management station.

* * * * *